US008691243B2

(12) United States Patent
Mizrachi Nebenzahl

(10) Patent No.: US 8,691,243 B2
(45) Date of Patent: Apr. 8, 2014

(54) **PROTEIN-BASED *STREPTOCOCCUS PNEUMONIAE* VACCINE**

(71) Applicant: Ben-Gurion University of the Negev Research and Development Authority, Beer-Sheva (IL)

(72) Inventor: Yaffa Mizrachi Nebenzahl, Beer-Sheva (IL)

(73) Assignee: Ben-Gurion University of the Negev Research and Development Authority, Beer Sheva (IL)

( * ) Notice: Subject to any disclaimer, the term of this patent is extended or adjusted under 35 U.S.C. 154(b) by 0 days.

(21) Appl. No.: 13/734,350

(22) Filed: Jan. 4, 2013

(65) Prior Publication Data

US 2013/0108659 A1    May 2, 2013

Related U.S. Application Data

(60) Continuation-in-part of application No. 12/435,781, filed on May 5, 2009, now abandoned, which is a continuation-in-part of application No. 12/363,383, filed on Jan. 30, 2009, now abandoned, which is a division of application No. 10/953,513, filed on Sep. 30, 2004, now Pat. No. 7,504,110, which is a continuation-in-part of application No. PCT/IL03/00271, filed on Apr. 1, 2003.

(60) Provisional application No. 60/368,981, filed on Apr. 2, 2002.

(51) Int. Cl.
*A61K 39/09* (2006.01)
*A61K 39/02* (2006.01)
*A61K 39/00* (2006.01)
*A61K 38/00* (2006.01)
*C07K 1/00* (2006.01)

(52) U.S. Cl.
USPC ............. 424/244.1; 424/234.1; 424/184.1; 424/190.1; 514/1.1; 530/350; 530/825

(58) Field of Classification Search
None
See application file for complete search history.

(56) References Cited

U.S. PATENT DOCUMENTS

| | | |
|---|---|---|
| 5,728,387 A | 3/1998 | Briles et al. ............... 424/234.1 |
| 6,100,069 A | 8/2000 | Biswas et al. |
| 6,217,884 B1 | 4/2001 | Sampson et al. ........... 424/244.1 |
| 6,699,703 B1 | 3/2004 | Doucette-Stamm et al. ................ 435/252.3 |
| 6,800,744 B1 | 10/2004 | Doucette-Stamm et al. 536/23.1 |
| 7,078,492 B2 | 7/2006 | Pirofski et al. ............. 530/387.3 |
| 7,384,775 B2 | 6/2008 | Zagursky et al. |
| 2004/0029129 A1 | 2/2004 | Wang et al. ...................... 435/6 |
| 2005/0020813 A1* | 1/2005 | Masignani et al. .......... 530/350 |
| 2009/0148470 A1 | 6/2009 | Mizrachi Nebenzahl . 424/190.1 |
| 2009/0202528 A1* | 8/2009 | Kofoed et al. ............. 424/133.1 |

FOREIGN PATENT DOCUMENTS

| | | |
|---|---|---|
| EP | 0 899 334 A2 | 3/1999 |
| WO | 99/23212 A1 | 5/1999 |
| WO | 99/27074 A1 | 6/1999 |
| WO | WO 01/70955 A2 | 9/2001 |
| WO | WO 02/22168 A2 | 3/2002 |
| WO | 02/077021 A2 | 10/2002 |
| WO | 02/083855 A2 | 10/2002 |
| WO | 2006/084467 A1 | 8/2006 |

OTHER PUBLICATIONS

U.S. Appl. No. 10/953,513 Requirement for Restriction/Election dated Mar. 20, 2007.
U.S. Appl. No. 10/953,513 Non-Final Rejection dated Jul. 9, 2007.
U.S. Appl. No. 10/953,513 Final Rejection dated Jul. 9, 2008.
U.S. Appl. No. 10/953,513 Advisory Action dated Oct. 2, 2008.
U.S. Appl. No. 12/363,383 Requirement for Restriction/Election dated Feb. 4, 2011.
U.S. Appl. No. 12/435,781 Requirement for Restriction/Election dated Jun. 6, 2011.
U.S. Appl. No. 12/435,781 Requirement for Restriction/Election dated Feb. 9, 2012.
U.S. Appl. No. 12/435,781 Non-Final Rejection dated May 7, 2012.
U.S. Appl. No. 12/435,781 Final Rejection dated Nov. 9, 2012.
European Search Report, Appl. No. EP 10 01 1328 dated Feb. 18, 2011.
Argiro, Laurent et al., (2000) Identification of a candidate vaccine peptide on the 37 kDa Schistosoma mansoni GAPDH. Vaccine 18:2039-2048.
Attali, Cecile et al., (2008) *Streptococcus pneumoniae* choline-binding protein E interaction with plasminogen/plasmin stimulates migration across the extracellular matrix. Infect and Immun. 76(2):466-476.
Briles, David E. et al., (1998) Pneumococcal diversity: considerations for new vaccine strategies with emphasis on pneumococcal surface protein A (PspA). Clinical Microbiology Reviews 11(4):645-657.
Briles D. E. et al., (2001) "The potential for using protein vaccines to protect against otitis media caused by *Streptococcus pneumoniae*" Vaccine, Dec. 8; 19 Suppl 1:S87-S95.
Briles, David E. et al., (2000) "Intranasal Immunization of Mice with a Mixture of the Pneumococcal Proteins PsaA and PspA is Highly Protective against Nasopharyngeal Carriage of *Streptococcus pneumonia*". Infect. and Immun. 68(2):796-800.
Bethe G. et al., (2001) "The cell wall-associated serine protease PrtA: a highly conserved virulence factor of Streptococcus pneumoniae". FEMS Microbiol Lett. 205:99-104.
Daniely, D. et al., (2006) "Pneumococcal 6-phosphogluconate-dehydrogenase, a putative adhesin, induces protective immune response in mice". Clinical and Experimental Immunology 144:254-263.

(Continued)

*Primary Examiner* — S. Devi
(74) *Attorney, Agent, or Firm* — Winston & Strawn LLP

(57) ABSTRACT

Vaccine compositions and methods for protecting a mammalian subject against infection with *S. pneumoniae* are disclosed. The vaccines and methods comprise an effective amount of one or more *Streptococcus pneumoniae* cell wall and/or cell membrane proteins and/or immunogenically-active fragments, derivatives or modifications thereof, wherein the proteins are selected from a defined group of proteins associated with age-dependent immunological responses.

4 Claims, 12 Drawing Sheets

(56) References Cited

OTHER PUBLICATIONS

De Velasco, E. Alonso et al., (1995) "*Streptococcus pneumoniae*: virulence factors, pathogenesis, and vaccines". Microbiol. Reviews 59(4):591-603.

Houghten, R. A. et al. (1986) "Relative Importance of Position and Individual Amino Acid Residues in Peptide Antigen-Antibody Interactions: Implications in the Mechanism of Antigenic Drift and Antigenic Shift". Vaccines, Cold Spring Harbor Laboratory:21-25.

Jado, I. et al. (1999) "Cloning, Sequencing, and Chromosomal Location of a Putative Class-II Aldolase Gene from *Streptococcus Pneumoniae*". Current Microbiol. 39: 31-36.

Jedrzejas, M. J., (2001) "Pneumococcal Virulence Factors: Structure and Function", Microbiology and Molecular Biology Reviews. 65(2):187-207.

Johnson, Scott E. et al., (2002) "Inhibition of pneumococcal carriage in mice by subcutaneous immunization with peptides from the common surface protein pneumococcal surface adhesin A". *J. of Infect. Dis.* 185:489-496.

Lawrence, Michael C. et al., (1998) "The crystal structure of pneumococcal surface antigen PsaA reveals a metal-binding site and a novel structure for a putative ABC-type binding protein". *Structure* 6:1553-1561.

Lifshitz et al., (2002) "Age-dependent preference in human antibody responses to *Streptococcus pneumonia* polypeptide antigens". Clin. Exp. Immunol. 127:344-353.

Ling et al., (2002) "Surface Lectin (L) and Non-Lectin (NL) Proteins as Novel Vaccine Candidates for *S. pnuemoniae* (Pnc).", Abstracts of the Interscience Conference on Antimicrobial Agents and Chemotherapy, American Society for Microbiology, San Diego, CA, Sep. 27-30, vol. 42, p. 247, abstract.

Ling, E. et al., (2004) "Glycolytic enzymes associated with the cell surface of *Streptococcus pneumoniae* are antigenic in humans and elicit protective immune responses in the mouse". Clin. Exp. Immunol 138:290-298.

McDaniel, (2002) "Analysis of Protection Eliciting Pneumococcal Cell Surface Components form PSPA (Pneumococcal Surface Protein A) Mutants", Abstracts of the Interscience Conference on Antimicrobial Agents and Chemotherapy, American Society for Microbiology, San Diego, CA, Sep. 27-30, p. A1257.; abstract.

Seo, Jun-Young et al., (2002) "Cross-Protective Immunity of Mice Induced by Oral Immunization with Pneumococcal Surface Adhesin A Encapsulated in Microspheres". Infect. And Immun. 70(3):1143-1149.

Auzat et al., "The NADH oxidase of Streptococcus pneumoniae: its involvement in competence and virulence", Mol, Microbiol., 34(5):1018-1028 (1999).

Blau et al., "Flamingo cadherin: a putative host receptor for Streptococcus pneumoniae", J, Infect. Dis. 195:1828-1837 (2007).

Hoskins et al., "Genome of the bacterium Streptococcus pneumoniae strain R6", J. Bacteriol. 183(19):5709-5717 (2001).

Lifshitz et al., "*Streptococaus pneumoniae* (Pnc) surface proteins: profile of antibody response during health, disease and convalescence", Abstracts of the 39th interscience conference on antimicrobial agents and chemotherapy, American society for microbiology, San Francisco, CA, Sep. 26-29, p. 360, abstract No. 244 (1999).

Lortie et al., "The gene encoding IIAB(Man)L in *Streptococcus salivarius* is part of a tetracistronic operon encoding a phosphoenolpyruvate: mannose/glucose phosphotransferase system", Microbiology 146:677-685 (2000).

McDaniel et al., "A pneumococcal surface protein (PspB) that exhibits the same protease sensitivity as streptococcal R antigen", Infect. And Immun. 56(11):3001-3003 (1988).

Shapera et al., "Host factors and capsular typing of body fluid isolates in fulminant pneumococcal infections", Infect. and Immun. 5(1):132-136 (1972).

Shapiro et al., "The protective efficacy of polyvalent pneumococcal polysaccharide vaccine", N. Engl. J. Med. 325(21): 1453-1460 (1991).

Tettelin et al., "Complete genome sequence of a virulent isolate of Streptococcus pneumoniae", Science 293(5529): 498-506 (2001).

Wizemann et al., "Use of a whole genome approach to identify vaccine molecules affording protection against Streptococcus pneumoniae infection", Infect. and Immun. 69(3):1593-1598 (2001).

Yu et al., "Characterization of the *Streptococcus pneumoniae* NADH oxidase that is required for infection",Microbiology 147:431-438 (2001).

\* cited by examiner

SEQUENCE LISTING

<160> NUMBER OF SEQ ID NOS: 36

<210> SEQ ID NO 1
<211> LENGTH: 294
<212> TYPE: DNA
<213> ORGANISM: Streptococcus pneumoniae

<400> SEQUENCE: 1

```
atggcaatcg tttcagcaga aaaatttgtc caagcagccc gtgacaacgg ttatgcagtt      60
ggtggattta acacaaacaa ccttgagtgg actcaagcta tcttgcgcgc agcagaagct     120
aaaaaagctc cagtttttgat ccaaacttca atgggtgctg ctaaatacat gggtggttac     180
aaagttgctc gcaacttgat cgctaacctt gttgaatcaa tgggtatcac tgtaccagta     240
gctatccacc ttgaccacgg tcactacgaa gatgcacttg agtgtatcga agtt           294
```

```
<210> SEQ ID NO 2
<211> LENGTH: 24
<212> TYPE: DNA
<213> ORGANISM: Artificial Sequence
<220> FEATURE:
<223> OTHER INFORMATION: PRIMER

<400> SEQUENCE: 2
ggtaccatgg caatcgtttc agca                                          24

<210> SEQ ID NO 3
<211> LENGTH: 27
<212> TYPE: DNA
<213> ORGANISM: Artificial Sequence
<220> FEATURE:
<223> OTHER INFORMATION: PRIMER

<400> SEQUENCE: 3
gagctcacca acttcgatac actcaag                                       27

<210> SEQ ID NO 4
<211> LENGTH: 577
<212> TYPE: PRT
<213> ORGANISM: Streptococcus pneumoniae

<400> SEQUENCE: 4
```

Met Thr Glu Met Leu Lys Gly Ile Ala Ala Ser Asp Gly Val Ala Val
1               5                   10                  15

Ala Lys Ala Tyr Leu Leu Val Gln Pro Asp Leu Ser Phe Glu Thr Ile
                20                  25                  30

Thr Val Glu Asp Thr Asn Ala Glu Glu Ala Arg Leu Asp Ala Ala Leu
            35                  40                  45

Gln Ala Ser Gln Asp Glu Leu Ser Val Ile Arg Glu Lys Ala Val Gly
        50                  55                  60

Thr Leu Gly Glu Glu Ala Ala Gln Val Phe Asp Ala His Leu Met Val
65                  70                  75                  80

Leu Ala Asp Pro Glu Met Ile Ser Gln Ile Lys Glu Thr Ile Arg Ala
                85                  90                  95

Lys Lys Val Asn Ala Glu Ala Gly Leu Lys Glu Val Thr Asp Met Phe
            100                 105                 110

Ile Thr Ile Phe Glu Gly Met Glu Asp Asn Pro Tyr Met Gln Glu Arg
        115                 120                 125

Ala Ala Asp Ile Arg Asp Val Thr Lys Arg Val Leu Ala Asn Leu Leu
    130                 135                 140

Gly Lys Lys Leu Pro Asn Pro Ala Ser Ile Asn Glu Glu Val Ile Val
145                 150                 155                 160

Ile Ala His Asp Leu Thr Pro Ser Asp Thr Ala Gln Leu Asp Lys Asn
                165                 170                 175

Phe Val Lys Ala Phe Val Thr Asn Ile Gly Gly Arg Thr Ser His Ser
            180                 185                 190

Ala Ile Met Ala Arg Thr Leu Glu Ile Ala Ala Val Leu Gly Thr Asn
        195                 200                 205

Asn Ile Thr Glu Ile Val Lys Asp Gly Asp Ile Leu Ala Val Asn Gly
    210                 215                 220

Ile Thr Gly Glu Val Ile Ile Asn Pro Thr Asp Glu Gln Ala Ala Glu
225                 230                 235                 240

Phe Lys Ala Ala Gly Glu Ala Tyr Ala Lys Gln Lys Ala Glu Trp Ala
                245                 250                 255

```
Leu Leu Lys Asp Ala Gln Thr Val Thr Ala Asp Gly Lys His Phe Glu
            260                 265                 270

Leu Ala Ala Asn Ile Gly Thr Pro Lys Asp Val Glu Gly Val Asn Asn
            275                 280                 285

Asn Gly Ala Glu Ala Val Gly Leu Tyr Arg Thr Glu Phe Leu Tyr Met
290                 295                 300

Asp Ser Gln Asp Phe Pro Thr Glu Asp Glu Gln Tyr Glu Ala Tyr Lys
305                 310                 315                 320

Ala Val Leu Glu Gly Met Asn Gly Lys Pro Val Val Arg Thr Met
                325                 330                 335

Asp Ile Gly Gly Asp Lys Glu Leu Pro Tyr Phe Asp Met Pro His Glu
            340                 345                 350

Met Asn Pro Phe Leu Gly Phe Arg Ala Leu Arg Ile Ser Ile Ser Glu
            355                 360                 365

Thr Gly Asp Ala Met Phe Arg Thr Gln Ile Arg Ala Leu Leu Arg Ala
    370                 375                 380

Ser Val His Gly Gln Leu Arg Ile Met Phe Pro Met Val Ala Leu Leu
385                 390                 395                 400

Lys Glu Phe Arg Ala Ala Lys Ala Val Phe Asp Glu Lys Ala Asn
                405                 410                 415

Leu Leu Ala Glu Gly Val Ala Val Ala Asp Asn Ile Gln Val Gly Ile
            420                 425                 430

Met Ile Glu Ile Pro Ala Ala Met Leu Ala Asp Gln Phe Ala Lys
    435                 440                 445

Glu Val Asp Phe Phe Ser Ile Gly Thr Asn Asp Leu Ile Gln Tyr Thr
        450                 455                 460

Met Ala Ala Asp Arg Met Asn Glu Gln Val Ser Tyr Leu Tyr Gln Pro
465                 470                 475                 480

Tyr Asn Pro Ser Ile Leu Arg Leu Ile Asn Asn Val Ile Lys Ala Ala
                485                 490                 495

His Ala Glu Gly Lys Trp Ala Gly Met Cys Gly Glu Met Ala Gly Asp
            500                 505                 510

Gln Gln Ala Val Pro Leu Leu Val Gly Met Gly Leu Asp Glu Phe Ser
        515                 520                 525

Met Ser Ala Thr Ser Val Leu Arg Thr Arg Ser Leu Met Lys Lys Leu
530                 535                 540

Asp Thr Ala Lys Met Glu Glu Tyr Ala Asn Arg Ala Leu Thr Glu Cys
545                 550                 555                 560

Ser Thr Met Glu Glu Val Leu Glu Leu Gln Lys Glu Tyr Val Asn Phe
                565                 570                 575

Asp

<210> SEQ ID NO 5
<211> LENGTH: 450
<212> TYPE: PRT
<213> ORGANISM: Streptococcus pneumoniae

<400> SEQUENCE: 5

Met Gly Lys Tyr Phe Gly Thr Asp Gly Val Arg Gly Glu Ala Asn Leu
1               5                   10                  15

Glu Leu Thr Pro Glu Leu Ala Phe Lys Leu Gly Arg Phe Gly Gly Tyr
            20                  25                  30

Val Leu Ser Gln His Glu Thr Glu Ala Pro Lys Val Phe Val Gly Arg
        35                  40                  45
```

-continued

```
Asp Thr Arg Ile Ser Gly Glu Met Leu Glu Ser Ala Leu Val Ala Gly
     50                  55                  60

Leu Leu Ser Val Gly Ile His Val Tyr Lys Leu Gly Val Leu Ala Thr
 65                  70                  75                  80

Pro Ala Val Ala Tyr Leu Val Glu Thr Glu Gly Ala Ser Ala Gly Val
                     85                  90                  95

Met Ile Ser Ala Ser His Asn Pro Ala Leu Asp Asn Gly Ile Lys Phe
                100                 105                 110

Phe Gly Gly Asp Gly Phe Lys Leu Asp Asp Glu Lys Glu Ala Glu Ile
                115                 120                 125

Glu Ala Leu Leu Asp Ala Glu Asp Thr Leu Pro Arg Pro Ser Ala
                130                 135                 140

Glu Gly Leu Gly Ile Leu Val Asp Tyr Pro Glu Gly Leu Arg Lys Tyr
145                 150                 155                 160

Glu Gly Tyr Leu Val Ser Thr Gly Thr Pro Leu Asp Gly Met Lys Val
                     165                 170                 175

Ala Leu Asp Thr Ala Asn Gly Ala Ala Ser Thr Ser Ala Arg Gln Ile
                180                 185                 190

Phe Ala Asp Leu Gly Ala Gln Leu Thr Val Ile Gly Glu Thr Pro Asp
                195                 200                 205

Gly Leu Asn Ile Asn Leu Asn Val Gly Ser Thr His Pro Glu Ala Leu
                210                 215                 220

Gln Glu Val Val Lys Glu Ser Gly Ser Ala Ile Gly Leu Ala Phe Asp
225                 230                 235                 240

Gly Asp Ser Asp Arg Leu Ile Ala Val Asp Glu Asn Gly Asp Ile Val
                245                 250                 255

Asp Gly Asp Lys Ile Met Tyr Ile Ile Gly Lys Tyr Leu Ser Glu Lys
                260                 265                 270

Gly Gln Leu Ala Gln Asn Thr Ile Val Thr Val Met Ser Asn Leu
                275                 280                 285

Gly Phe His Lys Ala Leu Asn Arg Glu Gly Ile Asn Lys Ala Val Thr
                290                 295                 300

Ala Val Gly Asp Arg Tyr Val Val Glu Glu Met Arg Lys Ser Gly Tyr
305                 310                 315                 320

Asn Leu Gly Gly Glu Gln Ser Gly His Val Ile Leu Met Asp Tyr Asn
                     325                 330                 335

Thr Thr Gly Asp Gly Gln Leu Ser Ala Val Gln Leu Thr Lys Ile Met
                340                 345                 350

Lys Glu Thr Gly Lys Ser Leu Ser Glu Leu Ala Ala Glu Val Thr Ile
                355                 360                 365

Tyr Pro Gln Lys Leu Val Asn Ile Arg Val Glu Asn Val Met Lys Glu
                370                 375                 380

Lys Ala Met Glu Val Pro Ala Ile Lys Ala Ile Glu Lys Met Glu
385                 390                 395                 400

Glu Glu Met Ala Gly Asn Gly Arg Ile Leu Val Arg Pro Ser Gly Thr
                     405                 410                 415

Glu Pro Leu Leu Arg Val Met Ala Glu Ala Pro Thr Thr Glu Glu Val
                420                 425                 430

Asn Tyr Tyr Val Asp Thr Ile Thr Asp Val Val Arg Ala Glu Ile Gly
                435                 440                 445

Ile Asp
450
```

<210> SEQ ID NO 6

```
<211> LENGTH: 420
<212> TYPE: PRT
<213> ORGANISM: Streptococcus pneumoniae

<400> SEQUENCE: 6

Met Ser Val Ser Phe Glu Asn Lys Glu Thr Asn Arg Gly Val Leu Thr
1               5                   10                  15

Phe Thr Ile Ser Gln Asp Gln Ile Lys Pro Glu Leu Asp Arg Val Phe
            20                  25                  30

Lys Ser Val Lys Lys Ser Leu Asn Val Pro Gly Phe Arg Lys Gly His
        35                  40                  45

Leu Pro Arg Pro Ile Phe Asp Gln Lys Phe Gly Glu Glu Ala Leu Tyr
50                  55                  60

Gln Asp Ala Met Asn Ala Leu Leu Pro Asn Ala Tyr Glu Ala Ala Val
65                  70                  75                  80

Lys Glu Ala Gly Leu Glu Val Val Ala Gln Pro Lys Ile Asp Val Thr
                85                  90                  95

Ser Met Glu Lys Gly Gln Asp Trp Val Ile Thr Ala Glu Val Val Thr
            100                 105                 110

Lys Pro Glu Val Lys Leu Gly Asp Tyr Lys Asn Leu Glu Val Ser Val
        115                 120                 125

Asp Val Glu Lys Glu Val Thr Asp Ala Asp Val Glu Glu Arg Ile Glu
130                 135                 140

Arg Glu Arg Asn Asn Leu Ala Glu Leu Val Ile Lys Glu Ala Ala Ala
145                 150                 155                 160

Glu Asn Gly Asp Thr Val Val Ile Asp Phe Val Gly Ser Ile Asp Gly
                165                 170                 175

Val Glu Phe Asp Gly Gly Lys Gly Glu Asn Phe Ser Leu Gly Leu Gly
            180                 185                 190

Ser Gly Gln Phe Ile Pro Gly Phe Glu Asp Gln Leu Val Gly His Ser
        195                 200                 205

Ala Gly Glu Thr Val Asp Val Ile Val Thr Phe Pro Glu Asp Tyr Gln
210                 215                 220

Ala Glu Asp Leu Ala Gly Lys Glu Ala Lys Phe Val Thr Thr Ile His
225                 230                 235                 240

Glu Val Lys Ala Lys Glu Val Pro Ala Leu Asp Asp Glu Leu Ala Lys
                245                 250                 255

Asp Ile Asp Glu Glu Val Glu Thr Leu Ala Asp Leu Lys Glu Lys Tyr
            260                 265                 270

Ser Lys Glu Leu Ala Ala Ala Lys Glu Glu Ala Tyr Lys Asp Ala Val
        275                 280                 285

Glu Gly Ala Ala Ile Asp Thr Ala Val Glu Asn Ala Glu Ile Val Glu
290                 295                 300

Leu Pro Glu Glu Met Ile His Glu Glu Val His Arg Ser Val Asn Glu
305                 310                 315                 320

Phe Leu Gly Asn Leu Gln Arg Gln Gly Ile Asn Pro Asp Met Tyr Phe
                325                 330                 335

Gln Ile Thr Gly Thr Thr Gln Glu Asp Leu His Asn Gln Tyr Gln Ala
            340                 345                 350

Glu Ala Glu Ser Arg Thr Lys Thr Asn Leu Val Ile Glu Ala Val Ala
        355                 360                 365

Lys Ala Glu Gly Phe Asp Ala Ser Glu Glu Glu Ile Gln Lys Glu Val
370                 375                 380

Glu Gln Leu Ala Ala Asp Tyr Asn Met Glu Val Ala Gln Val Gln Asn
385                 390                 395                 400
```

```
Leu Leu Ser Ala Asp Met Leu Lys His Asp Ile Thr Ile Lys Lys Ala
                405                 410                 415

Val Glu Leu Ile
            420

<210> SEQ ID NO 7
<211> LENGTH: 693
<212> TYPE: PRT
<213> ORGANISM: Streptococcus pneumoniae

<400> SEQUENCE: 7

Met Ala Arg Glu Phe Ser Leu Glu Lys Thr Arg Asn Ile Gly Ile Met
1               5                   10                  15

Ala His Val Asp Ala Gly Lys Thr Thr Thr Glu Arg Ile Leu Tyr
            20                  25                  30

Tyr Thr Gly Lys Ile His Lys Ile Gly Glu Thr His Glu Gly Ala Ser
                35                  40                  45

Gln Met Asp Trp Met Glu Gln Glu Gln Arg Gly Ile Thr Ile Thr
    50                  55                  60

Ser Ala Ala Thr Thr Ala Gln Trp Asn His Arg Val Asn Ile Ile
65              70                  75                  80

Asp Thr Pro Gly His Val Asp Phe Thr Ile Glu Val Gln Arg Ser Leu
                85                  90                  95

Arg Val Leu Asp Gly Ala Val Thr Val Leu Asp Ser Gln Ser Gly Val
            100                 105                 110

Glu Pro Gln Thr Glu Thr Val Trp Arg Gln Ala Thr Ser Tyr Gly Val
            115                 120                 125

Pro Arg Ile Val Phe Ala Asn Lys Met Asp Lys Ile Gly Ala Asp Phe
130                 135                 140

Leu Tyr Ser Val Ser Thr Leu His Asp Arg Leu Gln Ala Asn Ala His
145                 150                 155                 160

Pro Ile Gln Leu Pro Ile Gly Ser Glu Asp Asp Phe Arg Gly Ile Ile
                165                 170                 175

Asp Leu Ile Lys Met Lys Ala Glu Ile Tyr Thr Asn Asp Leu Gly Thr
            180                 185                 190

Asp Ile Leu Glu Glu Asp Ile Pro Ala Glu Tyr Leu Asp Gln Ala Gln
            195                 200                 205

Glu Tyr Arg Glu Lys Leu Ile Glu Ala Val Ala Glu Thr Asp Glu Glu
210                 215                 220

Leu Met Met Lys Tyr Leu Glu Gly Glu Ile Thr Asn Glu Glu Leu
225                 230                 235                 240

Lys Ala Gly Ile Arg Lys Ala Thr Ile Asn Val Glu Phe Phe Pro Val
                245                 250                 255

Leu Cys Gly Ser Ala Phe Lys Asn Lys Gly Val Gln Leu Met Leu Asp
            260                 265                 270

Ala Val Ile Asp Tyr Leu Pro Ser Pro Leu Asp Ile Pro Ala Ile Lys
            275                 280                 285

Gly Ile Asn Pro Asp Thr Asp Ala Glu Glu Ile Arg Pro Ala Ser Asp
290                 295                 300

Glu Glu Pro Phe Ala Ala Leu Ala Phe Lys Ile Met Thr Asp Pro Phe
305                 310                 315                 320

Val Gly Arg Leu Thr Phe Phe Arg Val Tyr Ser Gly Val Leu Gln Ser
                325                 330                 335

Gly Ser Tyr Val Leu Asn Thr Ser Lys Gly Lys Arg Glu Arg Ile Gly
            340                 345                 350
```

Arg Ile Leu Gln Met His Ala Asn Ser Arg Gln Glu Ile Asp Thr Val
                355                 360                 365

Tyr Ser Gly Asp Ile Ala Ala Val Gly Leu Lys Asp Thr Thr Thr
        370                 375                 380

Gly Asp Ser Leu Thr Asp Glu Lys Ala Lys Ile Ile Leu Glu Ser Ile
385                 390                 395                 400

Asn Val Pro Glu Pro Val Ile Gln Leu Met Val Glu Pro Lys Ser Lys
                405                 410                 415

Ala Asp Gln Asp Lys Met Gly Ile Ala Leu Gln Lys Leu Ala Glu Glu
                420                 425                 430

Asp Pro Thr Phe Arg Val Glu Thr Asn Val Glu Thr Gly Glu Thr Val
                435                 440                 445

Ile Ser Gly Met Gly Glu Leu His Leu Asp Val Leu Val Asp Arg Met
        450                 455                 460

Arg Arg Glu Phe Lys Val Glu Ala Asn Val Gly Ala Pro Gln Val Ser
465                 470                 475                 480

Tyr Arg Glu Thr Phe Arg Ala Ser Thr Gln Ala Arg Gly Phe Phe Lys
                485                 490                 495

Arg Gln Ser Gly Gly Lys Gly Gln Phe Gly Asp Val Trp Ile Glu Phe
                500                 505                 510

Thr Pro Asn Glu Glu Gly Lys Gly Phe Glu Phe Glu Asn Ala Ile Val
                515                 520                 525

Gly Gly Val Val Pro Arg Glu Phe Ile Pro Ala Val Glu Lys Gly Leu
530                 535                 540

Val Glu Ser Met Ala Asn Gly Val Leu Ala Gly Tyr Pro Met Val Asp
545                 550                 555                 560

Val Lys Ala Lys Leu Tyr Asp Gly Ser Tyr His Asp Val Asp Ser Ser
                565                 570                 575

Glu Thr Ala Phe Lys Ile Ala Ala Ser Leu Ser Leu Lys Glu Ala Ala
                580                 585                 590

Lys Ser Ala Gln Pro Ala Ile Leu Glu Pro Met Met Leu Val Thr Ile
                595                 600                 605

Thr Val Pro Glu Glu Asn Leu Gly Asp Val Met Gly His Val Thr Ala
        610                 615                 620

Arg Arg Gly Arg Val Asp Gly Met Glu Ala His Gly Asn Ser Gln Ile
625                 630                 635                 640

Val Arg Ala Tyr Val Pro Leu Ala Glu Met Phe Gly Tyr Ala Thr Val
                645                 650                 655

Leu Arg Ser Ala Ser Gln Gly Arg Gly Thr Phe Met Met Val Phe Asp
                660                 665                 670

His Tyr Glu Asp Val Pro Lys Ser Val Gln Glu Ile Ile Lys Lys
                675                 680                 685

Asn Lys Gly Glu Asp
        690

<210> SEQ ID NO 8
<211> LENGTH: 459
<212> TYPE: PRT
<213> ORGANISM: Streptococcus pneumoniae

<400> SEQUENCE: 8

Met Ser Lys Ile Val Val Gly Ala Asn His Ala Gly Thr Ala Cys
1               5                   10                  15

Ile Asn Thr Met Leu Asp Asn Phe Gly Asn Glu Asn Glu Ile Val Val
                20                  25                  30

-continued

```
Phe Asp Gln Asn Ser Asn Ile Ser Phe Leu Gly Cys Gly Met Ala Leu
             35                  40                  45

Trp Ile Gly Glu Gln Ile Asp Gly Ala Glu Gly Leu Phe Tyr Ser Asp
     50                  55                  60

Lys Glu Lys Leu Glu Ala Lys Gly Ala Lys Val Tyr Met Asn Ser Pro
 65                  70                  75                  80

Val Leu Ser Ile Asp Tyr Asp Asn Lys Val Val Thr Ala Glu Val Glu
                 85                  90                  95

Gly Lys Glu His Lys Glu Ser Tyr Glu Lys Leu Ile Phe Ala Thr Gly
                100                 105                 110

Ser Thr Pro Ile Leu Pro Pro Ile Glu Gly Val Glu Ile Val Lys Gly
            115                 120                 125

Asn Arg Glu Phe Lys Ala Thr Leu Glu Asn Val Gln Phe Val Lys Leu
        130                 135                 140

Tyr Gln Asn Ala Glu Glu Val Ile Asn Lys Leu Ser Asp Lys Ser Gln
145                 150                 155                 160

His Leu Asp Arg Ile Ala Val Val Gly Gly Tyr Ile Gly Val Glu
                165                 170                 175

Leu Ala Glu Ala Phe Glu Arg Leu Gly Lys Glu Val Val Leu Val Asp
            180                 185                 190

Ile Val Asp Thr Val Leu Asn Gly Tyr Tyr Asp Lys Asp Phe Thr Gln
        195                 200                 205

Met Met Ala Lys Asn Leu Glu Asp His Asn Ile Arg Leu Ala Leu Gly
    210                 215                 220

Gln Thr Val Lys Ala Ile Glu Gly Asp Gly Lys Val Glu Arg Leu Ile
225                 230                 235                 240

Thr Asp Lys Glu Ser Phe Asp Val Asp Met Val Ile Leu Ala Val Gly
                245                 250                 255

Phe Arg Pro Asn Thr Ala Leu Ala Gly Gly Lys Ile Glu Leu Phe Arg
            260                 265                 270

Asn Gly Ala Phe Leu Val Asp Lys Lys Gln Glu Thr Ser Ile Pro Asp
        275                 280                 285

Val Tyr Ala Val Gly Asp Cys Ala Thr Val Tyr Asp Asn Ala Arg Lys
    290                 295                 300

Asp Thr Ser Tyr Ile Ala Leu Ala Ser Asn Ala Val Arg Thr Gly Ile
305                 310                 315                 320

Val Gly Ala Tyr Asn Ala Cys Gly His Glu Leu Glu Gly Ile Gly Val
                325                 330                 335

Gln Gly Ser Asn Gly Ile Ser Ile Tyr Gly Leu His Met Val Ser Thr
            340                 345                 350

Gly Leu Thr Leu Glu Lys Ala Lys Ala Ala Gly Tyr Asn Ala Thr Glu
        355                 360                 365

Thr Gly Phe Asn Asp Leu Gln Lys Pro Glu Phe Met Lys His Asp Asn
    370                 375                 380

His Glu Val Ala Ile Lys Ile Val Phe Asp Lys Asp Ser Arg Glu Ile
385                 390                 395                 400

Leu Gly Ala Gln Met Val Ser His Asp Ile Ala Ile Ser Met Gly Ile
                405                 410                 415

His Met Phe Ser Leu Ala Ile Gln Glu His Val Thr Ile Asp Lys Leu
            420                 425                 430

Ala Leu Thr Asp Leu Phe Phe Leu Pro His Phe Asn Lys Pro Tyr Asn
        435                 440                 445

Tyr Ile Thr Met Ala Ala Leu Thr Ala Glu Lys
```

```
<210> SEQ ID NO 9
<211> LENGTH: 100
<212> TYPE: PRT
<213> ORGANISM: Streptococcus pneumoniae

<400> SEQUENCE: 9

Met Lys Ile Thr Gln Glu Glu Val Thr His Val Ala Asn Leu Ser Lys
1               5                   10                  15

Leu Arg Phe Ser Glu Glu Thr Ala Ala Phe Ala Thr Thr Leu Ser
            20                  25                  30

Lys Ile Val Asp Met Val Glu Leu Leu Gly Glu Val Asp Thr Thr Gly
        35                  40                  45

Val Ala Pro Thr Thr Thr Met Ala Asp Arg Lys Thr Val Leu Arg Pro
50                  55                  60

Asp Val Ala Glu Glu Gly Ile Asp Arg Asp Arg Leu Phe Lys Asn Val
65                  70                  75                  80

Pro Glu Lys Asp Asn Tyr Tyr Ile Lys Val Pro Ala Ile Leu Asp Asn
                85                  90                  95

Gly Gly Asp Ala
            100

<210> SEQ ID NO 10
<211> LENGTH: 419
<212> TYPE: PRT
<213> ORGANISM: Streptococcus pneumoniae

<400> SEQUENCE: 10

Met Thr Phe Ser Phe Asp Thr Ala Ala Ala Gln Gly Ala Val Ile Lys
1               5                   10                  15

Val Ile Gly Val Gly Gly Gly Gly Asn Ala Ile Asn Arg Met Val
            20                  25                  30

Asp Glu Gly Val Thr Gly Val Glu Phe Ile Ala Ala Asn Thr Asp Val
        35                  40                  45

Gln Ala Leu Ser Ser Thr Lys Ala Glu Thr Val Ile Gln Leu Gly Pro
50                  55                  60

Lys Leu Thr Arg Gly Leu Gly Ala Gly Gly Gln Pro Glu Val Gly Arg
65                  70                  75                  80

Lys Ala Ala Glu Glu Ser Glu Glu Thr Leu Thr Glu Ala Ile Ser Gly
                85                  90                  95

Ala Asp Met Val Phe Ile Thr Ala Gly Met Gly Gly Gly Ser Gly Thr
            100                 105                 110

Gly Ala Ala Pro Val Ile Ala Arg Ile Ala Lys Asp Leu Gly Ala Leu
        115                 120                 125

Thr Val Gly Val Val Thr Arg Pro Phe Gly Phe Glu Gly Ser Lys Arg
130                 135                 140

Gly Gln Phe Ala Val Glu Gly Ile Asn Gln Leu Arg Glu His Val Asp
145                 150                 155                 160

Thr Leu Leu Ile Ile Ser Asn Asn Asn Leu Leu Glu Ile Val Asp Lys
                165                 170                 175

Lys Thr Pro Leu Leu Glu Ala Leu Ser Glu Ala Asp Asn Val Leu Arg
            180                 185                 190

Gln Gly Val Gln Gly Ile Thr Asp Leu Ile Thr Asn Pro Gly Leu Ile
        195                 200                 205

Asn Leu Asp Phe Ala Asp Val Lys Thr Val Met Ala Asn Lys Gly Asn
210                 215                 220
```

Ala Leu Met Gly Ile Gly Ile Gly Ser Gly Glu Glu Arg Val Val Glu
225                 230                 235                 240

Ala Ala Arg Lys Ala Ile Tyr Ser Pro Leu Leu Glu Thr Thr Ile Asp
            245                 250                 255

Gly Ala Glu Asp Val Ile Val Asn Val Thr Gly Gly Leu Asp Leu Thr
        260                 265                 270

Leu Ile Glu Ala Glu Glu Ala Ser Gln Ile Val Asn Gln Ala Ala Gly
    275                 280                 285

Gln Gly Val Asn Ile Trp Leu Gly Thr Ser Ile Asp Glu Ser Met Arg
290                 295                 300

Asp Glu Ile Arg Val Thr Val Val Ala Thr Gly Val Arg Gln Asp Arg
305                 310                 315                 320

Val Glu Lys Val Val Ala Pro Gln Ala Arg Ser Ala Thr Asn Tyr Arg
            325                 330                 335

Glu Thr Val Lys Pro Ala His Ser His Gly Phe Asp Arg His Phe Asp
        340                 345                 350

Met Ala Glu Thr Val Glu Leu Pro Lys Gln Asn Pro Arg Arg Leu Glu
    355                 360                 365

Pro Thr Gln Ala Ser Ala Phe Gly Asp Trp Asp Leu Arg Arg Glu Ser
370                 375                 380

Ile Val Arg Thr Thr Asp Ser Val Val Ser Pro Val Glu Arg Phe Glu
385                 390                 395                 400

Ala Pro Ile Ser Gln Asp Glu Asp Glu Leu Asp Thr Pro Pro Phe Phe
            405                 410                 415

Lys Asn Arg

<210> SEQ ID NO 11
<211> LENGTH: 328
<212> TYPE: PRT
<213> ORGANISM: Streptococcus pneumoniae

<400> SEQUENCE: 11

Met Thr Ser Thr Lys Gln His Lys Lys Val Ile Leu Val Gly Asp Gly
1               5                   10                  15

Ala Val Gly Ser Ser Tyr Ala Phe Ala Leu Val Asn Gln Gly Ile Ala
            20                  25                  30

Gln Glu Leu Gly Ile Ile Glu Ile Pro Gln Leu His Glu Lys Ala Val
        35                  40                  45

Gly Asp Ala Leu Asp Leu Ser His Ala Leu Ala Phe Thr Ser Pro Lys
    50                  55                  60

Lys Ile Tyr Ala Ala Gln Tyr Ser Asp Cys Ala Asp Ala Asp Leu Val
65                  70                  75                  80

Val Ile Thr Ala Gly Ala Pro Gln Lys Pro Gly Glu Thr Arg Leu Asp
            85                  90                  95

Leu Val Gly Lys Asn Leu Ala Ile Asn Lys Ser Ile Val Thr Gln Val
        100                 105                 110

Val Glu Ser Gly Phe Lys Gly Ile Phe Leu Val Ala Ala Asn Pro Val
    115                 120                 125

Asp Val Leu Thr Tyr Ser Thr Trp Lys Phe Ser Gly Phe Pro Lys Glu
130                 135                 140

Arg Val Ile Gly Ser Gly Thr Ser Leu Asp Ser Ala Arg Phe Arg Gln
145                 150                 155                 160

Ala Leu Ala Glu Lys Leu Asp Val Asp Ala Arg Ser Val His Ala Tyr
            165                 170                 175

```
Ile Met Gly Glu His Gly Asp Ser Glu Phe Ala Val Trp Ser His Ala
            180                 185                 190

Asn Ile Ala Gly Val Asn Leu Glu Glu Phe Leu Lys Asp Thr Gln Asn
            195                 200                 205

Val Gln Glu Ala Glu Leu Ile Glu Leu Phe Gly Val Arg Asp Ala
    210                 215                 220

Ala Tyr Thr Ile Ile Asn Lys Lys Gly Ala Thr Tyr Tyr Gly Ile Ala
225                 230                 235                 240

Val Ala Leu Ala Arg Ile Thr Lys Ala Ile Leu Asp Asp Glu Asn Ala
            245                 250                 255

Val Leu Pro Leu Ser Val Phe Gln Glu Gly Gln Tyr Gly Val Glu Asn
            260                 265                 270

Val Phe Ile Gly Gln Pro Ala Val Gly Ala His Gly Ile Val Arg
    275                 280                 285

Pro Val Asn Ile Pro Leu Asn Asp Ala Glu Thr Gln Lys Met Gln Ala
    290                 295                 300

Ser Ala Lys Glu Leu Gln Ala Ile Ile Asp Glu Ala Trp Lys Asn Pro
305                 310                 315                 320

Glu Phe Gln Glu Ala Ser Lys Asn
                325

<210> SEQ ID NO 12
<211> LENGTH: 335
<212> TYPE: PRT
<213> ORGANISM: Streptococcus pneumoniae

<400> SEQUENCE: 12

Met Val Val Lys Val Gly Ile Asn Gly Phe Gly Arg Ile Gly Arg Leu
1               5                   10                  15

Ala Phe Arg Arg Ile Gln Asn Val Glu Gly Val Glu Val Thr Arg Ile
            20                  25                  30

Asn Asp Leu Thr Asp Pro Val Met Leu Ala His Leu Leu Lys Tyr Asp
        35                  40                  45

Thr Thr Gln Gly Arg Phe Asp Gly Thr Val Glu Val Lys Glu Gly Gly
    50                  55                  60

Phe Glu Val Asn Gly Lys Phe Ile Lys Val Ser Ala Glu Arg Asp Pro
65                  70                  75                  80

Glu Gln Ile Asp Trp Ala Thr Asp Gly Val Glu Ile Val Leu Glu Ala
                85                  90                  95

Thr Gly Phe Phe Ala Lys Lys Glu Ala Ala Glu Lys His Leu Lys Gly
            100                 105                 110

Gly Ala Lys Lys Val Val Ile Thr Ala Pro Gly Gly Asn Asp Val Lys
        115                 120                 125

Thr Val Val Phe Asn Thr Asn His Asp Val Leu Asp Gly Thr Glu Thr
    130                 135                 140

Val Ile Ser Gly Ala Ser Cys Thr Thr Asn Cys Leu Ala Pro Met Ala
145                 150                 155                 160

Lys Ala Leu Gln Asp Asn Phe Gly Val Val Glu Gly Leu Met Thr Thr
                165                 170                 175

Ile His Ala Tyr Thr Gly Asp Gln Met Ile Leu Asp Gly Pro His Arg
            180                 185                 190

Gly Gly Asp Leu Arg Arg Ala Arg Ala Gly Ala Ala Asn Ile Val Pro
        195                 200                 205

Asn Ser Thr Gly Ala Ala Lys Ala Ile Gly Leu Val Ile Pro Glu Leu
    210                 215                 220
```

```
Asn Gly Lys Leu Asp Gly Ser Ala Gln Arg Val Pro Thr Pro Thr Gly
225                 230                 235                 240

Ser Val Thr Glu Leu Val Ala Val Leu Glu Lys Asn Val Thr Val Asp
                245                 250                 255

Glu Val Asn Ala Ala Met Lys Ala Ala Ser Asn Glu Ser Tyr Gly Tyr
            260                 265                 270

Thr Glu Asp Pro Ile Val Ser Ser Asp Ile Val Gly Met Ser Tyr Gly
        275                 280                 285

Ser Leu Phe Asp Ala Thr Gln Thr Lys Val Leu Asp Val Asp Gly Lys
    290                 295                 300

Gln Leu Val Lys Val Ser Trp Tyr Asp Asn Glu Met Ser Tyr Thr
305                 310                 315                 320

Ala Gln Leu Val Arg Thr Leu Glu Tyr Phe Ala Lys Ile Ala Lys
                325                 330                 335

<210> SEQ ID NO 13
<211> LENGTH: 293
<212> TYPE: PRT
<213> ORGANISM: Streptococcus pneumoniae

<400> SEQUENCE: 13

Met Ala Ile Val Ser Ala Glu Lys Phe Val Gln Ala Ala Arg Asp Asn
1               5                   10                  15

Gly Tyr Ala Val Gly Gly Phe Asn Thr Asn Asn Leu Glu Trp Thr Gln
            20                  25                  30

Ala Ile Leu Arg Ala Ala Glu Ala Lys Lys Ala Pro Val Leu Ile Gln
        35                  40                  45

Thr Ser Met Gly Ala Ala Lys Tyr Met Gly Gly Tyr Lys Val Ala Arg
    50                  55                  60

Asn Leu Ile Ala Asn Leu Val Glu Ser Met Gly Ile Thr Val Pro Val
65              70                  75                  80

Ala Ile His Leu Asp His Gly His Tyr Glu Asp Ala Leu Glu Cys Ile
                85                  90                  95

Glu Val Gly Tyr Thr Ser Ile Met Phe Asp Gly Ser His Leu Pro Val
            100                 105                 110

Glu Glu Asn Leu Lys Leu Ala Lys Glu Val Val Glu Lys Ala His Ala
        115                 120                 125

Lys Gly Ile Ser Val Glu Ala Glu Val Gly Thr Ile Gly Gly Glu Glu
    130                 135                 140

Asp Gly Ile Ile Gly Lys Gly Glu Leu Ala Pro Ile Glu Asp Ala Lys
145                 150                 155                 160

Ala Met Val Glu Thr Gly Ile Asp Phe Leu Ala Ala Gly Ile Gly Asn
                165                 170                 175

Ile His Gly Pro Tyr Pro Val Asn Trp Glu Gly Leu Asp Leu Asp His
            180                 185                 190

Leu Gln Lys Leu Thr Glu Ala Leu Pro Gly Phe Pro Ile Val Leu His
        195                 200                 205

Gly Gly Ser Gly Ile Pro Asp Glu Gln Ile Gln Ala Ala Ile Lys Leu
    210                 215                 220

Gly Val Ala Lys Val Asn Val Asn Thr Glu Cys Gln Ile Ala Phe Ala
225                 230                 235                 240

Asn Ala Thr Arg Lys Phe Ala Arg Asp Tyr Glu Ala Asn Glu Ala Glu
                245                 250                 255

Tyr Asp Lys Lys Lys Leu Phe Asp Pro Arg Lys Phe Leu Ala Asp Gly
            260                 265                 270
```

```
Val Lys Ala Ile Gln Ala Ser Val Glu Glu Arg Ile Asp Val Phe Gly
        275                 280                 285

Ser Glu Gly Lys Ala
    290
```

<210> SEQ ID NO 14
<211> LENGTH: 336
<212> TYPE: PRT
<213> ORGANISM: Streptococcus pneumoniae

<400> SEQUENCE: 14

```
Met Ala Ile Leu Val Thr Gly Gly Ala Gly Tyr Ile Gly Ser His Thr
1               5                   10                  15

Val Val Glu Leu Leu Asn Leu Gly Lys Glu Val Ile Ile Val Asp Asn
            20                  25                  30

Leu Ser Asn Ser Ser Ile Leu Val Leu Asp Arg Ile Glu Ala Ile Thr
        35                  40                  45

Gly Ile Arg Pro Val Phe Tyr Glu Leu Asp Val Cys Asp Lys Gln Ala
    50                  55                  60

Leu Arg Lys Val Phe Glu Gln Glu Ser Ile Asp Ala Ala Ile His Phe
65                  70                  75                  80

Ala Gly Tyr Lys Ala Val Gly Glu Ser Val Gln Lys Pro Val Met Tyr
                85                  90                  95

Tyr Lys Asn Asn Ile Met Ser Thr Leu Ala Leu Val Glu Val Met Ser
            100                 105                 110

Glu Phe Asn Val Lys Lys Ile Val Phe Ser Ser Ala Thr Val Tyr
        115                 120                 125

Gly Ile Asn Asn Gln Ser Pro Leu Ile Glu Thr Met Gln Thr Ser Ala
    130                 135                 140

Thr Asn Pro Tyr Gly Tyr Thr Lys Val Met Leu Glu Gln Ile Leu Lys
145                 150                 155                 160

Asp Val His Val Ala Asp Ser Glu Trp Ser Ile Ala Leu Leu Arg Tyr
                165                 170                 175

Phe Asn Pro Ile Gly Ala His Glu Ser Gly Leu Ile Gly Glu Asp Pro
            180                 185                 190

Ser Gly Ile Pro Asn Asn Leu Met Pro Tyr Ile Ala Gln Val Ala Val
        195                 200                 205

Gly Lys Leu Ser Glu Leu Ser Val Phe Gly Asn Asp Tyr Asp Thr Leu
    210                 215                 220

Asp Gly Thr Gly Val Arg Asp Tyr Ile His Val Val Asp Leu Ala Ile
225                 230                 235                 240

Gly His Ile Lys Ala Leu Glu Lys Val Ser Glu Lys Thr Asp Val Tyr
                245                 250                 255

Ile Tyr Asn Leu Gly Ser Gly Glu Gly Thr Ser Val Leu Gln Leu Val
            260                 265                 270

Asn Thr Phe Glu Ser Val Asn Lys Ile Pro Ile Pro Tyr Lys Ile Val
        275                 280                 285

Pro Arg Arg Ser Gly Asp Val Ala Thr Cys Tyr Ala Asn Ala Asp Lys
    290                 295                 300

Ala Tyr Lys Glu Leu Asn Trp Arg Thr Thr Lys Ser Ile Glu Asp Met
305                 310                 315                 320

Cys Arg Asp Thr Trp Asn Trp Gln Ser Lys Asn Pro Asn Gly Tyr Asn
                325                 330                 335
```

<210> SEQ ID NO 15
<211> LENGTH: 620

<212> TYPE: PRT
<213> ORGANISM: Streptococcus pneumoniae

<400> SEQUENCE: 15

Met Asn Ile Ile Glu Glu Ile Met Thr Lys Leu Arg Glu Asp Ile Arg
1               5                   10                  15

Asn Ile Ala Ile Ile Ala His Val Asp His Gly Lys Thr Thr Leu Val
            20                  25                  30

Asp Glu Leu Leu Lys Gln Ser Glu Thr Leu Asp Ala Arg Thr Glu Leu
        35                  40                  45

Ala Glu Arg Ala Met Asp Ser Asn Asp Ile Glu Lys Glu Arg Gly Ile
    50                  55                  60

Thr Ile Leu Ala Lys Asn Thr Ala Val Ala Tyr Asn Gly Thr Arg Ile
65                  70                  75                  80

Asn Ile Met Asp Thr Pro Gly His Ala Asp Phe Gly Gly Glu Val Glu
                85                  90                  95

Arg Ile Met Lys Met Val Asp Gly Val Val Leu Val Val Asp Ala Tyr
            100                 105                 110

Glu Gly Thr Met Pro Gln Thr Arg Phe Val Leu Lys Lys Ala Leu Glu
        115                 120                 125

Gln Asp Leu Val Pro Ile Val Val Asn Lys Ile Asp Lys Pro Ser
    130                 135                 140

Ala Arg Pro Ala Glu Val Val Asp Glu Val Leu Glu Leu Phe Ile Glu
145                 150                 155                 160

Leu Gly Ala Asp Asp Gln Leu Asp Phe Pro Val Val Tyr Ala Ser
                165                 170                 175

Ala Ile Asn Gly Thr Ser Ser Leu Ser Asp Asp Pro Ala Asp Gln Glu
            180                 185                 190

Ala Thr Met Ala Pro Ile Phe Asp Thr Ile Ile Asp His Ile Pro Ala
        195                 200                 205

Pro Val Asp Asn Ser Asp Glu Pro Leu Gln Phe Gln Val Ser Leu Leu
    210                 215                 220

Asp Tyr Asn Asp Phe Val Gly Arg Ile Gly Ile Gly Arg Val Phe Arg
225                 230                 235                 240

Gly Thr Val Lys Val Gly Asp Gln Val Thr Leu Ser Lys Leu Asp Gly
                245                 250                 255

Thr Thr Lys Asn Phe Arg Val Thr Lys Leu Phe Gly Phe Gly Leu
            260                 265                 270

Glu Arg Arg Glu Ile Gln Glu Ala Lys Ala Gly Asp Leu Ile Ala Val
        275                 280                 285

Ser Gly Met Glu Asp Ile Phe Val Gly Glu Thr Ile Thr Pro Thr Asp
    290                 295                 300

Ala Val Glu Ala Leu Pro Ile Leu His Ile Asp Glu Pro Thr Leu Gln
305                 310                 315                 320

Met Thr Phe Leu Val Asn Asn Ser Pro Phe Ala Gly Lys Glu Gly Lys
                325                 330                 335

Trp Val Thr Ser Arg Lys Val Glu Glu Arg Leu Gln Ala Glu Leu Gln
            340                 345                 350

Thr Asp Val Ser Leu Arg Val Asp Pro Thr Asp Ser Pro Asp Lys Trp
        355                 360                 365

Thr Val Ser Gly Arg Gly Glu Leu His Leu Ser Ile Leu Ile Glu Thr
    370                 375                 380

Met Arg Arg Glu Gly Tyr Glu Leu Gln Val Ser Arg Pro Glu Val Ile
385                 390                 395                 400

```
Val Lys Glu Ile Asp Gly Val Lys Cys Glu Pro Phe Glu Arg Val Gln
                405                 410                 415

Ile Asp Thr Pro Glu Glu Tyr Gln Gly Ser Val Ile Gln Ser Leu Ser
            420                 425                 430

Glu Arg Lys Gly Glu Met Leu Asp Met Ile Ser Thr Gly Asn Gly Gln
        435                 440                 445

Thr Arg Leu Val Phe Leu Val Pro Ala Arg Gly Leu Ile Gly Tyr Ser
    450                 455                 460

Thr Glu Phe Leu Ser Met Thr Arg Gly Tyr Gly Ile Met Asn His Thr
465                 470                 475                 480

Phe Asp Gln Tyr Leu Pro Leu Ile Pro Gly Glu Ile Gly Arg His
                485                 490                 495

Arg Gly Ala Leu Val Ser Ile Asp Ala Gly Lys Ala Thr Thr Tyr Ser
            500                 505                 510

Ile Met Ser Ile Glu Glu Arg Gly Thr Ile Phe Val Asn Pro Gly Thr
        515                 520                 525

Glu Val Tyr Glu Gly Met Ile Ile Gly Glu Asn Ser Arg Glu Asn Asp
    530                 535                 540

Leu Thr Val Asn Ile Thr Lys Ala Lys Gln Met Thr Asn Val Arg Ser
545                 550                 555                 560

Ala Thr Lys Asp Gln Thr Ala Val Ile Lys Thr Pro Arg Ile Leu Thr
                565                 570                 575

Leu Glu Glu Ser Leu Glu Phe Leu Asn Asp Asp Glu Tyr Met Glu Val
            580                 585                 590

Thr Pro Glu Ser Ile Arg Leu Arg Lys Gln Ile Leu Asn Lys Ala Glu
        595                 600                 605

Arg Glu Lys Ala Asn Lys Lys Lys Ser Ala Glu
    610                 615                 620

<210> SEQ ID NO 16
<211> LENGTH: 520
<212> TYPE: PRT
<213> ORGANISM: Streptococcus pneumoniae

<400> SEQUENCE: 16

Met Ser Asn Ile Ser Thr Asp Leu Gln Asp Val Glu Lys Ile Ile Val
1               5                   10                  15

Leu Asp Tyr Gly Ser Gln Tyr Asn Gln Leu Ile Ser Arg Ile Arg
            20                  25                  30

Glu Ile Gly Val Phe Ser Glu Leu Lys Ser His Lys Ile Ser Ala Ala
        35                  40                  45

Glu Val Arg Glu Val Asn Pro Val Gly Ile Ile Leu Ser Gly Gly Pro
    50                  55                  60

Asn Ser Val Tyr Glu Asp Gly Ser Phe Asp Ile Asp Pro Glu Ile Phe
65                  70                  75                  80

Glu Leu Gly Ile Pro Ile Leu Gly Ile Cys Tyr Gly Met Gln Leu Leu
                85                  90                  95

Thr His Lys Leu Gly Gly Lys Val Val Pro Ala Gly Asp Ala Gly Asn
            100                 105                 110

Arg Glu Tyr Gly Gln Ser Thr Leu Thr His Thr Pro Ser Ala Leu Phe
        115                 120                 125

Glu Ser Thr Pro Asp Glu Gln Thr Val Leu Met Ser His Gly Asp Ala
    130                 135                 140

Val Thr Glu Ile Pro Ala Asp Phe Val Arg Thr Gly Thr Ser Ala Asp
145                 150                 155                 160
```

```
Cys Pro Tyr Ala Ala Ile Glu Asn Pro Asp Lys His Ile Tyr Gly Ile
                165                 170                 175

Gln Phe His Pro Glu Val Arg His Ser Val Tyr Gly Asn Asp Ile Leu
            180                 185                 190

Arg Asn Phe Ala Leu Asn Ile Cys Lys Ala Lys Gly Asp Trp Ser Met
        195                 200                 205

Asp Asn Phe Ile Asp Met Gln Ile Lys Ile Arg Glu Thr Val Gly
    210                 215                 220

Asp Lys Arg Val Leu Leu Gly Leu Ser Gly Gly Val Asp Ser Val
225                 230                 235                 240

Val Gly Val Leu Leu Gln Lys Ala Ile Gly Asp Gln Leu Ile Cys Ile
                245                 250                 255

Phe Val Asp His Gly Leu Leu Arg Lys Gly Glu Ala Asp Gln Val Met
            260                 265                 270

Asp Met Leu Gly Gly Lys Phe Gly Leu Asn Ile Val Lys Ala Asp Ala
        275                 280                 285

Ala Lys Arg Phe Leu Asp Lys Leu Ala Gly Val Ser Asp Pro Glu Gln
    290                 295                 300

Lys Arg Lys Ile Ile Gly Asn Glu Phe Val Tyr Val Phe Asp Asp Glu
305                 310                 315                 320

Ala Ser Lys Leu Lys Asp Val Lys Phe Leu Ala Gln Gly Thr Leu Tyr
                325                 330                 335

Thr Asp Val Ile Glu Ser Gly Thr Asp Thr Ala Gln Thr Ile Lys Ser
            340                 345                 350

His His Asn Val Gly Gly Leu Pro Glu Asp Met Gln Phe Glu Leu Ile
        355                 360                 365

Glu Pro Leu Asn Thr Leu Tyr Lys Asp Glu Val Arg Ala Leu Gly Thr
    370                 375                 380

Glu Leu Gly Met Pro Asp His Ile Val Trp Arg Gln Pro Phe Pro Gly
385                 390                 395                 400

Pro Gly Leu Ala Ile Arg Val Met Gly Glu Ile Thr Glu Glu Lys Leu
                405                 410                 415

Glu Thr Val Arg Glu Ser Asp Ala Ile Leu Arg Glu Gly Ile Ala Lys
            420                 425                 430

Ala Gly Leu Asp Arg Asp Ile Trp Gln Tyr Phe Thr Val Asn Thr Gly
        435                 440                 445

Val Arg Ser Val Gly Val Met Gly Asp Gly Arg Thr Tyr Asp Tyr Thr
    450                 455                 460

Ile Ala Ile Arg Ala Ile Thr Ser Ile Asp Gly Met Thr Ala Asp Phe
465                 470                 475                 480

Ala Lys Ile Pro Trp Glu Val Leu Gln Lys Ile Ser Val Arg Ile Val
                485                 490                 495

Asn Glu Val Asp His Val Asn Arg Ile Val Tyr Asp Ile Thr Ser Lys
            500                 505                 510

Pro Pro Ala Thr Val Glu Trp Glu
        515                 520

<210> SEQ ID NO 17
<211> LENGTH: 486
<212> TYPE: PRT
<213> ORGANISM: Streptococcus pneumoniae

<400> SEQUENCE: 17

Met Ser Lys Asp Ile Arg Val Arg Tyr Ala Pro Ser Pro Thr Gly Leu
1               5                   10                  15
```

```
Leu His Ile Gly Asn Ala Arg Thr Ala Leu Phe Asn Tyr Leu Tyr Ala
         20                  25                  30

Arg His His Gly Gly Thr Phe Leu Ile Arg Ile Glu Asp Thr Asp Arg
         35                  40                  45

Lys Arg His Val Glu Asp Gly Glu Arg Ser Gln Leu Glu Asn Leu Arg
 50                  55                  60

Trp Leu Gly Met Asp Trp Asp Glu Ser Pro Glu Ser His Glu Asn Tyr
 65                  70                  75                  80

Arg Gln Ser Glu Arg Leu Asp Leu Tyr Gln Lys Tyr Ile Asp Gln Leu
             85                  90                  95

Leu Ala Glu Gly Lys Ala Tyr Lys Ser Tyr Val Thr Glu Glu Leu
         100                 105                 110

Ala Ala Glu Arg Glu Arg Gln Glu Val Ala Gly Glu Thr Pro Arg Tyr
         115                 120                 125

Ile Asn Glu Tyr Leu Gly Met Ser Glu Glu Lys Ala Ala Tyr Ile
         130                 135                 140

Ala Glu Arg Glu Ala Ala Gly Ile Ile Pro Thr Val Arg Leu Ala Val
145                 150                 155                 160

Asn Glu Ser Gly Ile Tyr Lys Trp His Asp Met Val Lys Gly Asp Ile
                 165                 170                 175

Glu Phe Glu Gly Gly Asn Ile Gly Gly Asp Trp Val Ile Gln Lys Lys
             180                 185                 190

Asp Gly Tyr Pro Thr Tyr Asn Phe Ala Val Val Ile Asp Asp His Asp
         195                 200                 205

Met Gln Ile Ser His Val Ile Arg Gly Asp Asp His Ile Ala Asn Thr
210                 215                 220

Pro Lys Gln Leu Met Val Tyr Glu Ala Leu Gly Trp Glu Ala Pro Glu
225                 230                 235                 240

Phe Gly His Met Thr Leu Ile Ile Asn Ser Glu Thr Gly Lys Lys Leu
                 245                 250                 255

Ser Lys Arg Asp Thr Asn Thr Leu Gln Phe Ile Glu Asp Tyr Arg Lys
             260                 265                 270

Lys Gly Tyr Leu Pro Glu Ala Val Phe Asn Phe Ile Ala Leu Leu Gly
         275                 280                 285

Trp Asn Pro Gly Gly Glu Asp Glu Ile Phe Ser Arg Glu Glu Phe Ile
         290                 295                 300

Lys Leu Phe Asp Glu Asn Arg Leu Ser Lys Ser Pro Ala Ala Phe Asp
305                 310                 315                 320

Gln Lys Lys Leu Asp Trp Met Ser Asn Asp Tyr Ile Lys Asn Ala Asp
                 325                 330                 335

Leu Glu Thr Ile Phe Glu Met Ala Lys Pro Phe Leu Glu Glu Ala Gly
             340                 345                 350

Arg Leu Thr Asp Lys Ala Glu Lys Leu Val Glu Leu Tyr Lys Pro Gln
         355                 360                 365

Met Lys Ser Val Asp Glu Ile Ile Pro Leu Thr Asp Leu Phe Phe Ser
         370                 375                 380

Asp Phe Pro Glu Leu Thr Glu Ala Glu Arg Glu Val Met Thr Gly Glu
385                 390                 395                 400

Thr Val Pro Thr Val Leu Glu Ala Phe Lys Ala Lys Leu Glu Ala Met
                 405                 410                 415

Thr Asp Asp Glu Phe Val Thr Glu Asn Ile Phe Pro Gln Ile Lys Ala
             420                 425                 430

Val Gln Lys Glu Thr Gly Ile Lys Gly Lys Asn Leu Phe Met Pro Ile
         435                 440                 445
```

Arg Ile Ala Val Ser Gly Glu Met His Gly Pro Glu Leu Pro Asp Thr
    450                 455                 460

Ile Phe Leu Leu Gly Arg Glu Lys Ser Ile Gln His Ile Glu Asn Met
465                 470                 475                 480

Leu Lys Glu Ile Ser Lys
                485

<210> SEQ ID NO 18
<211> LENGTH: 448
<212> TYPE: PRT
<213> ORGANISM: Streptococcus pneumoniae

<400> SEQUENCE: 18

Met Thr Ser Ala Lys Glu Tyr Ile Gln Ser Val Phe Glu Thr Val Lys
1               5                   10                  15

Ala Arg Asn Gly His Glu Ala Glu Phe Leu Gln Ala Val Glu Glu Phe
            20                  25                  30

Phe Asn Thr Leu Glu Pro Val Phe Glu Lys His Pro Glu Tyr Ile Glu
        35                  40                  45

Glu Asn Ile Leu Ala Arg Ile Thr Glu Pro Arg Val Val Ser Phe
    50                  55                  60

Arg Val Pro Trp Val Asp Arg Asp Gly Lys Ile Gln Val Asn Arg Gly
65                  70                  75                  80

Tyr Arg Val Gln Phe Asn Ser Ala Val Gly Pro Tyr Lys Gly Gly Leu
                85                  90                  95

Arg Phe His Pro Thr Val Asn Gln Gly Ile Leu Lys Phe Leu Gly Phe
            100                 105                 110

Glu Gln Ile Phe Lys Asn Val Leu Thr Gly Leu Pro Ile Gly Gly Gly
        115                 120                 125

Lys Gly Gly Ser Asp Phe Asp Pro Lys Gly Lys Thr Asp Ala Glu Val
130                 135                 140

Met Arg Phe Cys Gln Ser Phe Met Thr Glu Leu Gln Lys His Ile Gly
145                 150                 155                 160

Pro Ser Leu Asp Val Pro Ala Gly Asp Ile Gly Val Gly Gly Arg Glu
                165                 170                 175

Ile Gly Tyr Leu Tyr Gly Gln Tyr Lys Arg Leu Asn Gln Phe Asp Ala
            180                 185                 190

Gly Val Leu Thr Gly Lys Pro Leu Gly Phe Gly Gly Ser Leu Ile Arg
        195                 200                 205

Pro Glu Ala Thr Gly Tyr Gly Leu Val Tyr Tyr Thr Glu Glu Met Leu
210                 215                 220

Lys Ala Asn Gly Asn Ser Phe Ala Gly Lys Lys Val Val Ile Ser Gly
225                 230                 235                 240

Ser Gly Asn Val Ala Gln Tyr Ala Leu Gln Lys Ala Thr Glu Leu Gly
                245                 250                 255

Ala Thr Val Ile Ser Val Ser Asp Ser Asn Gly Tyr Val Ile Asp Glu
            260                 265                 270

Asn Gly Ile Asp Phe Asp Leu Leu Val Asp Val Lys Glu Lys Arg Arg
        275                 280                 285

Ala Arg Leu Thr Glu Tyr Ala Ala Glu Lys Ala Thr Ala Tyr His
290                 295                 300

Glu Gly Thr Val Trp Thr Tyr Ala Gly Asn Tyr Asp Ile Ala Leu Pro
305                 310                 315                 320

Cys Ala Thr Gln Asn Glu Ile Asn Gly Glu Ala Ala Lys Arg Leu Val
                325                 330                 335

```
Ala Gln Gly Val Ile Cys Val Ser Glu Gly Ala Asn Met Pro Ser Asp
                340                 345                 350

Leu Asp Ala Ile Lys Val Tyr Lys Glu Asn Gly Ile Phe Tyr Gly Pro
                355                 360                 365

Ala Lys Ala Ala Asn Ala Gly Gly Val Ala Val Ser Ala Leu Glu Met
            370                 375                 380

Ser Gln Asn Ser Leu Arg Leu Ser Trp Thr Arg Glu Glu Val Asp Gly
385                 390                 395                 400

Arg Leu Lys Asp Ile Met Thr Asn Ile Phe Asn Thr Ala Lys Thr Thr
                405                 410                 415

Ser Glu Thr Tyr Gly Leu Asp Lys Asp Tyr Leu Ala Gly Ala Asn Ile
                420                 425                 430

Ala Ala Phe Glu Asn Val Ala Asn Ala Met Ile Ala Gln Gly Ile Val
            435                 440                 445

<210> SEQ ID NO 19
<211> LENGTH: 346
<212> TYPE: PRT
<213> ORGANISM: Streptococcus pneumoniae

<400> SEQUENCE: 19

Met Ala Glu Ile Thr Ala Lys Leu Val Lys Glu Leu Arg Glu Lys Ser
1               5                   10                  15

Gly Ala Gly Val Met Asp Ala Lys Ala Leu Val Glu Thr Asp Gly
                20                  25                  30

Asp Ile Glu Lys Ala Ile Glu Leu Leu Arg Glu Lys Gly Met Ala Lys
                35                  40                  45

Ala Ala Lys Lys Ala Asp Arg Val Ala Ala Glu Gly Leu Thr Gly Val
            50                  55                  60

Tyr Val Asn Gly Asn Val Ala Ala Val Ile Glu Val Asn Ala Glu Thr
65                  70                  75                  80

Asp Phe Val Ala Lys Asn Ala Gln Phe Val Glu Leu Val Asn Thr Thr
                85                  90                  95

Ala Lys Val Ile Ala Glu Gly Lys Pro Ala Asn Asn Glu Glu Ala Leu
                100                 105                 110

Ala Leu Ile Met Pro Ser Gly Glu Thr Leu Glu Ala Ala Tyr Val Ser
                115                 120                 125

Ala Thr Ala Thr Ile Gly Glu Lys Ile Ser Phe Arg Arg Phe Ala Leu
            130                 135                 140

Ile Glu Lys Thr Asp Ala Gln His Phe Gly Ala Tyr Gln His Asn Gly
145                 150                 155                 160

Gly Arg Ile Gly Val Ile Ser Val Val Glu Gly Gly Asp Glu Ala Leu
                165                 170                 175

Ala Lys Gln Leu Ser Met His Ile Ala Ala Met Lys Pro Thr Val Leu
                180                 185                 190

Ser Tyr Lys Glu Leu Asp Glu Gln Phe Val Lys Asp Glu Leu Ala Gln
            195                 200                 205

Leu Asn His Val Ile Asp Gln Asp Asn Glu Ser Arg Ala Met Val Asn
210                 215                 220

Lys Pro Ala Leu Pro His Leu Lys Tyr Gly Ser Lys Ala Gln Leu Thr
225                 230                 235                 240

Asp Asp Val Ile Ala Gln Ala Glu Ala Asp Ile Lys Ala Glu Leu Ala
                245                 250                 255

Ala Glu Gly Lys Pro Glu Lys Ile Trp Asp Lys Ile Ile Pro Gly Lys
                260                 265                 270
```

```
Met Asp Arg Phe Met Leu Asp Asn Thr Lys Val Asp Gln Ala Tyr Thr
            275                 280                 285

Leu Leu Ala Gln Val Tyr Ile Met Asp Asp Ser Lys Thr Val Glu Ala
            290                 295                 300

Tyr Leu Glu Ser Val Asn Ala Ser Val Val Glu Phe Ala Arg Phe Glu
305                 310                 315                 320

Val Gly Glu Gly Ile Glu Lys Ala Ala Asn Asp Phe Glu Ala Glu Val
                    325                 330                 335

Ala Ala Thr Met Ala Ala Ala Leu Asn Asn
            340                 345

<210> SEQ ID NO 20
<211> LENGTH: 398
<212> TYPE: PRT
<213> ORGANISM: Streptococcus pneumoniae

<400> SEQUENCE: 20

Met Ala Lys Leu Thr Val Lys Asp Val Asp Leu Lys Gly Lys Lys Val
1               5                   10                  15

Leu Val Arg Val Asp Phe Asn Val Pro Leu Lys Asp Gly Val Ile Thr
            20                  25                  30

Asn Asp Asn Arg Ile Thr Ala Ala Leu Pro Thr Ile Lys Tyr Ile Ile
            35                  40                  45

Glu Gln Gly Gly Arg Ala Ile Leu Phe Ser His Leu Gly Arg Val Lys
        50                  55                  60

Glu Glu Ala Asp Lys Ala Gly Lys Ser Leu Ala Pro Val Ala Ala Asp
65                  70                  75                  80

Leu Ala Ala Lys Leu Gly Gln Asp Val Val Phe Pro Gly Val Thr Arg
                85                  90                  95

Gly Ala Glu Leu Glu Ala Ala Ile Asn Ala Leu Glu Asp Gly Gln Val
            100                 105                 110

Leu Leu Val Glu Asn Thr Arg Tyr Glu Asp Val Asp Gly Lys Lys Glu
            115                 120                 125

Ser Lys Asn Asp Pro Glu Leu Gly Lys Tyr Trp Ala Ser Leu Gly Asp
        130                 135                 140

Gly Ile Phe Val Asn Asp Ala Phe Gly Thr Ala His Arg Ala His Ala
145                 150                 155                 160

Ser Asn Val Gly Ile Ser Ala Asn Val Glu Lys Ala Val Ala Gly Phe
                165                 170                 175

Leu Leu Glu Asn Glu Ile Ala Tyr Ile Gln Glu Ala Val Glu Thr Pro
            180                 185                 190

Glu Arg Pro Phe Val Ala Ile Leu Gly Gly Ser Lys Val Ser Asp Lys
            195                 200                 205

Ile Gly Val Ile Glu Asn Leu Leu Glu Lys Ala Asp Asn Val Leu Ile
        210                 215                 220

Gly Gly Gly Met Thr Tyr Thr Phe Tyr Lys Ala Gln Gly Ile Glu Ile
225                 230                 235                 240

Gly Asn Ser Leu Val Glu Glu Asp Lys Leu Asp Val Ala Lys Ala Leu
                245                 250                 255

Leu Glu Lys Ala Asn Gly Lys Leu Ile Leu Pro Val Asp Ser Lys Glu
            260                 265                 270

Ala Asn Ala Phe Ala Gly Tyr Thr Glu Val Arg Asp Thr Glu Gly Glu
            275                 280                 285

Ala Val Ser Glu Gly Phe Leu Gly Leu Asp Ile Gly Pro Lys Ser Ile
        290                 295                 300
```

```
Ala Lys Phe Asp Glu Ala Leu Thr Gly Ala Lys Thr Val Val Trp Asn
305                 310                 315                 320

Gly Pro Met Gly Val Phe Glu Asn Pro Asp Phe Gln Ala Gly Thr Ile
            325                 330                 335

Gly Val Met Asp Ala Ile Val Lys Gln Pro Gly Val Lys Ser Ile Ile
            340                 345                 350

Gly Gly Gly Asp Ser Ala Ala Ala Ile Asn Leu Gly Arg Ala Asp
        355                 360                 365

Lys Phe Ser Trp Ile Ser Thr Gly Gly Ala Ser Met Glu Leu Leu
    370                 375                 380

Glu Gly Lys Val Leu Pro Gly Leu Ala Ala Leu Thr Glu Lys
385                 390                 395

<210> SEQ ID NO 21
<211> LENGTH: 400
<212> TYPE: PRT
<213> ORGANISM: Streptococcus pneumoniae

<400> SEQUENCE: 21

Met Asn Glu Phe Glu Asp Leu Leu Asn Ser Val Ser Gln Val Glu Thr
1               5                   10                  15

Gly Asp Val Val Ser Ala Glu Val Leu Thr Val Asp Ala Thr Gln Ala
            20                  25                  30

Asn Val Ala Ile Ser Gly Thr Gly Val Glu Gly Val Leu Thr Leu Arg
        35                  40                  45

Glu Leu Thr Asn Asp Arg Asp Ala Asp Ile Asn Asp Phe Val Lys Val
    50                  55                  60

Gly Glu Val Leu Asp Val Leu Val Leu Arg Gln Val Val Gly Lys Asp
65                  70                  75                  80

Thr Asp Thr Val Thr Tyr Leu Val Ser Lys Lys Arg Leu Glu Ala Arg
                85                  90                  95

Lys Ala Trp Asp Lys Leu Val Gly Arg Glu Glu Val Val Thr Val
            100                 105                 110

Lys Gly Thr Arg Ala Val Lys Gly Gly Leu Ser Val Glu Phe Glu Gly
            115                 120                 125

Val Arg Gly Phe Ile Pro Ala Ser Met Leu Asp Thr Arg Phe Val Arg
130                 135                 140

Asn Ala Glu Arg Phe Val Gly Gln Glu Phe Asp Thr Lys Ile Lys Glu
145                 150                 155                 160

Val Asn Ala Lys Glu Asn Arg Phe Ile Leu Ser Arg Arg Glu Val Val
                165                 170                 175

Glu Ala Ala Thr Ala Ala Ala Arg Ala Glu Val Phe Gly Lys Leu Ala
            180                 185                 190

Val Gly Asp Val Val Thr Gly Lys Val Ala Arg Ile Thr Ser Phe Gly
        195                 200                 205

Ala Phe Val Asp Leu Gly Gly Val Asp Gly Leu Val His Leu Thr Glu
    210                 215                 220

Leu Ser His Glu Arg Asn Val Ser Pro Lys Ser Val Thr Val Gly
225                 230                 235                 240

Glu Glu Ile Glu Val Lys Ile Leu Asp Leu Asn Glu Glu Glu Gly Arg
                245                 250                 255

Val Ser Leu Ser Leu Lys Ala Thr Val Pro Gly Pro Trp Asp Gly Val
            260                 265                 270

Glu Gln Lys Leu Ala Lys Gly Asp Val Val Glu Gly Thr Val Lys Arg
        275                 280                 285
```

```
Leu Thr Asp Phe Gly Ala Phe Val Glu Val Leu Pro Gly Ile Asp Gly
        290                 295                 300

Leu Val His Val Ser Gln Ile Ser His Lys Arg Ile Glu Asn Pro Lys
305                 310                 315                 320

Glu Ala Leu Lys Val Gly Gln Glu Val Gln Val Lys Val Leu Glu Val
                325                 330                 335

Asn Ala Asp Ala Glu Arg Val Ser Leu Ser Ile Lys Ala Leu Glu Glu
            340                 345                 350

Arg Pro Ala Gln Glu Glu Gly Gln Lys Glu Lys Arg Ala Ala Arg
        355                 360                 365

Pro Arg Arg Pro Arg Arg Gln Glu Lys Arg Asp Phe Glu Leu Pro Glu
    370                 375                 380

Thr Gln Thr Gly Phe Ser Met Ala Asp Leu Phe Gly Asp Ile Glu Leu
385                 390                 395                 400

<210> SEQ ID NO 22
<211> LENGTH: 474
<212> TYPE: PRT
<213> ORGANISM: Streptococcus pneumoniae

<400> SEQUENCE: 22

Met Thr Lys Ala Asn Phe Gly Val Val Gly Met Ala Val Met Gly Arg
1               5                   10                  15

Asn Leu Ala Leu Asn Ile Glu Ser Arg Gly Tyr Thr Val Ala Ile Tyr
            20                  25                  30

Asn Arg Ser Lys Glu Lys Thr Glu Asp Val Ile Ala Cys His Pro Glu
        35                  40                  45

Lys Asn Phe Val Pro Ser Tyr Asp Val Glu Ser Phe Val Asn Ser Ile
50                  55                  60

Glu Lys Pro Arg Arg Ile Met Leu Met Val Gln Ala Gly Pro Gly Thr
65                  70                  75                  80

Asp Ala Thr Ile Gln Ala Leu Leu Pro His Leu Asp Lys Gly Asp Ile
                85                  90                  95

Leu Ile Asp Gly Gly Asn Thr Phe Tyr Lys Asp Thr Ile Arg Arg Asn
            100                 105                 110

Glu Glu Leu Ala Asn Ser Gly Ile Asn Phe Ile Gly Thr Gly Val Ser
        115                 120                 125

Gly Gly Glu Lys Gly Ala Leu Glu Gly Pro Ser Ile Met Pro Gly Gly
    130                 135                 140

Gln Lys Glu Ala Tyr Glu Leu Val Ala Asp Val Leu Glu Glu Ile Ser
145                 150                 155                 160

Ala Lys Ala Pro Glu Asp Gly Lys Pro Cys Val Thr Tyr Ile Gly Pro
                165                 170                 175

Asp Gly Ala Gly His Tyr Val Lys Met Val His Asn Gly Ile Glu Tyr
            180                 185                 190

Gly Asp Met Gln Leu Ile Ala Glu Ser Tyr Asp Leu Met Gln His Leu
        195                 200                 205

Leu Gly Leu Ser Ala Glu Asp Met Ala Glu Ile Phe Thr Glu Trp Asn
    210                 215                 220

Lys Gly Glu Leu Asp Ser Tyr Leu Ile Glu Ile Thr Ala Asp Ile Leu
225                 230                 235                 240

Ser Arg Lys Asp Asp Glu Gly Gln Asp Gly Pro Ile Val Asp Tyr Ile
                245                 250                 255

Leu Asp Ala Ala Gly Asn Lys Gly Thr Gly Lys Trp Thr Ser Gln Ser
            260                 265                 270
```

Ser Leu Asp Leu Gly Val Pro Leu Ser Leu Ile Thr Glu Ser Val Phe
        275                 280                 285

Ala Arg Tyr Ile Ser Thr Tyr Lys Glu Glu Arg Val His Ala Ser Lys
        290                 295                 300

Val Leu Pro Lys Pro Ala Phe Asn Phe Glu Gly Asp Lys Ala Glu
305                 310                 315                 320

Leu Ile Glu Lys Ile Arg Gln Ala Leu Tyr Phe Ser Lys Ile Ile Ser
                325                 330                 335

Tyr Ala Gln Gly Phe Ala Gln Leu Arg Val Ala Ser Lys Glu Asn Asn
            340                 345                 350

Trp Asn Leu Pro Phe Ala Asp Ile Ala Ser Ile Trp Arg Asp Gly Cys
        355                 360                 365

Ile Ile Arg Ser Arg Phe Leu Gln Lys Ile Thr Asp Ala Tyr Asn Arg
        370                 375                 380

Asp Ala Asp Leu Ala Asn Leu Leu Leu Asp Glu Tyr Phe Leu Asp Val
385                 390                 395                 400

Thr Ala Lys Tyr Gln Gln Ala Val Arg Asp Ile Val Ala Leu Ala Val
                405                 410                 415

Gln Ala Gly Val Pro Val Pro Thr Phe Ser Ala Ala Ile Thr Tyr Phe
            420                 425                 430

Asp Ser Tyr Arg Ser Ala Asp Leu Pro Ala Asn Leu Ile Gln Ala Gln
        435                 440                 445

Arg Asp Tyr Phe Gly Ala His Thr Tyr Gln Arg Lys Asp Lys Glu Gly
        450                 455                 460

Thr Phe His Tyr Ser Trp Tyr Asp Glu Lys
465                 470

<210> SEQ ID NO 23
<211> LENGTH: 444
<212> TYPE: PRT
<213> ORGANISM: Streptococcus pneumoniae

<400> SEQUENCE: 23

Met Asn Ala Ile Gln Glu Ser Phe Thr Asp Lys Leu Phe Ala Asn Tyr
1               5                   10                  15

Glu Ala Asn Val Lys Tyr Gln Ala Ile Glu Asn Ala Ala Ser His Asn
            20                  25                  30

Gly Ile Phe Ala Ala Leu Glu Arg Arg Gln Ser His Val Asp Asn Thr
        35                  40                  45

Pro Val Phe Ser Leu Asp Leu Thr Lys Asp Lys Val Thr Asn Gln Lys
    50                  55                  60

Ala Ser Gly Arg Cys Trp Met Phe Ala Ala Leu Asn Thr Phe Arg His
65                  70                  75                  80

Lys Leu Ile Ser Gln Tyr Lys Leu Glu Asn Phe Glu Leu Ser Gln Ala
                85                  90                  95

His Thr Phe Phe Trp Asp Lys Tyr Glu Lys Ser Asn Trp Phe Leu Glu
            100                 105                 110

Gln Val Ile Ala Thr Ser Asp Gln Glu Leu Thr Ser Arg Lys Val Ser
        115                 120                 125

Phe Leu Leu Gln Thr Pro Gln Gln Asp Gly Gly Gln Trp Asp Met Val
    130                 135                 140

Val Ser Leu Phe Glu Lys Tyr Gly Val Val Pro Lys Ser Val Tyr Pro
145                 150                 155                 160

Glu Ser Val Ser Ser Ser Ser Arg Glu Leu Asn Ala Ile Leu Asn
                165                 170                 175

```
Lys Leu Leu Arg Gln Asp Ala Gln Ile Leu Arg Asp Leu Leu Val Ser
            180                 185                 190

Gly Ala Asp Gln Ala Thr Val Gln Ala Lys Lys Glu Asp Leu Leu Gln
        195                 200                 205

Glu Ile Phe Asn Phe Leu Ala Met Ser Leu Gly Leu Pro Pro Arg Lys
    210                 215                 220

Phe Asp Phe Ala Tyr Arg Asp Lys Asp Asn Asn Tyr Lys Ser Glu Lys
225                 230                 235                 240

Gly Ile Thr Pro Gln Glu Phe Tyr Lys Lys Tyr Val Asn Leu Pro Leu
                245                 250                 255

Glu Asp Tyr Val Ser Val Ile Asn Ala Pro Thr Ala Asp Lys Pro Tyr
            260                 265                 270

Gly Lys Ser Tyr Thr Val Glu Met Leu Gly Asn Val Val Gly Ser Arg
        275                 280                 285

Ala Val Arg Tyr Ile Asn Val Pro Met Glu Arg Leu Lys Glu Leu Ala
    290                 295                 300

Ile Ala Gln Met Gln Ala Gly Glu Thr Val Trp Phe Gly Ser Asp Val
305                 310                 315                 320

Gly Gln Leu Ser Asn Arg Lys Ala Gly Ile Leu Ala Thr Asp Val Tyr
                325                 330                 335

Asp Phe Glu Ser Ser Met Asp Ile Lys Leu Thr Gln Asp Lys Ala Gly
            340                 345                 350

Arg Leu Asp Tyr Ser Glu Ser Leu Met Thr His Ala Met Val Leu Thr
        355                 360                 365

Gly Val Asp Leu Asp Glu Asn Gly Lys Ser Thr Lys Trp Lys Val Glu
    370                 375                 380

Asn Ser Trp Gly Asp Lys Val Gly Thr Asp Gly Tyr Phe Val Ala Ser
385                 390                 395                 400

Asp Ala Trp Met Asp Glu Tyr Thr Tyr Gln Ile Val Val Arg Lys Glu
                405                 410                 415

Leu Leu Thr Ala Glu Glu Gln Ala Ala Tyr Gly Ala Glu Pro Ile Val
            420                 425                 430

Leu Ala Pro Trp Asp Pro Met Gly Ala Leu Ala Glu
        435                 440

<210> SEQ ID NO 24
<211> LENGTH: 1058
<212> TYPE: PRT
<213> ORGANISM: Streptococcus pneumoniae

<400> SEQUENCE: 24

Met Pro Lys Arg Thr Asp Ile Gln Lys Ile Met Val Ile Gly Ser Gly
1               5                   10                  15

Pro Ile Ile Ile Gly Gln Ala Ala Glu Phe Asp Tyr Ala Gly Thr Gln
            20                  25                  30

Ala Cys Leu Ser Leu Lys Glu Glu Gly Tyr Glu Val Leu Val Val Asn
        35                  40                  45

Ser Asn Pro Ala Thr Ile Met Thr Asp Lys Glu Ile Ala Asp Lys Val
    50                  55                  60

Tyr Ile Glu Pro Ile Thr Leu Glu Phe Val Thr Arg Ile Leu Arg Lys
65                  70                  75                  80

Glu Gly Pro Asp Ala Leu Leu Pro Thr Leu Gly Gly Gln Thr Gly Leu
                85                  90                  95

Asn Met Ala Met Glu Leu Ser Lys Asn Gly Ile Leu Asp Glu Leu Gly
            100                 105                 110
```

-continued

Val Glu Leu Leu Gly Thr Lys Leu Ser Ala Ile Asp Gln Ala Glu Asp
            115                 120                 125

Arg Asp Leu Phe Lys Gln Leu Met Glu Glu Leu Glu Gln Pro Ile Pro
        130                 135                 140

Glu Ser Glu Ile Val Asn Thr Val Glu Glu Val Ala Phe Ala Ala
145                 150                 155                 160

Thr Ile Gly Tyr Pro Val Ile Val Arg Pro Ala Phe Thr Leu Gly Gly
                165                 170                 175

Thr Gly Gly Gly Met Cys Ala Asn Glu Lys Glu Leu Arg Glu Ile Thr
            180                 185                 190

Glu Asn Gly Leu Lys Leu Ser Pro Val Thr Gln Cys Leu Ile Glu Arg
        195                 200                 205

Ser Ile Ala Gly Phe Lys Glu Ile Glu Tyr Glu Val Met Arg Asp Ser
    210                 215                 220

Ala Asp Asn Ala Leu Val Val Cys Asn Met Glu Asn Phe Asp Pro Val
225                 230                 235                 240

Gly Ile His Thr Gly Asp Ser Ile Val Phe Ala Pro Ala Gln Thr Met
                245                 250                 255

Ser Asp Tyr Glu Asn Gln Met Leu Arg Asp Ala Ser Leu Ser Ile Ile
            260                 265                 270

Arg Ala Leu Lys Ile Glu Gly Gly Cys Asn Val Gln Leu Ala Leu Asp
        275                 280                 285

Pro Asn Ser Phe Lys Tyr Tyr Val Ile Glu Val Asn Pro Arg Val Ser
    290                 295                 300

Arg Ser Ser Ala Leu Ala Ser Lys Ala Thr Gly Tyr Pro Ile Ala Lys
305                 310                 315                 320

Leu Ala Ala Lys Ile Ala Val Gly Leu Thr Leu Asp Glu Val Ile Asn
                325                 330                 335

Pro Val Thr Gly Ser Thr Tyr Ala Met Phe Glu Pro Ala Leu Asp Tyr
            340                 345                 350

Val Val Ala Lys Ile Pro Arg Phe Pro Phe Asp Lys Phe Glu Lys Gly
        355                 360                 365

Glu Arg Arg Leu Gly Thr Gln Met Lys Ala Thr Gly Glu Val Met Ala
    370                 375                 380

Ile Gly Arg Asn Ile Glu Glu Ser Leu Leu Lys Ala Cys Arg Ser Leu
385                 390                 395                 400

Glu Ile Gly Val His His Asn Glu Ile Pro Glu Leu Ala Ala Val Ser
                405                 410                 415

Asp Asp Ala Leu Ile Glu Lys Val Val Lys Ala Gln Asp Asp Arg Leu
            420                 425                 430

Phe Tyr Val Ser Glu Ala Ile Arg Arg Gly Tyr Thr Pro Glu Glu Ile
        435                 440                 445

Ala Glu Leu Thr Lys Ile Asp Ile Phe Tyr Leu Asp Lys Leu Leu His
    450                 455                 460

Ile Phe Glu Ile Glu Gln Glu Leu Gly Ala His Pro Gln Asp Leu Glu
465                 470                 475                 480

Val Leu Lys Thr Ala Lys Leu Asn Gly Phe Ser Asp Arg Lys Ile Ala
                485                 490                 495

Glu Leu Trp Gly Thr Thr Asp Asp Lys Val Arg Gln Leu Arg Leu Glu
            500                 505                 510

Asn Lys Ile Val Pro Val Tyr Lys Met Val Asp Thr Cys Ala Ala Glu
        515                 520                 525

Phe Asp Ser Glu Thr Pro Tyr Phe Tyr Ser Thr Tyr Gly Trp Glu Asn

```
                530            535            540
Glu Ser Ile Arg Ser Asp Lys Glu Ser Val Leu Val Leu Gly Ser Gly
545                 550                 555                 560

Pro Ile Arg Ile Gly Gln Gly Val Glu Phe Asp Tyr Ala Thr Val His
                565                 570                 575

Ser Val Lys Ala Ile Gln Ala Ala Gly Tyr Glu Ala Ile Ile Met Asn
                580                 585                 590

Ser Asn Pro Glu Thr Val Ser Thr Asp Phe Ser Val Ser Asp Lys Leu
                595                 600                 605

Tyr Phe Glu Pro Leu Thr Phe Glu Asp Val Met Asn Val Ile Asp Leu
            610                 615                 620

Glu Gln Pro Lys Gly Val Ile Val Gln Phe Gly Gln Thr Ala Ile
625                 630                 635                 640

Asn Leu Ala Glu Pro Leu Ala Lys Ala Gly Val Thr Ile Leu Gly Thr
                645                 650                 655

Gln Val Ala Asp Leu Asp Arg Ala Glu Asp Arg Asp Leu Phe Glu Gln
                660                 665                 670

Ala Leu Lys Glu Leu Asp Ile Pro Gln Pro Gly Gln Thr Ala Thr
675                 680                 685

Asn Glu Glu Glu Ala Ala Leu Ala Ala Arg Lys Ile Gly Phe Pro Val
690                 695                 700

Leu Val Arg Pro Ser Tyr Val Leu Gly Gly Arg Ala Met Glu Ile Val
705                 710                 715                 720

Glu Asn Glu Glu Asp Leu Arg Ser Tyr Met Arg Thr Ala Val Lys Ala
                725                 730                 735

Ser Pro Asp His Pro Val Leu Val Asp Ser Tyr Ile Val Gly Gln Glu
                740                 745                 750

Cys Glu Val Asp Ala Ile Ser Asp Gly Lys Asn Val Leu Ile Pro Gly
                755                 760                 765

Ile Met Glu His Ile Glu Arg Ala Gly Val His Ser Gly Asp Ser Met
770                 775                 780

Ala Val Tyr Pro Pro Gln Thr Leu Ser Gln Lys Val Gln Glu Thr Ile
785                 790                 795                 800

Ala Asp Tyr Thr Lys Arg Leu Ala Ile Gly Leu His Cys Leu Gly Met
                805                 810                 815

Met Asn Ile Gln Phe Val Ile Lys Asp Glu Lys Val Tyr Val Ile Glu
                820                 825                 830

Val Asn Pro Arg Ala Ser Arg Thr Val Pro Phe Leu Ser Lys Val Thr
                835                 840                 845

Asn Ile Pro Met Ala Gln Val Ala Thr Lys Leu Ile Leu Gly Gln Ser
850                 855                 860

Leu Ser Glu Leu Gly Tyr Gln Asn Gly Leu Tyr Pro Glu Ser Thr Arg
865                 870                 875                 880

Val His Ile Lys Ala Pro Val Phe Ser Phe Thr Lys Leu Ala Lys Val
                885                 890                 895

Asp Ser Leu Leu Gly Pro Glu Met Lys Ser Thr Gly Glu Val Met Gly
                900                 905                 910

Ser Asp Ala Thr Leu Glu Lys Ala Leu Tyr Lys Ala Phe Glu Ala Ser
                915                 920                 925

Tyr Leu His Leu Pro Thr Phe Gly Asn Val Val Phe Thr Ile Ala Asp
                930                 935                 940

Asp Ala Lys Glu Glu Ala Leu Asn Leu Ala Arg Arg Phe Gln Asn Ile
945                 950                 955                 960
```

```
Gly Tyr Gly Ile Leu Ala Thr Glu Gly Thr Ala Ala Phe Phe Ala Ser
                965                 970                 975

His Gly Leu Gln Ala Gln Pro Val Gly Lys Ile Gly Asp Asp Lys
            980                 985                 990

Asp Ile Pro Ser Phe Val Arg Lys Gly Arg Ile Gln Ala Ile Ile Asn
        995                1000                1005

Thr Val Gly Thr Lys Arg Thr Ala Asp Glu Asp Gly Glu Gln Ile
    1010                1015                1020

Arg Arg Ser Ala Ile Glu His Gly Val Pro Leu Phe Thr Ala Leu
    1025                1030                1035

Asp Thr Ala Asn Ala Met Leu Lys Val Leu Glu Ser Arg Ser Phe
    1040                1045                1050

Val Thr Glu Ala Ile
    1055

<210> SEQ ID NO 25
<211> LENGTH: 332
<212> TYPE: PRT
<213> ORGANISM: Streptococcus pneumoniae

<400> SEQUENCE: 25

Met Thr Ile Met Ser Ile Gly Ile Ile Ala Ser His Gly Glu Phe
1               5                   10                  15

Ala Ala Gly Ile His Gln Ser Gly Ser Met Ile Phe Gly Glu Gln Glu
            20                  25                  30

Lys Val Gln Val Val Thr Phe Met Pro Asn Glu Gly Pro Asp Asp Leu
        35                  40                  45

Tyr Ala Lys Phe Asn Asn Ala Val Ala Phe Asp Ala Glu Asp Glu
    50                  55                  60

Val Leu Val Leu Ala Asp Leu Trp Ser Gly Ser Pro Phe Asn Gln Ala
65                  70                  75                  80

Ser Arg Val Met Gly Glu Asn Pro Glu Arg Lys Phe Ala Ile Ile Thr
                85                  90                  95

Gly Leu Asn Leu Pro Met Leu Ile Gln Ala Tyr Thr Glu Arg Leu Met
                100                 105                 110

Asp Ala Ala Ala Gly Val Glu Lys Val Ala Ala Asn Ile Ile Lys Glu
            115                 120                 125

Ala Lys Asp Gly Ile Lys Ala Leu Pro Glu Glu Leu Asn Pro Val Glu
    130                 135                 140

Glu Val Ala Ser Ala Ala Ala Pro Val Ala Gln Thr Ala Ile Pro
145                 150                 155                 160

Glu Gly Thr Val Ile Gly Asp Gly Lys Leu Lys Ile Asn Leu Ala Arg
                165                 170                 175

Leu Asp Thr Arg Leu Leu His Gly Gln Val Ala Thr Ala Trp Thr Pro
            180                 185                 190

Asp Ser Lys Ala Asn Arg Ile Ile Val Ala Ser Asp Asn Val Ala Lys
        195                 200                 205

Asp Asp Leu Arg Lys Glu Leu Ile Lys Gln Ala Pro Gly Asn Val
    210                 215                 220

Lys Ala Asn Val Val Pro Ile Gln Lys Leu Ile Glu Ile Ser Lys Asp
225                 230                 235                 240

Pro Arg Phe Gly Glu Thr His Ala Leu Ile Leu Phe Glu Thr Pro Gln
                245                 250                 255

Asp Ala Leu Arg Ala Ile Glu Gly Gly Val Pro Ile Lys Thr Leu Asn
            260                 265                 270
```

```
Val Gly Ser Met Ala His Ser Thr Gly Lys Thr Leu Val Asn Thr Val
            275                 280                 285

Leu Ser Met Asp Lys Glu Asp Val Ala Thr Phe Glu Lys Met Arg Asp
        290                 295                 300

Leu Gly Val Glu Phe Asp Val Arg Lys Val Pro Asn Asp Ser Lys Lys
305                 310                 315                 320

Asp Leu Phe Asp Leu Ile Asn Lys Ala Asn Val Lys
                325                 330

<210> SEQ ID NO 26
<211> LENGTH: 259
<212> TYPE: PRT
<213> ORGANISM: Streptococcus pneumoniae

<400> SEQUENCE: 26

Met Ala Val Ile Ser Met Lys Gln Leu Leu Glu Ala Gly Val His Phe
1               5                   10                  15

Gly His Gln Thr Arg Arg Trp Asn Pro Lys Met Ala Lys Tyr Ile Phe
            20                  25                  30

Thr Glu Arg Asn Gly Ile His Val Ile Asp Leu Gln Gln Thr Val Lys
        35                  40                  45

Tyr Ala Asp Gln Ala Tyr Asp Phe Met Arg Ala Ala Ala Asn Asp
50                  55                  60

Ala Val Val Leu Phe Val Gly Thr Lys Lys Gln Ala Ala Asp Ala Val
65                  70                  75                  80

Ala Glu Glu Ala Val Arg Ser Gly Gln Tyr Phe Ile Asn His Arg Trp
                85                  90                  95

Leu Gly Gly Thr Leu Thr Asn Trp Gly Thr Ile Gln Lys Arg Ile Ala
            100                 105                 110

Arg Leu Lys Glu Ile Lys Arg Met Glu Glu Asp Gly Thr Phe Glu Val
        115                 120                 125

Leu Pro Lys Lys Glu Val Ala Leu Leu Asn Lys Gln Arg Ala Arg Leu
130                 135                 140

Glu Lys Phe Leu Gly Gly Ile Glu Asp Met Pro Arg Ile Pro Asp Val
145                 150                 155                 160

Met Tyr Val Val Asp Pro His Lys Glu Gln Ile Ala Val Lys Glu Ala
                165                 170                 175

Lys Lys Leu Gly Ile Pro Val Val Ala Met Val Asp Thr Asn Thr Asp
            180                 185                 190

Pro Asp Asp Ile Asp Val Ile Ile Pro Ala Asn Asp Ala Ile Arg
        195                 200                 205

Ala Val Lys Leu Ile Thr Ala Lys Leu Ala Asp Ala Ile Ile Glu Gly
210                 215                 220

Arg Gln Gly Glu Asp Ala Val Ala Val Glu Ala Phe Ala Ala Leu
225                 230                 235                 240

Glu Thr Gln Ala Asp Ser Ile Glu Glu Ile Val Glu Val Glu Gly
                245                 250                 255

Asp Asn Ala

<210> SEQ ID NO 27
<211> LENGTH: 312
<212> TYPE: PRT
<213> ORGANISM: Streptococcus pneumoniae

<400> SEQUENCE: 27

Met Thr Thr Asn Arg Leu Gln Val Ser Leu Pro Gly Leu Asp Leu Lys
1               5                   10                  15
```

Asn Pro Ile Ile Pro Ala Ser Gly Cys Phe Gly Phe Gly Gln Glu Tyr
            20                  25                  30

Ala Lys Tyr Tyr Asp Leu Asn Leu Leu Gly Ser Ile Met Ile Lys Ala
        35                  40                  45

Thr Thr Leu Glu Pro Arg Phe Gly Asn Pro Thr Pro Arg Val Ala Glu
    50                  55                  60

Thr Pro Ala Gly Met Leu Asn Ala Ile Gly Leu Gln Asn Pro Gly Leu
65                  70                  75                  80

Glu Val Val Leu Ala Glu Lys Leu Pro Trp Leu Glu Arg Glu Tyr Pro
                85                  90                  95

Asn Leu Pro Ile Ile Ala Asn Val Ala Gly Phe Ser Lys Gln Glu Tyr
            100                 105                 110

Ala Ala Val Ser His Gly Ile Ser Lys Ala Thr Asn Val Lys Ala Ile
        115                 120                 125

Glu Leu Asn Ile Ser Cys Pro Asn Val Asp His Cys Asn His Gly Leu
    130                 135                 140

Leu Ile Gly Gln Asp Pro Asp Leu Ala Tyr Asp Val Val Lys Ala Ala
145                 150                 155                 160

Val Glu Ala Ser Glu Val Pro Val Tyr Val Lys Leu Thr Pro Ser Val
                165                 170                 175

Thr Asp Ile Val Thr Val Ala Lys Ala Ala Glu Asp Ala Gly Ala Ser
            180                 185                 190

Gly Leu Thr Met Ile Asn Thr Leu Val Gly Met Arg Phe Asp Leu Lys
        195                 200                 205

Thr Arg Lys Pro Ile Leu Ala Asn Gly Thr Gly Gly Met Ser Gly Pro
    210                 215                 220

Ala Val Phe Pro Val Ala Leu Lys Leu Ile Arg Gln Val Ala Gln Thr
225                 230                 235                 240

Thr Asp Leu Pro Ile Ile Gly Met Gly Gly Val Asp Ser Thr Glu Ala
                245                 250                 255

Ala Leu Glu Met Tyr Leu Ala Gly Ala Ser Ala Ile Gly Val Gly Thr
            260                 265                 270

Ala Asn Phe Thr Asn Pro Tyr Ala Cys Pro Asp Ile Ile Glu Asn Leu
        275                 280                 285

Pro Lys Val Met Asp Lys Tyr Gly Ile Ser Ser Leu Glu Glu Leu Arg
    290                 295                 300

Gln Glu Val Lys Glu Ser Leu Arg
305                 310

<210> SEQ ID NO 28
<211> LENGTH: 307
<212> TYPE: PRT
<213> ORGANISM: Streptococcus pneumoniae

<400> SEQUENCE: 28

Met Ser Glu Asn Gln Gln Ala Leu Asn His Val Val Ser Met Glu Asp
1               5                   10                  15

Leu Thr Val Asp Gln Val Met Lys Leu Ile Lys Arg Gly Ile Glu Phe
            20                  25                  30

Lys Asn Gly Ala Gln Leu Pro Tyr Glu Asp His Pro Ile Val Ser Asn
        35                  40                  45

Leu Phe Phe Glu Asp Ser Thr Arg Thr His Lys Ser Phe Glu Val Ala
    50                  55                  60

Glu Ile Lys Leu Gly Leu Glu Arg Leu Asp Phe Asp Val Lys Thr Ser
65                  70                  75                  80

```
Ser Val Asn Lys Gly Glu Thr Leu Tyr Asp Thr Ile Leu Thr Leu Ser
                85                  90                  95

Ala Leu Gly Val Asp Val Cys Val Ile Arg His Pro Glu Val Asp Tyr
            100                 105                 110

Tyr Arg Glu Leu Ile Ala Ser Pro Thr Ile Thr Thr Ser Ile Ile Asn
        115                 120                 125

Gly Gly Asp Gly Ser Gly Gln His Pro Ser Gln Ser Leu Leu Asp Leu
130                 135                 140

Met Thr Ile Tyr Glu Glu Phe Gly His Phe Glu Gly Leu Lys Val Ala
145                 150                 155                 160

Ile Ala Gly Asp Leu Asp His Ser Arg Val Ala Lys Ser Asn Met Gln
                165                 170                 175

Ile Leu Lys Arg Leu Gly Ala Glu Leu Phe Phe Ala Gly Pro Glu Glu
            180                 185                 190

Trp Arg Ser Gln Glu Phe Ala Asp Tyr Gly Gln Phe Val Thr Ile Asp
        195                 200                 205

Glu Ile Ile Asp Gln Val Asp Val Met Met Phe Leu Arg Val Gln His
210                 215                 220

Glu Arg His Asp Ser Gly Ala Val Phe Ser Lys Glu Asp Tyr His Ala
225                 230                 235                 240

Gln His Gly Leu Thr Gln Glu Arg Tyr Asp Arg Leu Lys Glu Thr Ala
                245                 250                 255

Ile Leu Met His Pro Ala Pro Ile Asn Arg Asp Val Glu Ile Ala Asp
            260                 265                 270

His Leu Val Glu Ala Pro Lys Ser Arg Ile Val Gln Gln Met Thr Asn
        275                 280                 285

Gly Val Phe Val Arg Met Ala Ile Leu Glu Ser Val Leu Ala Ser Arg
290                 295                 300

Asn Ala Asn
305

<210> SEQ ID NO 29
<211> LENGTH: 398
<212> TYPE: PRT
<213> ORGANISM: Streptococcus pneumoniae

<400> SEQUENCE: 29

Met Ala Lys Glu Lys Tyr Asp Arg Ser Lys Pro His Val Asn Ile Gly
1               5                   10                  15

Thr Ile Gly His Val Asp His Gly Lys Thr Thr Leu Thr Ala Ala Ile
                20                  25                  30

Thr Thr Val Leu Ala Arg Arg Leu Pro Ser Ser Val Asn Gln Pro Lys
            35                  40                  45

Asp Tyr Ala Ser Ile Asp Ala Ala Pro Glu Glu Arg Glu Arg Gly Ile
        50                  55                  60

Thr Ile Asn Thr Ala His Val Glu Tyr Glu Thr Lys Arg His Tyr
65                  70                  75                  80

Ala His Ile Asp Ala Pro Gly His Ala Asp Tyr Val Lys Asn Met Ile
                85                  90                  95

Thr Gly Ala Ala Gln Met Asp Gly Ala Ile Leu Val Val Ala Ser Thr
            100                 105                 110

Asp Gly Pro Met Pro Gln Thr Arg Glu His Ile Leu Leu Ser Arg Gln
        115                 120                 125

Val Gly Val Lys His Leu Ile Val Phe Met Asn Lys Val Asp Leu Val
130                 135                 140
```

```
Asp Asp Glu Glu Leu Leu Glu Leu Val Glu Met Glu Ile Arg Asp Leu
145                 150                 155                 160

Leu Ser Glu Tyr Asp Phe Pro Gly Asp Asp Leu Pro Val Ile Gln Gly
            165                 170                 175

Ser Ala Leu Lys Ala Leu Glu Gly Asp Ser Lys Tyr Glu Asp Ile Val
        180                 185                 190

Met Glu Leu Met Asn Thr Val Asp Gly Tyr Ile Pro Glu Pro Glu Arg
    195                 200                 205

Asp Thr Asp Lys Pro Leu Leu Leu Pro Val Glu Asp Val Phe Ser Ile
    210                 215                 220

Thr Gly Arg Gly Thr Val Ala Ser Gly Arg Ile Asp Arg Gly Ile Val
225                 230                 235                 240

Lys Val Asn Asp Glu Ile Glu Ile Val Gly Ile Lys Glu Glu Thr Gln
                245                 250                 255

Lys Ala Val Val Thr Gly Val Glu Met Phe Arg Lys Gln Leu Asp Glu
            260                 265                 270

Gly Leu Ala Gly Asp Asn Val Gly Val Leu Leu Arg Gly Val Gln Arg
        275                 280                 285

Asp Glu Ile Glu Arg Gly Gln Val Ile Ala Lys Pro Gly Ser Ile Asn
    290                 295                 300

Pro His Thr Lys Phe Lys Gly Glu Val Tyr Ile Leu Thr Lys Glu Glu
305                 310                 315                 320

Gly Gly Arg His Thr Pro Phe Phe Asn Asn Tyr Arg Pro Gln Phe Tyr
                325                 330                 335

Phe Arg Thr Thr Asp Val Thr Gly Ser Ile Glu Leu Pro Ala Gly Thr
            340                 345                 350

Glu Met Val Met Pro Gly Asp Asn Val Thr Ile Asp Val Glu Leu Ile
        355                 360                 365

His Pro Ile Ala Val Glu Gln Gly Thr Thr Phe Ser Ile Arg Glu Gly
    370                 375                 380

Gly Arg Thr Val Gly Ser Gly Met Val Thr Glu Ile Glu Ala
385                 390                 395

<210> SEQ ID NO 30
<211> LENGTH: 46
<212> TYPE: PRT
<213> ORGANISM: Streptococcus pneumoniae

<400> SEQUENCE: 30

Met Lys Ser Thr Lys Glu Glu Ile Gln Thr Ile Lys Thr Leu Leu Lys
1               5                   10                  15

Asp Ser Arg Thr Ala Lys Tyr His Lys Arg Leu Gln Ile Glu Val Leu Phe
            20                  25                  30

Cys Leu Met Gly Lys Ser Tyr Lys Glu Ile Ile Glu Leu Leu
        35                  40                  45

<210> SEQ ID NO 31
<211> LENGTH: 398
<212> TYPE: PRT
<213> ORGANISM: Streptococcus pneumoniae

<400> SEQUENCE: 31

Met Ala Lys Leu Thr Val Lys Asp Val Asp Leu Lys Gly Lys Lys Val
1               5                   10                  15

Leu Val Arg Val Asp Phe Asn Val Pro Leu Lys Asp Gly Val Ile Thr
            20                  25                  30
```

```
Asn Asp Asn Arg Ile Thr Ala Ala Leu Pro Thr Ile Lys Tyr Ile Ile
         35                  40                  45

Glu Gln Gly Gly Arg Ala Ile Leu Phe Ser His Leu Gly Arg Val Lys
 50                  55                  60

Glu Glu Ser Asp Lys Ala Gly Lys Ser Leu Ala Pro Val Ala Ala Asp
 65                  70                  75                  80

Leu Ala Ala Lys Leu Gly Gln Asp Val Val Phe Pro Gly Val Thr Arg
             85                  90                  95

Gly Ala Glu Leu Glu Ala Ala Ile Asn Ala Leu Glu Asp Gly Gln Val
                100                 105                 110

Leu Leu Val Glu Asn Thr Arg Tyr Glu Asp Val Asp Gly Lys Lys Glu
            115                 120                 125

Ser Lys Asn Asp Pro Glu Leu Gly Lys Tyr Trp Ala Ser Leu Gly Asp
        130                 135                 140

Gly Ile Phe Val Asn Asp Ala Phe Gly Thr Ala His Arg Ala His Ala
145                 150                 155                 160

Ser Asn Val Gly Ile Ser Ala Asn Val Glu Lys Ala Val Ala Gly Phe
                165                 170                 175

Leu Leu Glu Asn Glu Ile Ala Tyr Ile Gln Glu Ala Val Glu Thr Pro
            180                 185                 190

Glu Arg Pro Phe Val Ala Ile Leu Gly Gly Ser Lys Val Ser Asp Lys
        195                 200                 205

Ile Gly Val Ile Glu Asn Leu Leu Glu Lys Ala Asp Lys Val Leu Ile
210                 215                 220

Gly Gly Gly Met Thr Tyr Thr Phe Tyr Lys Ala Gln Gly Ile Glu Ile
225                 230                 235                 240

Gly Asn Ser Leu Val Glu Glu Asp Lys Leu Asp Val Ala Lys Ala Leu
                245                 250                 255

Leu Glu Lys Ala Asn Gly Lys Leu Ile Leu Pro Val Asp Ser Lys Glu
            260                 265                 270

Ala Asn Ala Phe Ala Gly Tyr Thr Glu Val Arg Asp Thr Glu Gly Glu
        275                 280                 285

Ala Val Ser Glu Gly Phe Leu Gly Leu Asp Ile Gly Pro Lys Ser Ile
    290                 295                 300

Ala Lys Phe Asp Glu Ala Leu Thr Gly Ala Lys Thr Val Val Trp Asn
305                 310                 315                 320

Gly Pro Met Gly Val Phe Glu Asn Pro Asp Phe Gln Ala Gly Thr Ile
                325                 330                 335

Gly Val Met Asp Ala Ile Val Lys Gln Pro Gly Val Lys Ser Ile Ile
            340                 345                 350

Gly Gly Gly Asp Ser Ala Ala Ala Ile Asn Leu Gly Arg Ala Asp
        355                 360                 365

Lys Phe Ser Trp Ile Ser Thr Gly Gly Gly Ala Ser Met Glu Leu Leu
    370                 375                 380

Glu Gly Lys Val Leu Pro Gly Leu Ala Ala Leu Thr Glu Lys
385                 390                 395
```

<210> SEQ ID NO 32
<211> LENGTH: 276
<212> TYPE: PRT
<213> ORGANISM: Streptococcus pneumoniae

<400> SEQUENCE: 32

```
Met Lys Lys Ile Val Lys Tyr Ser Ser Leu Ala Ala Leu Ala Leu Val
 1               5                  10                  15
```

Ala Ala Gly Val Leu Ala Ala Cys Ser Gly Gly Ala Lys Lys Glu Gly
            20                  25                  30

Glu Ala Ala Ser Lys Lys Glu Ile Ile Val Ala Thr Asn Gly Ser Pro
        35                  40                  45

Lys Pro Phe Ile Tyr Glu Glu Asn Gly Glu Leu Thr Gly Tyr Glu Ile
50                  55                  60

Glu Val Val Arg Ala Ile Phe Lys Asp Ser Asp Lys Tyr Asp Val Lys
65                  70                  75                  80

Phe Glu Lys Thr Glu Trp Ser Gly Val Phe Ala Gly Leu Asp Ala Asp
                85                  90                  95

Arg Tyr Asn Met Ala Val Asn Asn Leu Ser Tyr Thr Lys Glu Arg Ala
            100                 105                 110

Glu Lys Tyr Leu Tyr Ala Ala Pro Ile Ala Gln Asn Pro Asn Val Leu
        115                 120                 125

Val Val Lys Lys Asp Asp Ser Ser Ile Lys Ser Leu Asp Asp Ile Gly
130                 135                 140

Gly Lys Ser Thr Glu Val Val Gln Ala Thr Thr Ser Ala Lys Gln Leu
145                 150                 155                 160

Glu Ala Tyr Asn Ala Glu His Thr Asp Asn Pro Thr Ile Leu Asn Tyr
                165                 170                 175

Thr Lys Ala Asp Leu Gln Gln Ile Met Val Arg Leu Ser Asp Gly Gln
            180                 185                 190

Phe Asp Tyr Lys Ile Phe Asp Lys Ile Gly Val Glu Thr Val Ile Lys
        195                 200                 205

Asn Gln Gly Leu Asp Asn Leu Lys Val Ile Glu Leu Pro Ser Asp Gln
210                 215                 220

Gln Pro Tyr Val Tyr Pro Leu Leu Ala Gln Gly Gln Asp Glu Leu Lys
225                 230                 235                 240

Ser Phe Val Asp Lys Arg Ile Lys Glu Leu Tyr Lys Asp Gly Thr Leu
                245                 250                 255

Glu Lys Leu Ser Lys Gln Phe Phe Gly Asp Thr Tyr Leu Pro Ala Glu
            260                 265                 270

Ala Asp Ile Lys
        275

<210> SEQ ID NO 33
<211> LENGTH: 630
<212> TYPE: PRT
<213> ORGANISM: Streptococcus pneumoniae

<400> SEQUENCE: 33

Met Thr Arg Tyr Gln Asp Asp Phe Tyr Asp Ala Ile Asn Gly Glu Trp
1               5                   10                  15

Gln Gln Thr Ala Glu Ile Pro Ala Asp Lys Ser Gln Thr Gly Gly Phe
            20                  25                  30

Val Asp Leu Asp Gln Glu Ile Glu Asp Leu Met Leu Ala Thr Thr Asp
        35                  40                  45

Lys Trp Leu Ala Gly Glu Glu Val Pro Glu Asp Ala Ile Leu Glu Asn
50                  55                  60

Phe Val Lys Tyr His Arg Leu Val Arg Asp Phe Asp Lys Arg Glu Ala
65                  70                  75                  80

Asp Gly Ile Thr Pro Val Leu Pro Leu Lys Glu Phe Gln Glu Leu
                85                  90                  95

Glu Thr Phe Ala Asp Phe Thr Ala Lys Leu Ala Glu Phe Glu Leu Ala
            100                 105                 110

-continued

```
Gly Lys Pro Asn Phe Leu Pro Phe Gly Val Ser Pro Asp Phe Met Asp
            115                 120                 125
Ala Arg Ile Asn Val Leu Trp Ala Ser Ala Pro Ser Thr Ile Leu Pro
130                 135                 140
Asp Thr Thr Tyr Tyr Ala Glu Glu His Pro Gln Arg Glu Glu Leu Leu
145                 150                 155                 160
Thr Leu Trp Lys Glu Ser Ser Ala Asn Leu Leu Lys Ala Tyr Asp Phe
                165                 170                 175
Ser Asp Glu Glu Ile Glu Asp Leu Leu Glu Lys Arg Leu Glu Leu Asp
            180                 185                 190
Arg Arg Val Ala Ala Val Val Leu Ser Asn Glu Glu Ser Ser Glu Tyr
        195                 200                 205
Ala Lys Leu Tyr His Pro Tyr Ser Tyr Glu Asp Phe Lys Lys Phe Ala
    210                 215                 220
Pro Ala Leu Pro Leu Asp Asp Phe Phe Lys Ala Val Ile Gly Gln Leu
225                 230                 235                 240
Pro Asp Lys Val Ile Val Asp Glu Glu Arg Phe Trp Gln Ala Ala Glu
                245                 250                 255
Gln Phe Tyr Ser Glu Glu Ala Trp Ser Leu Leu Lys Ala Thr Leu Ile
            260                 265                 270
Leu Ser Val Val Asn Leu Ser Thr Ser Tyr Leu Thr Glu Asp Ile Arg
        275                 280                 285
Val Leu Ser Gly Ala Tyr Ser Arg Ala Leu Ser Gly Val Pro Glu Ala
    290                 295                 300
Lys Asp Lys Val Lys Ala Ala Tyr His Leu Ala Gln Glu Pro Phe Lys
305                 310                 315                 320
Gln Ala Leu Gly Leu Trp Tyr Ala Arg Glu Lys Phe Ser Pro Glu Ala
                325                 330                 335
Lys Ala Asp Val Glu Lys Lys Val Ala Thr Met Ile Asp Val Tyr Lys
            340                 345                 350
Glu Arg Leu Leu Lys Asn Asp Trp Leu Thr Pro Glu Thr Cys Lys Gln
        355                 360                 365
Ala Ile Val Lys Leu Asn Val Ile Lys Pro Tyr Ile Gly Tyr Pro Glu
    370                 375                 380
Glu Leu Pro Ala Arg Tyr Lys Asp Lys Val Val Asn Glu Thr Ala Ser
385                 390                 395                 400
Leu Phe Glu Asn Ala Leu Ala Phe Ala Arg Val Glu Ile Lys His Ser
                405                 410                 415
Trp Ser Lys Trp Asn Gln Pro Val Asp Tyr Lys Glu Trp Gly Met Pro
            420                 425                 430
Ala His Met Val Asn Ala Tyr Tyr Asn Pro Gln Lys Asn Leu Ile Val
        435                 440                 445
Phe Pro Ala Ala Ile Leu Gln Ala Pro Phe Tyr Asp Leu His Gln Ser
    450                 455                 460
Ser Ser Ala Asn Tyr Gly Gly Ile Gly Ala Val Ile Ala His Glu Ile
465                 470                 475                 480
Ser His Ala Phe Asp Thr Asn Gly Ala Ser Phe Asp Glu Asn Gly Ser
                485                 490                 495
Leu Lys Asp Trp Trp Thr Glu Ser Asp Tyr Ala Ala Phe Lys Glu Lys
            500                 505                 510
Thr Gln Lys Val Ile Asp Gln Phe Asp Gly Gln Asp Ser Tyr Gly Ala
        515                 520                 525
Thr Ile Asn Gly Lys Leu Thr Val Ser Glu Asn Val Ala Asp Leu Gly
    530                 535                 540
```

Gly Ile Ala Ala Ala Leu Glu Ala Ala Lys Arg Glu Ala Asp Phe Ser
545                 550                 555                 560

Ala Glu Glu Phe Phe Tyr Asn Phe Gly Arg Ile Trp Arg Met Lys Gly
                565                 570                 575

Arg Pro Glu Phe Met Lys Leu Leu Ala Ser Val Asp Val His Ala Pro
            580                 585                 590

Ala Lys Leu Arg Val Asn Val Gln Val Pro Asn Phe Asp Asp Phe Phe
        595                 600                 605

Thr Thr Tyr Asp Val Lys Glu Gly Asp Gly Met Trp Arg Ser Pro Glu
    610                 615                 620

Glu Arg Val Ile Ile Trp
625                 630

<210> SEQ ID NO 34
<211> LENGTH: 149
<212> TYPE: PRT
<213> ORGANISM: Streptococcus pneumoniae

<400> SEQUENCE: 34

Met Ile Gly Val Val Ala Arg Glu Asn Ala Ala Glu Gln Ile Lys Gln
1               5                   10                  15

Tyr Gln Lys Phe Thr Val Asn Ile Ser Asp Glu Thr Ser Met Leu Ala
            20                  25                  30

Met Glu Gln Ala Gly Phe Ile Ser His Gln Glu Lys Leu Glu Arg Leu
        35                  40                  45

Gly Val His Tyr Glu Ile Ser Glu Arg Thr Gln Ile Pro Ile Leu Asp
    50                  55                  60

Ala Cys Pro Leu Val Leu Asp Cys Arg Val Asp Arg Ile Val Glu Glu
65                  70                  75                  80

Asp Gly Ile Cys His Ile Phe Ala Lys Ile Leu Glu Arg Leu Val Ala
                85                  90                  95

Pro Glu Leu Leu Asp Glu Lys Gly His Phe Lys Asn Gln Leu Phe Ala
            100                 105                 110

Pro Thr Tyr Phe Met Gly Asp Gly Tyr Gln Arg Val Tyr Arg Tyr Leu
        115                 120                 125

Asp Lys Arg Val Asp Met Lys Gly Ser Phe Ile Lys Lys Ala Arg Lys
    130                 135                 140

Lys Asp Gly Lys Asn
145

<210> SEQ ID NO 35
<211> LENGTH: 149
<212> TYPE: PRT
<213> ORGANISM: Streptococcus pneumoniae

<400> SEQUENCE: 35

Met Ile Gly Val Val Ala Arg Glu Asn Ala Ala Glu Gln Ile Lys Gln
1               5                   10                  15

Tyr Gln Lys Phe Thr Val Asn Ile Ser Asp Glu Thr Ser Met Leu Ala
            20                  25                  30

Met Glu Gln Ala Gly Phe Ile Ser His Gln Glu Lys Leu Glu Arg Leu
        35                  40                  45

Gly Val His Tyr Glu Ile Ser Glu Arg Thr Gln Thr Pro Ile Leu Asp
    50                  55                  60

Ala Cys Pro Leu Val Leu Asp Cys Arg Val Asp Arg Ile Val Glu Glu
65                  70                  75                  80

```
                                    -continued
Asp Gly Ile Cys His Ile Phe Ala Lys Ile Leu Glu Arg Leu Val Ala
                 85                  90                  95
Pro Glu Leu Leu Asp Glu Lys Gly His Phe Lys Asn Gln Leu Phe Ala
            100                 105                 110
Pro Thr Tyr Phe Met Gly Asp Gly Tyr Gln Arg Val Tyr Arg Tyr Leu
        115                 120                 125
Asp Lys Arg Val Asp Met Lys Gly Ser Phe Ile Lys Lys Ala Arg Lys
    130                 135                 140
Lys Asp Gly Lys Asn
145

<210> SEQ ID NO 36
<211> LENGTH: 18
<212> TYPE: PRT
<213> ORGANISM: Articifical Sequence
<220> FEATURE:
<223> OTHER INFORMATION: Polyhistine epitope tag

<400> SEQUENCE: 36

Lys Asp His Leu Ile His Asn Val His Lys Glu His Ala His Ala His
1               5                   10                  15

Asn Lys
```

PROTEIN-BASED STREPTOCOCCUS PNEUMONIAE VACCINE

This application is a continuation-in-part of application Ser. No. 12/435,781, filed on May 5, 2009, now abandoned, which is a continuation-in-part of application Ser. No. 12/363,383, filed on Jan. 30, 2009, now abandoned, which is a division of application Ser. No. 10/953,513, filed on Sep. 30, 2004, now U.S. Pat. No. 7,504,110, which is a continuation-in-part of application No. PCT/IL03/00271, filed on Apr. 1, 2003, which claims priority to provisional application No. 60/368,981, filed on Apr. 2, 2002. The contents of each application mentioned above are expressly incorporated by reference herein.

FIELD OF THE INVENTION

The present invention relates to vaccine compositions and methods for protecting against infection with *Streptococcus pneumoniae*. More specifically, the present invention provides vaccine compositions comprising *S. pneumoniae* cell wall or cell membrane proteins associated with an age-dependent immune response.

BACKGROUND OF THE INVENTION

The Gram-positive bacterium *Streptococcus pneumoniae* is a major cause of disease, suffering and death worldwide. Diseases caused by infection with this agent include otitis media, pneumonia, bacteremia, sepsis and meningitis. In some cases, infected individuals may become asymptomatic carriers of *S. pneumoniae*, thereby readily allowing the rapid spread of this infective agent throughout the population. In view of the serious consequences of infection with *S. pneumoniae*, as well as its rapid spread within and between populations, there is an urgent need for safe, effective vaccination regimes. Current methods of vaccination are based on inoculation of the subject with polysaccharides obtained from the capsules of *S. pneumoniae*. While these polysaccharide-based vaccine preparations have been found to be reasonably efficacious when used to prevent infection in adult populations, they are significantly less useful in the treatment of young children (under two years of age) and the elderly. One commonly-used capsular polysaccharide 23-valent vaccine, for example, has been found to be only 60% effective in preventing *S. pneumoniae* invasive disease in elderly subjects and completely incapable of yielding neither long-term memory (Hammitt, et al., 2011, Vaccine 29: 2287-2295) nor clinically-useful antibody responses in the under-two age group (Shapiro E. D. et al., 1991, N. Engl. J. Med. 325: 1453-1460).

In an attempt to increase the immunogenicity of these vaccines, various compositions comprising capsular polysaccharides that have been conjugated with various carrier proteins and combined with adjuvant have been used. The resulting so-called conjugate vaccines (CV) currently include 10-13 serotypes. Although vaccines of this type constitute an improvement in relation to the un-conjugated polysaccharide vaccines, they have not overcome the problem of coverage, since they are effective against only about 10% of the 92 known capsular serotypes. Consequently, upon vaccination, pneumococcal carriage and repopulation with serotypes not present in the vaccine occurs (Dagan, 2009, Vaccine 27 Suppl 3: C22-24).

In the cases of certain other bacteria of pathogenic importance for human and other mammalian species, vaccines comprising immunogenic virulence proteins are currently being developed. Such protein-based vaccines should be of particular value in the case of vulnerable subjects such as very young children, in view of the fact that such subjects are able to produce antibodies against foreign proteins. Unfortunately, very little is known of the molecular details of the life cycle of *S. pneumoniae*, or of the nature of role of the various virulence factors which are known or thought to be involved in targeting and infection of susceptible hosts.

Several publications describe and characterize specific *S. pneumoniae* proteins. For example, U.S. Pat. No. 5,958,734, U.S. Pat. No. 5,976,840, U.S. Pat. No. 6,165,760 and U.S. Pat. No. 6,300,119 disclose *S. pneumoniae* GtS polypeptides of various lengths, polynucleotides encoding them and methods for producing such polypeptides by recombinant techniques. WO 02/077021 the sequences of about 2,500 *S. pneumoniae* genes and their corresponding amino acid sequences from type 4 strain that were identified in silico. U.S. Pat. No. 6,699,703 and its counterparts discloses about 2600 *S. pneumoniae* polypeptides and methods for producing such polypeptides by recombinant techniques, compositions comprising same and methods of use in the preparation of a vaccine. WO 98/23631 relates to 111 Streptococcal polynucleotides identified as having a GUG start codon, which encodes a Val residue, to polypeptides encoded by such polynucleotides, and to their production and uses. WO 02/083833 discloses 376 *S. pneumoniae* polypeptide antigens which are surface localized, membrane associated, secreted or exposed on the bacteria, for preparation of a diagnostic kit and or vaccine. Although suggested in part of the publications, no working examples for the use of the proteins as antigens in the production of a vaccine were provided. Furthermore, none of these references disclose or suggest that use of selected protein antigens which do no elicit immune response in infants and in elderly, improve the outcome of vaccination against *S. pneumoniae*.

Phosphoenolpyruvate protein phosphotransferase (PPP, also known as PtsA) is an intracellular protein that belongs to the sugar phosphotransferase system (PTS) and is also localized to the bacterial cell wall. In the cytoplasm PPP belongs to the group of phosphtransferase systems (PTS) responsible for carbohydrate internalization, which occurs concurrently with their phosphorylation. The phosphorylation of the membrane-spanning enzyme is dependent upon a group of proteins that sequentially transfer a phosphate group to this enzyme. PPP is a cytoplasmic protein that catalyzes the initial step in this process by transferring a phosphate group from phosphoenolpyruvate to a histidine in another enzyme, HrP in this system (Saier, M. H., Jr. & Reizer, J. 1992, J Bacteriol 174: 1433-1438).

There is an unmet need to provide protein-based vaccine compositions which overcome the problems and drawbacks of currently available vaccines, by being effective against a wide range of different *S. pneumoniae* serotypes, and capable of protecting all age groups including infants and elderly.

SUMMARY OF THE INVENTION

It has now been found that it is possible to protect individuals against infection with *S. pneumoniae* by means of administering to said individuals a vaccine composition comprising one or more proteins isolated from the outer layers of the aforementioned bacteria and/or one or more immunonologically-active fragments, derivatives or modifications thereof. Unexpectedly, it was found that a defined set of proteins, associated with age-dependent immunity, are effective in vaccine compositions against a wide range of different *S. pneumoniae* serotypes, and in all age groups, including those age groups that do not produce anti-*S. pneumoniae* antibodies following vaccination with polysaccharide-based compositions, or those resulting in a shift in serotype distribution towards those pneumococcal capsular polysaccharides that are not present in the vaccine. These age groups include infants aged 0-4 years and elderly. Thus, the use of the set of antigens in accordance with the principle of the invention overcomes the disadvantages of known vaccines.

It is now disclosed that the antibody response to *S. pneumoniae* proteins increases with age in infants and this increase correlates negatively with morbidity. Antibodies to *S. pneumoniae* protein antigens develop in humans during the asymptomatic carriage and invasive disease. Infants below two years of age who are at most risk from pneumococcal infections do not respond efficiently to currently available polysaccharide-based vaccination. It is now unexpectedly shown, using sera longitudinally collected from healthy children, exposed to bacterial infections that there is an age-dependent enhancement of the antibody response to certain *S. pneumoniae* surface protein antigens, while in most other proteins there is no enhancement of immunogenicity during the checked time period. This enhancement, with age, of antibody responses against a set of specific pneumococcal surface proteins is implicated in the development of natural immunity and was used in the present invention to identify candidate antigens (herein "age dependent proteins") for use in improved vaccine compositions effective in all age groups, including infants, immunocompromized subjects and elderly.

In elderly subjects capsular polysaccharide based vaccines are only 60% effective in preventing *S. pneumoniae* invasive disease. An elderly subject should be vaccinated at least once in five years and the vaccination efficacy is reduced in each repeated vaccination. The protein-based vaccines of the present invention, which are T-cell dependent antigens, are expected to be more effective than the polysaccharide-based vaccines in elderly subjects.

The present invention provides a method for protecting individuals against infection with *S. pneumoniae* by the use of a protein-based vaccine.

The present invention further provides a protein-based vaccine that is prepared from at least one of a specific set of immunogenic cell wall and/or cell membrane proteins of *S. pneumoniae*, having age-dependent immune responses, or from one or more immunologically-active fragments, derivatives or modifications thereof.

According to one aspect of the present invention, a vaccine composition comprises as an active ingredient one or more isolated proteins selected from one or more *S. pneumoniae* cell wall or cell membrane proteins or immunologically-active protein fragments, derivatives or modifications thereof, which are associated with an age-dependent immune response. According to preferred embodiments, this aspect of the invention said the age-dependent *S. pneumoniae* cell wall and/or cell membrane protein is selected from the group consisting of: phosphoenolpyruvate protein phosphotransferase (Accession No. NP_345645, SEQ ID NO: 4); phosphoglucomutase/phosphomannomutase family protein (Accession No. NP_346006, SEQ ID NO: 5); trigger factor (Accession No. NP_344923, SEQ ID NO: 6); elongation factor G/tetracycline resistance protein (tetO), (Accession No. NP_344811, SEQ ID NO: 7); NADH oxidase (Accession No. NP_345923, SEQ ID NO: 8); Aspartyl/glutamyl-tRNA amidotransferase subunit C (Accession No. NP_344960, SEQ ID NO: 9); cell division protein FtsZ (Accession No. NP_346105, SEQ ID NO: 10); L-lactate dehydrogenase (Accession No. NP_345686, SEQ ID NO: 11); glyceraldehyde 3-phosphate dehydrogenase (GAPDH), (Accession No. NP_346439, SEQ ID NO: 12); fructose-bisphosphate aldolase (Accession No. NP_345117, SEQ ID NO: 13); UDP-glucose 4-epimerase (Accession No. NP_346261, SEQ ID NO: 14); elongation factor Tu family protein (Accession No. NP_358192, SEQ ID NO: 15); Bifunctional GMP synthase/glutamine amidotransferase protein (Accession No. NP_345899, SEQ ID NO: 16); glutamyl-tRNA synthetase (Accession No. NP_346492, SEQ ID NO: 17); glutamate dehydrogenase (Accession No. NP_345769, SEQ ID NO: 18); Elongation factor TS (Accession No. NP_346622, SEQ ID NO: 19); phosphoglycerate kinase (TIGR4) (Accession No. AAK74657, SEQ ID NO: 20); 30S ribosomal protein S1 (Accession No. NP_345350, SEQ ID NO: 21); 6-phosphogluconate dehydrogenase (Accession No. NP_357929, SEQ ID NO: 22); aminopeptidase C (Accession No. NP_344819, SEQ ID NO: 23); carbamoyl-phosphate synthase (large subunit) (Accession No. NP_345739, SEQ ID NO: 24); PTS system, mannose-specific IIAB components (Accession No. NP_344822, SEQ ID NO: 25); 30S ribosomal protein S2 (Accession No. NP_346623, SEQ ID NO: 26); dihydroorotate dehydrogenase 1B (Accession No. NP_358460, SEQ ID NO: 27); aspartate carbamoyltransferase catalytic subunit (Accession No. NP_345741, SEQ ID NO: 28); elongation factor Tu (Accession No. NP_345941, SEQ ID NO: 29); Pneumococcal surface immunogenic protein A (PsipA) (Accession No. NP_344634, SEQ ID NO: 30); phosphoglycerate kinase (R6) (Accession No. NP_358035, SEQ ID NO: 31); ABC transporter substrate-binding protein (Accession No. NP_344690, SEQ ID NO: 32); endopeptidase O (Accession No. NP_346087, SEQ ID NO: 33); Pneumococcal surface immunogenic protein B (PsipB) (Accession No. NP_358083, SEQ ID NO: 34); Pneumococcal surface immunogenic protein C (PsipC) (Accession No. NP_345081, SEQ ID NO: 35).

According to a particular embodiment, the vaccine composition comprises the age-dependent protein phosphoenolpyruvate protein phosphotransferase (PPP or rPtsA) of Accession No. NP_345645, set forth in SEQ ID NO: 4, or a fragment or modification thereof wherein such fragment or modification is capable of eliciting an immune response against *S. pneumoniae*.

According to other embodiments, the vaccine composition comprises at least one age-dependent protein selected from the group consisting of: phosphoenolpyruvate protein phosphotransferase (PPP, Accession No. NP_345645, SEQ ID NO: 4); Fructose-bisphosphate aldolase (NP 345117, SEQ ID NO: 13); Aminopeptidase C (NP_344819, SEQ ID NO: 23); NADH oxidase (NOX, NP_345923, SEQ ID NO: 8) and ABC transporter substrate-binding protein (Accession No. NP_344690, SEQ ID NO: 32).

According to some embodiments the one or more bacterial proteins of the vaccine are effective in all age groups, including those age groups that do not produce anti-*S. pneumoniae* antibodies following vaccination with polysaccharide-based vaccines; or exposure to the bacteria.

According to one embodiment the age group comprises infants less than four years of age.

According to another embodiment the age group comprises infants less than two years of age.

According to one embodiment the age group comprises elderly subjects.

According to yet another embodiment the age group comprises children older the 4 years of age and adult subjects.

According to another embodiment the age group comprises immunocompromised subjects.

The vaccine compositions of the present invention may also contain other, non-immunologically-specific additives, diluents and excipients. For example, in many cases, the vaccine compositions of the present invention may contain, in addition to the *S. pneumoniae* cell-wall and/or cell-membrane protein(s), one or more adjuvants.

Pharmaceutically acceptable adjuvants include, but are not limited to water in oil emulsion, lipid emulsion, and liposomes. According to specific embodiments the adjuvant is selected from the group consisting of: Montanide®, alum, muramyl dipeptide, Gelvac®, chitin microparticles, chitosan, cholera toxin subunit B, labile toxin, AS21A, AS02V, Intralipid®, Lipofundin, Monophosphoryl lipid A; RIBI: monophosphoryl lipid A with Mycobacterial cell wall components (muramy tri peptide), ISCOMs Immune stimulating complexes, CpG, and DNA vaccines such as pVAC. Also included are immune enhancers such as cytokines.

In some embodiments the vaccine composition is formulated for intramuscular, intranasal, oral, intraperitoneal, subcutaneous, topical, intradermal and transdermal delivery. In some embodiments the vaccine is formulated for intramuscular administration. In other embodiments the vaccine is formulated for oral administration. In yet other embodiments the vaccine is formulated for intranasal administration.

In one particularly preferred embodiment, the method of the present invention for protection of mammalian subjects against infection with *S. pneumoniae* comprises administering to a subject in need of such protection an effective amount of at least one cell wall and/or cell membrane proteins associated with age-related immune response, and/or immunogenically-active fragments, derivatives or modifications thereof, wherein said at least one protein is selected from the group consisting of: fructose-bisphosphate aldolase (FBA, NP_345117, SEQ ID NO:13), Phosphoenolpyruvate protein phosphotransferase (PPP) NP_345645 (SEQ ID NO:4), Glutamyl tRNA synthetase (GtS, NP_346492, SEQ ID NO:17), NADH oxidase (NOX, NP_345923, SEQ ID NO:8), Pneumococcal surface immunogenic protein B (PsipB; NP_358083, SEQ ID NO:34), trigger factor (TF, NP 344923, SEQ ID NO:6), FtsZ cell division protein (NP_346105, SEQ ID NO:10), PTS system, mannose-specific IIAB components (PTS, NP_344822, SEQ ID NO:25), and Elongation factor G (EFG, NP344811, SEQ ID NO:7).

According to a particular embodiment, the method comprises administration of the protein phosphoenolpyruvate protein phosphotransferase (PPP or rPtsA) of Accession No. NP_345645, set forth in SEQ ID NO: 4, or a fragment or modification thereof wherein such fragment or modification is capable of eliciting an immune response against *S. pneumoniae*.

According to some embodiments at least one protein of the vaccine composition is an enzyme involved in glycolysis. According to a specific embodiment the at least one protein involved in glycolysis is selected from the group consisting of: L-lactate dehydrogenase (SEQ ID NO: 11), UDP-glucose 4-epimerase (SEQ ID NO: 14), fructose-bisphosphate aldolase (SEQ ID NO: 13), glyceraldehyde-3-phosphate dehydrogenase (SEQ ID NO: 12), phosphoglycerate kinase (SEQ ID NO: 31) and 6-phosphoglutamate dehydrogenase (SEQ ID NO: 22).

According to another embodiment at least one protein of the vaccine composition is an enzyme involved in protein synthesis. According to a specific embodiment the protein involved in protein synthesis is glutamyl-tRNA amidotransferase (SEQ ID NO: 16) or glutamyl-tRNA synthetase (SEQ ID NO: 17).

According to other embodiments at least one protein of the vaccine composition is an enzyme belonging to the other physiological pathways selected from: NADP glutamate dehydrogenase (NP_345769), aminopeptidase C (Accession No. NP_344819, SEQ ID NO: 23), carbamoylphosphate synthase (Accession No. NP_345739, SEQ ID NO: 24), aspartate carbamoyltransferase (Accession No. NP_345741, SEQ ID NO: 28), NADH oxidase (NOX, Accession No. NP_345923, SEQ ID NO: 8), Pneumococcal surface immunogenic protein B (PsipB, Accession No. NP_358083, SEQ ID NO: 34); and pyruvate oxidase.

In some embodiments the cell wall and/or cell membrane proteins are lectins. According to specific embodiments the lectin proteins are selected from the group consisting of: Fructose-bisphosphate aldolase (NP 345117, SEQ ID NO:13); Aminopeptidase C (NP_344819, SEQ ID NO:23).

According to some embodiments the *S. pneumoniae* proteins and/or fragments, derivatives or modifications thereof are lectins and the vaccine compositions comprising them are particularly efficacious in the prevention of localized *S. pneumoniae* infections. In one preferred embodiment, the localized infections are infections of mucosal tissue, particularly of nasal and other respiratory mucosa.

In alternative embodiments of the method of the invention, the cell wall and/or cell membrane proteins are non-lectins.

In specific embodiments the non-lectin proteins are selected from the group consisting of: Phosphomannomutase (NP 346006, SEQ ID NO:5); Trigger factor (NP 344923, SEQ ID NO:6); NADH oxidase (NP 345923, SEQ ID NO:8); L-lactate dehydrogenase (NP 345686, SEQ ID NO:11); Glutamyl-tRNA synthetase (NP 346492, SEQ ID NO:17).

According to other embodiments the *S. pneumoniae* proteins and/or their fragments, derivatives or modifications used in the aforementioned methods, compositions and vaccines are non-lectins, and the vaccine compositions are particularly efficacious in the prevention of systemic *S. pneumoniae* infections.

In another preferred embodiment of the method of the invention, vaccine composition comprises at least one lectin protein and at least one non-lectin protein.

The present invention is directed according to another aspect to a method for preventing infection of mammalian subjects with *S. pneumoniae*, wherein said method comprises administering to a subject in need of such treatment an effective amount of one or more *S. pneumoniae* cell wall and/or cell membrane proteins associated with age-related immune response, and/or immunogenically-active fragments, derivatives or modifications thereof, wherein said proteins are selected from the group consisting of: phosphoenolpyruvate protein phosphotransferase (Accession No. NP_345645, SEQ ID NO:4); phosphoglucomutase/phosphomannomutase family protein (Accession No. NP_346006, SEQ ID NO:5); trigger factor (Accession No. NP_344923, SEQ ID NO:6); elongation factor G/tetracycline resistance protein (tetO), (Accession No. NP_344811, SEQ ID NO:7); NADH oxidase (Accession No. NP_345923, SEQ ID NO:8); Aspartyl/glutamyl-tRNA amidotransferase subunit C (Accession No. NP_344960, SEQ ID NO:9); cell division protein FtsZ (Accession No. NP_346105, SEQ ID NO:10); L-lactate dehydrogenase (Accession No. NP_345686, SEQ ID NO:11); glyceraldehyde 3-phosphate dehydrogenase (GAPDH), (Accession No. NP_346439, SEQ ID NO:12); fructose-bisphosphate aldolase (Accession No. NP_345117, SEQ ID NO:13); UDP-glucose 4-epimerase (Accession No. NP_346261, SEQ ID NO:14); elongation factor Tu family protein (Accession No. NP_358192, SEQ ID NO:15); Bifunctional GMP synthase/glutamine amidotransferase protein (Accession No. NP_345899, SEQ ID NO:16); glutamyl-tRNA synthetase (Accession No. NP 346492, SEQ ID NO:17); glutamate dehydrogenase (Accession No.

NP_345769, SEQ ID NO:18); Elongation factor TS (Accession No. NP_346622, SEQ ID NO:19); phosphoglycerate kinase (TIGR4) (Accession No. AAK74657, SEQ ID NO:20); 30S ribosomal protein S1 (Accession No. NP_345350, SEQ ID NO:21); 6-phosphogluconate dehydrogenase (Accession No. NP_357929, SEQ ID NO:22); aminopeptidase C (Accession No. NP_344819, SEQ ID NO:23); carbamoyl-phosphate synthase (large subunit) (Accession No. NP_345739, SEQ ID NO:24); PTS system, mannose-specific IIAB components (Accession No. NP_344822, SEQ ID NO:25); 30S ribosomal protein S2 (Accession No. NP_346623, SEQ ID NO:26); dihydroorotate dehydrogenase 1B (Accession No. NP_358460, SEQ ID NO:27); aspartate carbamoyltransferase catalytic subunit (Accession No. NP_345741, SEQ ID NO:28); elongation factor Tu (Accession No. NP_345941, SEQ ID NO:29); Pneumococcal surface immunogenic protein A (PsipA) (Accession No. NP_344634, SEQ ID NO:30); phosphoglycerate kinase (R6) (Accession No. NP_358035, SEQ ID NO:31); ABC transporter substrate-binding protein (Accession No. NP_344690, SEQ ID NO:32); endopeptidase O (Accession No. NP_346087, SEQ ID NO:33); Pneumococcal surface immunogenic protein B (PsipB) (Accession No. NP_358083, SEQ ID NO:34); Pneumococcal surface immunogenic protein C (PsipC) (Accession No. NP_345081, SEQ ID NO:35).

Vaccine compositions of the present invention can be administered to a subject in need thereof, prior to, during or after occurrence of infection or inoculation with *S. pneumoniae*.

The vaccine compositions of the present invention are administered, according to one embodiment by means of injection. According to some embodiments the injection route is selected from the group consisting of: intramuscular, intradermal or subcutaneous. According to other embodiments the injection route is selected from intravenous and intraperitoneal. According to yet other embodiments the vaccine compositions of the present invention are administered by nasal or oral routes.

According to some embodiments the *S. pneumoniae* proteins and/or fragments, derivatives or modifications thereof are lectins and the vaccine compositions comprising them are particularly efficacious in the prevention of localized *S. pneumoniae* infections. In one preferred embodiment, the localized infections are infections of mucosal tissue, particularly of nasal and other respiratory mucosa.

According to other embodiments the *S. pneumoniae* proteins and/or their fragments, derivatives or modifications used in the aforementioned methods, compositions and vaccines are non-lectins, and the vaccine compositions are particularly efficacious in the prevention of systemic *S. pneumoniae* infections.

In another preferred embodiment of the method of the invention, vaccine composition comprises at least one lectin protein and at least one non-lectin protein.

In one preferred embodiment of the method of the invention, the mammalian subject is a human subject.

The aforementioned vaccine compositions may clearly be used for preventing infection of the mammalian subjects by *S. pneumoniae*. However, said vaccine composition is not restricted to this use alone. Rather it may be usefully employed to prevent infection by any infectious agent whose viability or proliferation may be inhibited by the antibodies generated by a host in response to the inoculation therein of the one or more *S. pneumoniae* proteins provided in said composition.

According to some embodiments the vaccine compositions of the present invention inhibit *S. pneumoniae* adhesion to cells, for example to human lung cells.

DNA vaccines comprising at least one polynucleotide sequence encoding age-dependent bacterial proteins according to the invention are also within the scope of the present invention, as well as methods for protecting a mammalian subject against infection with *S. pneumoniae* comprising administering such polynucleotide sequence to a subject. According to one embodiment the present invention provides a vaccine composition comprising at least one polynucleotide sequence encoding a protein selected from one or more *S. pneumoniae* cell wall or cell membrane proteins or immunogenically-active protein fragments, derivatives or modifications thereof, which is associated with an age-dependent immune response. According to some embodiments the DNA vaccine composition further comprises at least one polynucleotide sequence encoding an adjuvant peptide or protein. According to a preferred embodiment a DNA vaccine according to the invention is administered by intramuscular injection.

The present invention discloses, according to yet a further aspect, a method for identifying bacterial proteins having age-dependent immunogenicity. Identified age-dependent proteins can be used in vaccine compositions against pathogens expressing said proteins.

According to certain embodiments, a method for identifying a bacterial protein having age-dependent immunogenicity is provided the method comprises the steps of: providing an extract of the cell wall and/or cell membrane of the pathogen; separating the extract by 2D-electrophoresis or micro-chromatography; blotting the protein extract to a matrix; probing the blots with sera collected longitudinally from children at different ages; identifying the protein spots having intensity increasing with age; thereby identifying a protein having age-dependent immunogenicity.

According to some embodiments the protein extract is blotted onto a paper. According to other embodiments the proteins are identified using Matrix Assisted Laser Desorption/Ionization mass spectrometery (MALDI-MS) technique According to some embodiments the pathogen is a bacterium. According to specific embodiments the bacterium is *S. pneumoniae* and the sera are collected from children aged 18, 30 and 42 months. According to another embodiment the pathogen is *Streptococcus pyogenes*.

All of the above and other characteristics and advantages of the present invention will be further understood from the following illustrative and non-limitative examples of preferred embodiments thereof.

DETAILED DESCRIPTION OF PREFERRED EMBODIMENTS

Figure 1:
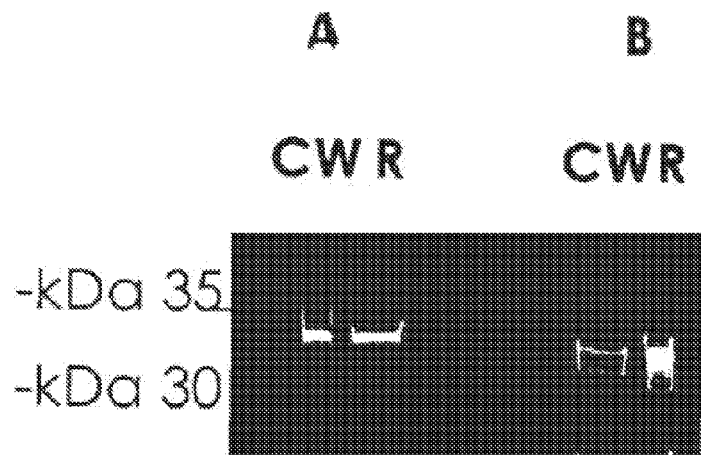
FIG. 1 is a photograph of a Western blot in which the sera of mice immunized with (A) recombinant GAPDH and (B) recombinant fructose-bisphosphate aldolase are seen to recognize the corresponding native proteins (CW) (in an electrophoretically-separated total cell wall protein preparation), and the corresponding recombinant protein (R).

As disclosed herein for the first time, specific pneumococcal surface proteins that exhibit age-dependent immunogenicity, which coincide with the development of natural protective immunity. Proteins identified using antibodies against these proteins, present in infant sera, elicit a protective response against *S. pneumoniae* and can be used for protection against infection with the bacteria. It is now shown that proteins identified as exhibiting age-dependent immune response in infants, or antibodies to such proteins were able to protect mice against infection with *S. pneumoniae*.

Vaccine compositions according to the present invention may be used for preventing infection of the mammalian subjects by *S. pneumoniae*. However, said vaccine compositions may be also usefully employed to prevent adhesion of the bacteria to cells and to inhibit and reduce bacterial load and bacterial carriage. It was shown (Daniely et al., 2006, Clin. Exp. Immunol. 144, 254-263; Mizrachi Nebenzahl et al., 2007, J. Infectious Diseases 196:945-53), that antibodies to proteins identified in the present application as possessing age-dependent immunogenicity are capable of inhibiting *S. pneumoniae* adhesion to human lung cells.

The immunologically variant capsular polysaccharides of *S. pneumoniae* are used widely for the typing of clinical isolates. There are more than 90 capsular serotypes and their prevalence among human isolates varies with age, disease type and to some extent geographical origin. A 23-valent capsular polysaccharide-based vaccine is licensed for use in adults, but it does not elicit an efficient antibody response or protection in children under 2 years of age and immunocompromised patients. To overcome this lack of responsiveness to the T cell independent polysaccharide antigens in young children the conjugate pneumococcal vaccines were developed. These vaccines consist of 7 to 13 of the most prevalent *S. pneumoniae* capsular polysaccharides covalently linked to a protein carrier to stimulate T cell responses to the vaccine. These vaccines are highly effective in preventing invasive pneumococcal disease in infants but there are some drawbacks associated with the complexity of the manufacturing process that increase costs and the limited number of various capsular polysaccharides that can be included in the vaccine. Vaccination with conjugate pneumococcal vaccines has recently been shown to result in a shift in serotype distribution toward those pneumococcal capsular polysaccharides that are not present in the vaccine. In addition, geographical variations in the prevalence of clinically important serotypes of *S. pneumoniae* were described. These concerns combined with the increasing antibiotic resistance are driving research efforts to develop a wide range pneumococcal vaccine that is immunogenic in all age groups and broadly cross-protective against all or most serotypes. In addition proteins are T cell dependent antigen and are more likely to induce long lasting immunological memory.

The reasons to longitudinally start collecting sera from day-care children who are frequently exposed to *S. pneumoniae*, aiming to identify protein antigens involved in the development of natural immunity to *S. pneumoniae*, at 18 months of age were:

i. During gestation maternal IgG antibodies cross the placenta and in the initial months of life these maternal antibodies are protecting the infants.

ii. Starting at 6 months of age the levels of the maternal antibodies decline and a gradual increase in the infants' antibodies start to appear.

iii. Children are most susceptible to *S. pneumoniae* infections between 5-35 months of age. The first decrease in their susceptibility can be observed at between 12-23 months of age however the most significant decrease occurs between 24-35 months of age. It is assumed that natural strong immune response to a protein (for example Pyruvate oxidase and Enolase table 2), preceding this time period is not sufficient to protect children from *S. pneumoniae* infections. Therefore these proteins which did not elicit natural protection against the bacteria although an immune response against them is high in young infants are not age-dependent.

Immunodeficiency comprises a highly variable group of diseases. While primary immunodeficiency result from genetic alteration in genes affecting the immune response, acquired immunodeficiency result from infection with pathogens that affects the immune system (such as HIV-1). Other conditions that may cause diminution of the immune response and increase susceptibility to infections include malnutrition and diseases such as cancer. Most of the immunocompromised patients have acquired immunodeficiency. Malfunction of the immune system may stem from either lack of or the existence of dysfunctional B cells or T cells or macrophages. In other cases immunodeficiency may result in loss of immune memory cells. Antibody deficiencies comprise the most common types of primary immune deficiencies in human subjects. Such patients are highly susceptible to encapsulated bacterial infections. For example, patients that have B cell immunodeficiency could benefit from vaccination with the proteins of the present invention, which are T cell dependent antigens. Patients that demonstrated loss of immune memory, including HIV-1 patients, could also benefit from vaccination with the compositions of the present invention.

Thus it was suspected that the most significant development of natural immunity occurs after two years of age and it was chosen to encompass this period in the attempt to identify proteins that the immune responses to them increase with age during this period. Vaccination of infants in the first year of age with the age-dependent bacterial proteins of the invention is expected to elicit protective immune responses to the bacteria, simulating the development of natural protective immunity that occurs at an older age.

Vaccination protects individuals (and by extension, populations) from the harmful effects of pathogenic agents, such as bacteria, by inducing a specific immunological response to said pathogenic agents in the vaccinated subject.

Vaccines are generally, but not exclusively, administered by means of injection, generally by way of the intramuscular, intradermal or subcutaneous routes. Some vaccines may also be administered by the intravenous, intraperitoneal, nasal or oral routes.

The *S. pneumoniae*-protein containing preparations of the invention can be administered as either single or multiple doses of an effective amount of said protein. The term "effective amount" is used herein to indicate that the vaccine is administered in an amount sufficient to induce or boost a specific immune response, such that measurable amounts (or an increase in the measurable amounts) of one or more antibodies directed against the *S. pneumoniae* proteins used may be detected in the serum or plasma of the vaccinated subject. The precise weight of protein or proteins that constitutes an "effective amount" will depend upon many factors including the age, weight and physical condition of the subject to be vaccinated. The precise quantity also depends upon the capacity of the subject's immune system to produce antibodies, and the degree of protection desired. Effective dosages can be readily established by one of ordinary skill in the art through routine trials establishing dose response curves. However, for the purposes of the present invention, effective amounts of the compositions of the invention can vary from 0.01-1,000 µg/ml per dose, more preferably 0.1-500 µg/ml per dose, wherein the usual dose size is 1 ml.

The vaccine compositions of the present invention, capable of protecting subject from infection or inoculation with *S. pneumoniae* can be administered to a subject in need thereof, prior to, during or after occurrence of infection or inoculation with the bacteria.

In general, the vaccines of the present invention would normally be administered parenterally, by the intramuscular, intravenous, intradermal or subcutaneous routes, either by injection or by a rapid infusion method. Compositions for parenteral administration include sterile aqueous or non-aqueous solutions, suspensions, and emulsions. Examples of non-aqueous solvents are propylene glycol, polyethylene glycol, vegetable oils such as olive oil, and injectable organic esters such as ethyl oleate. Besides the abovementioned inert diluents and solvents, the vaccine compositions of the invention can also include adjuvants, wetting agents, emulsifying and suspending agents, or sweetening, flavoring, or perfuming agents.

The vaccines of the present invention will generally comprise an effective amount of one or more *S. pneumoniae* proteins as the active component, suspended in an appropriate vehicle. In the case of intranasal formulations, for example, said formulations may include vehicles that neither cause irritation to the nasal mucosa nor significantly disturb ciliary function. Diluents such as water, aqueous saline may also be added. The nasal formulations may also contain preservatives including, but not limited to, chlorobutanol and benzalkonium chloride. A surfactant may be present to enhance absorption of the subject proteins by the nasal mucosa. An additional mode of antigen delivery may include an encapsulation technique, which involves complex coacervation of gelatin and chondroitin sulfate (Azhari R, Leong K W. 1991. Complex coacervation of chondroitin sulfate and gelatin and its use for encapsulation and slow release of a model protein. Proc. Symp. Control. Rel. 18: 617; Brown K E, Leong K, Huang C H, Dalal R, Green G D, Haimes H B, Jimenez P A, Bathon J. 1998. Gelatin chondroitin 6-sulfate microspheres for delivery of therapeutic proteins to the joint. Arthritis Rheum 41: 2185-2195).

DEFINITIONS

The term "immunologically-active" is used herein in ordinary sense to refer to an entity (such as a protein or its fragment or derivative) that is capable of eliciting an immune response when introduced into a host subject.

The term "immunogenic protein" according to the present invention denotes a bacterial protein that was identified by antibodies present in human sera. "Antigenicity" refers to the ability of the bacterial protein to produce antibodies against it in the host. The term "age-related immune response" or "age dependent protein" (as used throughout this application) indicates that the ability of subjects to produce antibodies to the bacterial protein or proteins, causing said immune response, increases with age. In the case of human subjects, said ability is measured over a time scale beginning with neonates and ending at approximately four years of age and adults. In non-human mammalian subjects, the "age-related immune response" is measured over an age range extending from neonates to an age at which the immune system of the young mammal is at a stage of development comparable to that of a pre-puberty human child and adults.

It is to be noted that in the context of the present invention, the terms "fragments", "derivatives" and "modifications" are to be understood as follows:

"Fragment": a less than full length portion, or linked portions, of the native sequence of the protein in question, wherein the sequence of said portion is essentially unchanged as compared to the relevant part of the sequence of the native protein.

"Derivative": a full length, and a less than full length portion of the native sequence of the protein in question, wherein either the sequence further comprises (at its termini and/or within said sequence itself) non-native amino acid sequences, i.e. sequences which do not form part of the native protein in question. The term "derivative" also includes within its scope molecular species produced by conjugating chemical groups to the amino residue side chains of the native proteins or fragments thereof, wherein said chemical groups do not form part of the naturally-occurring amino acid residues present in said native proteins.

"Modification": a full length protein or less than full length portion thereof comprising at least one amino acid residue which is not natively present in the same location in the sequence of said protein, which have been introduced as a consequence of mutation of the native sequence (by either random or site-directed processes), by chemical modification or by chemical synthesis.

The term "infection" as used herein in the present application refers to a state in which disease-causing S. pneumoniae have invaded, colonized, spread, adhered, disseminated or multiplied in body cells or tissues. This term encompass the term "inoculation", namely the state in which the bacteria colonized the nasopharynx but there are no infection symptoms yet.

The term "lectins" is used hereinabove and hereinbelow to indicate proteins having the ability to bind specifically to polysaccharides or oligosaccharides. Conversely, the term "non-lectins" is used to refer to proteins lacking the aforementioned saccharide-binding property, or to proteins which do not bind the saccharides tested in the present application.

Vaccine Formulation

The vaccines of the present invention comprise at least one bacterial protein exhibiting an age-dependent increase antibody response in infants, fragment, derivative or modification of said bacterial protein, and optionally, an adjuvant. Formulation can contain a variety of additives, such as adjuvant, excipient, stabilizers, buffers, or preservatives. The vaccine can be formulated for administration in one of many different modes.

In preferred embodiment, the vaccine is formulated for parenteral administration, for example intramuscular administration. According to yet another embodiment the administration is orally.

According to yet another embodiment the administration is intradermal. Needles specifically designed to deposit the vaccine intradermally are known in the art as disclosed for example in U.S. Pat. Nos. 6,843,781 and 7,250,036 among others. According to other embodiments the administration is performed with a needleless injector.

According to one embodiment of the invention, the vaccine is administered intranasally. The vaccine formulation may be applied to the lymphatic tissue of the nose in any convenient manner. However, it is preferred to apply it as a liquid stream or liquid droplets to the walls of the nasal passage. The intranasal composition can be formulated, for example, in liquid form as nose drops, spray, or suitable for inhalation, as powder, as cream, or as emulsion.

In another embodiment of the invention, administration is oral and the vaccine may be presented, for example, in the form of a tablet or encased in a gelatin capsule or a microcapsule.

The formulation of these modalities is general knowledge to those with skill in the art.

Liposomes provide another delivery system for antigen delivery and presentation. Liposomes are bilayered vesicles composed of phospholipids and other sterols surrounding a typically aqueous center where antigens or other products can be encapsulated. The liposome structure is highly versatile with many types range in nanometer to micrometer sizes, from about 25 nm to about 500 µm. Liposomes have been found to be effective in delivering therapeutic agents to dermal and mucosal surfaces. Liposomes can be further modified for targeted delivery by for example, incorporating specific antibodies into the surface membrane, or altered to encapsulate bacteria, viruses or parasites. The average survival time or half life of the intact liposome structure can be extended with the inclusion of certain polymers, for example polyethylene glycol, allowing for prolonged release in vivo. Liposomes may be unilamellar or multilamellar.

The vaccine composition may be formulated by: encapsulating an antigen or an antigen/adjuvant complex in liposomes to form liposome-encapsulated antigen and mixing the liposome-encapsulated antigen with a carrier comprising a continuous phase of a hydrophobic substance. If an antigen/adjuvant complex is not used in the first step, a suitable adjuvant may be added to the liposome-encapsulated antigen, to the mixture of liposome-encapsulated antigen and carrier, or to the carrier before the carrier is mixed with the liposome-encapsulated antigen. The order of the process may depend on the type of adjuvant used. Typically, when an adjuvant like alum is used, the adjuvant and the antigen are mixed first to form an antigen/adjuvant complex followed by encapsulation of the antigen/adjuvant complex with liposomes. The resulting liposome-encapsulated antigen is then mixed with the carrier. The term "liposome-encapsulated antigen" may refer to encapsulation of the antigen alone or to the encapsulation of the antigen/adjuvant complex depending on the context. This promotes intimate contact between the adjuvant and the antigen and may, at least in part, account for the immune response when alum is used as the adjuvant. When another is used, the antigen may be first encapsulated in liposomes and the resulting liposome-encapsulated antigen is then mixed into the adjuvant in a hydrophobic substance.

In formulating a vaccine composition that is substantially free of water, antigen or antigen/adjuvant complex is encapsulated with liposomes and mixed with a hydrophobic substance. In formulating a vaccine in an emulsion of water-in-a hydrophobic substance, the antigen or antigen/adjuvant complex is encapsulated with liposomes in an aqueous medium followed by the mixing of the aqueous medium with a hydrophobic substance. In the case of the emulsion, to maintain the hydrophobic substance in the continuous phase, the aqueous medium containing the liposomes may be added in aliquots with mixing to the hydrophobic substance.

In all methods of formulation, the liposome-encapsulated antigen may be freeze-dried before being mixed with the hydrophobic substance or with the aqueous medium as the case may be. In some instances, an antigen/adjuvant complex may be encapsulated by liposomes followed by freeze-drying. In other instances, the antigen may be encapsulated by liposomes followed by the addition of adjuvant then freeze-drying to form a freeze-dried liposome-encapsulated antigen with external adjuvant. In yet another instance, the antigen may be encapsulated by liposomes followed by freeze-drying before the addition of adjuvant. Freeze-drying may promote better interaction between the adjuvant and the antigen resulting in a more efficacious vaccine.

Formulation of the liposome-encapsulated antigen into a hydrophobic substance may also involve the use of an emulsifier to promote more even distribution of the liposomes in the hydrophobic substance. Typical emulsifiers are well-known in the art and include mannide oleate (Arlacel™ A), lecithin, Tween™ 80, Spans™ 20, 80, 83 and 85. The emulsifier is used in an amount effective to promote even distribution of the liposomes. Typically, the volume ratio (v/v) of hydrophobic substance to emulsifier is in the range of about 5:1 to about 15:1.

Microparticles and nanoparticles employ small biodegradable spheres which act as depots for vaccine delivery. The major advantage that polymer microspheres possess over other depot-effecting adjuvants is that they are extremely safe and have been approved by the Food and Drug Administration in the US for use in human medicine as suitable sutures and for use as a biodegradable drug delivery system (Langer R. Science. 1990; 249(4976):1527-33). The rates of copolymer hydrolysis are very well characterized, which in turn allows for the manufacture of microparticles with sustained antigen release over prolonged periods of time (O'Hagen, et al., Vaccine, 1993;11:965-9).

Parenteral administration of microparticles elicits long-lasting immunity, especially if they incorporate prolonged release characteristics. The rate of release can be modulated by the mixture of polymers and their relative molecular weights, which will hydrolyze over varying periods of time. Without wishing to be bound to theory, the formulation of different sized particles (1 μm to 200 μm) may also contribute to long-lasting immunological responses since large particles must be broken down into smaller particles before being available for macrophage uptake. In this manner a single-injection vaccine could be developed by integrating various particle sizes, thereby prolonging antigen presentation and greatly benefiting livestock producers.

In some applications an adjuvant or excipient may be included in the vaccine formulation. Montanide™ (Incomplete Freund's adjuvant) and alum for example, are preferred adjuvants for human use. The choice of the adjuvant will be determined in part by the mode of administration of the vaccine. A preferred mode of administration is intramuscular administration. Another preferred mode of administration is intranasal administration. Non-limiting examples of intranasal adjuvants include chitosan powder, PLA and PLG microspheres, QS-21, AS02A, calcium phosphate nanoparticles (CAP); mCTA/LTB (mutant cholera toxin E112K with pentameric B subunit of heat labile enterotoxin), and detoxified E. Coli derived labile toxin.

The adjuvant used may also be, theoretically, any of the adjuvants known for peptide- or protein-based vaccines. For example: inorganic adjuvants in gel form (aluminium hydroxide/aluminium phosphate, Warren et al., 1986; calcium phosphate, Relyvelt, 1986); bacterial adjuvants such as monophosphoryl lipid A (Ribi, 1984; Baker et al., 1988) and muramyl peptides (Ellouz et al., 1974; Allison and Byars, 1991; Waters et al., 1986); particulate adjuvants such as the so-called ISCOMS ("immunostimulatory complexes", Mowat and Donachie, 1991; Takahashi et al., 1990; Thapar et al., 1991), liposomes (Mbawuike et al. 1990; Abraham, 1992; Phillips and Emili, 1992; Gregoriadis, 1990) and biodegradable microspheres (Marx et al., 1993); adjuvants based on oil emulsions and emulsifiers such as IFA ("Incomplete Freund's adjuvant" (Stuart-Harris, 1969; Warren et al., 1986), SAF (Allison and Byars, 1991), saponines (such as QS-21; Newman et al., 1992), squalene/squalane (Allison and Byars, 1991); synthetic adjuvants such as non-ionic block copolymers (Hunter et al., 1991), muramyl peptide analogs (Azuma, 1992), synthetic lipid A (Warren et al., 1986; Azuma, 1992), synthetic polynucleotides (Harrington et al., 1978) and polycationic adjuvants (WO 97/30721).

Adjuvants for use with immunogens of the present invention include aluminum or calcium salts (for example hydroxide or phosphate salts). A particularly preferred adjuvant for use herein is an aluminum hydroxide gel such as Alhydrogel™. Calcium phosphate nanoparticles (CAP) is an adjuvant being developed by Biosante, Inc (Lincolnshire, Ill.). The immunogen of interest can be either coated to the outside of particles, or encapsulated inside on the inside (He et al., 2000, Clin. Diagn. Lab. Immunol., 7,899-903).

Another adjuvant for use with an immunogen of the present invention is an emulsion. A contemplated emulsion can be an oil-in-water emulsion or a water-in-oil emulsion. In addition to the immunogenic chimer protein particles, such emulsions comprise an oil phase of squalene, squalane, peanut oil or the like as are well known, and a dispersing agent. Non-ionic dispersing agents are preferred and such materials include mono- and di-$C_{12}$-$C_{24}$-fatty acid esters of sorbitan and mannide such as sorbitan mono-stearate, sorbitan mono-oleate and mannide mono-oleate.

Such emulsions are for example water-in-oil emulsions that comprise squalene, glycerol and a surfactant such as mannide mono-oleate (Arlacel™ A), optionally with squalane, emulsified with the chimer protein particles in an aqueous phase. Alternative components of the oil-phase include alpha-tocopherol, mixed-chain di- and tri-glycerides, and sorbitan esters. Well-known examples of such emulsions include Montanide™ ISA-720, and Montanide™ ISA 703 (Seppic, Castres, France. Other oil-in-water emulsion adjuvants include those disclosed in WO 95/17210 and EP 0 399 843.

The use of small molecule adjuvants is also contemplated herein. One type of small molecule adjuvant useful herein is a 7-substituted-8-oxo- or 8-sulfo-guanosine derivative described in U.S. Pat. No. 4,539,205, U.S. Pat. No. 4,643,992, U.S. Pat. No. 5,011,828 and U.S. Pat. No. 5,093,318. 7-allyl-8-oxoguanosine(loxoribine) has been shown to be particularly effective in inducing an antigen-(immunogen-) specific response.

A useful adjuvant includes monophosphoryl lipid A (MPL®), 3-deacyl monophosphoryl lipid A (3D-MPL®), a well-known adjuvant manufactured by Corixa Corp. of Seattle, formerly Ribi Immunochem, Hamilton, Mont. The adjuvant contains three components extracted from bacteria: monophosphoryl lipid (MPL) A, trehalose dimycolate (TDM) and cell wall skeleton (CWS) (MPL+TDM+CWS) in a 2% squalene/Tween™ 80 emulsion. This adjuvant can be prepared by the methods taught in GB 2122204B.

Other compounds are structurally related to MPL® adjuvant called aminoalkyl glucosamide phosphates (AGPs) such as those available from Corixa Corp under the designation RC-529™ adjuvant {2-[(R)-3-tetra-decanoyloxytetradecanoylamino]-ethyl-2-deoxy-4-O-phosphon-o-3-O-[(R)-3-tetradecanoyloxytetra-decanoyl]-2-[(R)-3-tetra-decanoyloxytet-radecanoyl-amino]-p-D-glucopyranoside triethylammonium salt}. An RC-529 adjuvant is available in a squalene emulsion sold as RC-529SE and in an aqueous formulation as RC-529AF available from Corixa Corp. (see, U.S. Pat. No. 6,355,257 and U.S. Pat. No. 6,303,347; U.S. Pat. No. 6,113,918; and U.S. Publication No. 03-0092643).

Further contemplated adjuvants include synthetic oligonucleotide adjuvants containing the CpG nucleotide motif one or more times (plus flanking sequences) available from Coley Pharmaceutical Group. The adjuvant designated QS21, available from Aquila Biopharmaceuticals, Inc., is an immunologically active saponin fractions having adjuvant activity derived from the bark of the South American tree Quillaja Saponaria Molina (e.g. Quil™ A), and the method of its production is disclosed in U.S. Pat. No. 5,057,540. Derivatives of Quil™ A, for example QS21 (an HPLC purified fraction derivative of Quil™ A also known as QA21), and other fractions such as QA17 are also disclosed. Semi-synthetic and synthetic derivatives of Quillaja Saponaria Molina saponins are also useful, such as those described in U.S. Pat. No. 5,977,081 and U.S. Pat. No. 6,080,725. The adjuvant denominated MF59 available from Chiron Corp. is described in U.S. Pat. No. 5,709,879 and U.S. Pat. No. 6,086,901.

Muramyl dipeptide adjuvants are also contemplated and include N-acetyl-muramyl-L-threonyl-D-isoglutamine (thur-MDP), N-acetyl-nor-muramyl-L-alanyl-D-isoglutamine (CGP 11637, referred to as nor-MDP), and N-acetylmuramyl-L-alanyl-D-isoglutaminyl-L-alanine-2-(1'-2'-dipalmityol-s-n-glycero-3-hydroxyphosphoryloxy) ethylamine ((CGP) 1983A, referred to as MTP-PE). The so-called muramyl dipeptide analogues are described in U.S. Pat. No. 4,767,842.

Other adjuvant mixtures include combinations of 3D-MPL and QS21 (EP 0 671 948 B1), oil-in-water emulsions comprising 3D-MPL and QS21 (WO 95/17210, PCT/EP98/05714), 3D-MPL formulated with other carriers (EP 0 689 454 B1), QS21 formulated in cholesterol-containing liposomes (WO 96/33739), or immunostimulatory oligonucleotides (WO 96/02555). Adjuvant SBAS2 (now ASO2) available from SKB (now Glaxo-SmithKline) contains QS21 and MPL in an oil-in-water emulsion is also useful. Alternative adjuvants include those described in WO 99/52549 and non-particulate suspensions of polyoxyethylene ether (UK Patent Application No. 9807805.8).

The use of an adjuvant that contains one or more agonists for toll-like receptor-4 (TLR-4) such as an MPL® adjuvant or a structurally related compound such as an RC-529® adjuvant or a Lipid A mimetic, alone or along with an agonist for TLR-9 such as a non-methylated oligo deoxynucleotide-containing the CpG motif is also optional.

Another type of adjuvant mixture comprises a stable water-in-oil emulsion further containing aminoalkyl glucosamine phosphates such as described in U.S. Pat. No. 6,113,918. Of the aminoalkyl glucosamine phosphates the molecule known as RC-529 {(2-[(R)-3-tetradecanoyloxytetradecanoylamino] ethyl 2-deoxy-4-O-phosphono-3-O—[(R)-3-tetradecanoyloxy-tetradecanoyl]-2-[(R)-3-tetradecanoyloxytetra-decanoylamino]-p-D-glucopyranoside triethylammonium salt.)} is preferred. One particular water-in-oil emulsion is described in WO 99/56776.

Adjuvants are utilized in an adjuvant amount, which can vary with the adjuvant, host animal and immunogen. Typical amounts can vary from about 1 μg to about 1 mg per immunization. Those skilled in the art know that appropriate concentrations or amounts can be readily determined.

Vaccine compositions comprising an adjuvant based on oil in water emulsion is also included within the scope of the present invention. The water in oil emulsion may comprise a metabolisable oil and a saponin, such as for example as described in U.S. Pat. No. 7,323,182.

According to several embodiments, the vaccine compositions according to the present invention may contain one or more adjuvants, characterized in that it is present as a solution or emulsion which is substantially free from inorganic salt ions, wherein said solution or emulsion contains one or more water soluble or water-emulsifiable substances which is capable of making the vaccine isotonic or hypotonic. The water soluble or water-emulsifiable substances may be, for example, selected from the group consisting of: maltose; fructose; galactose; saccharose; sugar alcohol; lipid; and combinations thereof.

The compositions of the present invention comprise according to several specific embodiments a proteosome adjuvant. The proteosome adjuvant comprises a purified preparation of outer membrane proteins of meningococci and similar preparations from other bacteria. These proteins are highly hydrophobic, reflecting their role as transmembrane proteins and porins. Due to their hydrophobic protein-protein interactions, when appropriately isolated, the proteins form multi-molecular structures consisting of about 60-100 nm diameter whole or fragmented membrane vesicles. This liposome-like physical state allows the proteosome adjuvant to act as a protein carrier and also to act as an adjuvant.

The use of proteosome adjuvant has been described in the prior art and is reviewed by Lowell G H in "New Generation Vaccines", Second Edition, Marcel Dekker Inc, New York, Basel, Hong Kong (1997) pages 193-206. Proteosome adjuvant vesicles are described as comparable in size to certain viruses which are hydrophobic and safe for human use. The review describes formulation of compositions comprising non-covalent complexes between various antigens and proteosome adjuvant vesicles which are formed when solubilizing detergent is selectably removed using exhaustive dialysis technology.

The present invention also encompasses within its scope the preparation and use of DNA vaccines. Vaccination methods and compositions of this type are well known in the art and are comprehensively described in many different articles, monographs and books (see, for example, chapter 11 of "Molecular Biotechnology: principles and applications of recombinant DNA" eds. B. R. Glick & J. J. Pasternak, ASM Press, Washington, D.C., $2^{nd}$ edition, 1998). In principle, DNA vaccination is achieved by cloning the cDNAs for the desired immunogen into a suitable DNA vaccine vector, such as the pVAC vector (Invivogen), using codons optimized for expression in human. In the case of pVAC, the desired immunogenic proteins are targeted and anchored to the cell surface by cloning the gene of interest in frame between the IL2 signal sequence and the C-terminal transmembrane anchoring domain of human placental alkaline phosphatase. The use of other immune enhancers, including adjuvants or cloning in frame other immune enhancing cytokines, together with the DNA vaccines is also within the scope of the present invention. Such DNA vaccine vectors are specifically designed to stimulate humoral immune responses by intramuscular injection. The antigenic peptide produced on the surface of muscle cells is taken up by antigen presenting cells (APCs), processed and presented to the immune system T helper cells through the major histocompatibility complex (MHC) class II molecules.

Oral liquid preparations may be in the form of, for example, aqueous or oily suspension, solutions, emulsions, syrups or elixirs, or may be presented dry in tablet form or a product for reconstitution with water or other suitable vehicle before use. Such liquid preparations may contain conventional additives such as suspending agents, emulsifying agents, non-aqueous vehicles (which may include edible oils), or preservative.

The aforementioned adjuvants are substances that can be used to augment a specific immune response. Normally, the adjuvant and the composition are mixed prior to presentation to the immune system, or presented separately, but into the same site of the subject being vaccinated. Adjuvants that may be usefully employed in the preparation of vaccines include: oil adjuvants (for example, Freund's complete and incomplete adjuvants, that will be used in animal experiments only and is forbidden from use in humans), mineral salts, alum, silica, kaolin, and carbon, polynucleotides and certain natural substances of microbial origin. An additional mode of antigen delivery may include an encapsulation technique, which involves complex coacervation of gelatin and chondroitin sulfate (Azhari R, Leong K W. 1991. Complex coacervation of chondroitin sulfate and gelatin and its use for encapsulation and slow release of a model protein. Proc. Symp. Control. Rel. 18: 617; Brown K E, Leong K, Huang C H, Dalal R, Green G D, Haimes H B, Jimenez P A, Bathon J. 1998. Gelatin/chondroitin 6-sulfate microspheres for delivery of therapeutic proteins to the joint. Arthritis Rheum 41: 2185-2195).

Further examples of materials and methods useful in the preparation of vaccine compositions are well known to those skilled in the art. In addition, further details may be gleaned from Remington's Pharmaceutical Sciences, Mack Publishing Co, Easton, Pa., USA, $20^{th}$ edition 2000.

The S. pneumoniae cell-wall and/or cell-membrane proteins for use in working the present invention may be obtained by directly purifying said proteins from cultures of S. pneumoniae by any of the standard techniques used to prepare and purify cell-surface proteins. Suitable methods are described in many biochemistry text-books, review articles and laboratory guides, including inter alia "Protein Structure: a practical approach" ed. T. E. Creighton, IRL Press, Oxford, UK (1989).

However, it is to be noted that such an approach suffers many practical limitations that present obstacles for producing commercially-viable quantities of the desired proteins. The S. pneumoniae proteins of the present invention may therefore be more conveniently prepared by means of recombinant biotechnological means, whereby the gene for the S. pneumoniae protein of interest is isolated and inserted into an appropriate expression vector system (such as a plasmid or phage), which is then introduced into a host cell that will permit large-scale production of said protein by means of, for example, overexpression.

As a first stage, the location of the genes of interest within the S. pneumoniae genome may be determined by reference to a complete-genome database such as the TIGR4 database that is maintained by the Institute for Genomic Research. The selected sequence may, where appropriate, be isolated directly by the use of appropriate restriction endonucleases, or more effectively by means of PCR amplification. Suitable techniques are described in, for example, U.S. Pat. Nos. 4,683,195, 4,683,202, 4,800,159, 4,965,188, as well as in Innis et al. eds., PCR Protocols: A guide to method and applications. Alternatively, the gene may be chemically synthesized with codons optimized to the expression system actually used (i.e. E. coli). For DNA vaccines, codons are optimized for expression in human.

Following amplification and/or restriction endonuclease digestion, the desired gene or gene fragment is ligated either initially into a cloning vector, or directly into an expression vector that is appropriate for the chosen host cell type. In the case of the S. pneumoniae proteins, Escherichia coli is the most useful expression host. However, many other cell types may be also be usefully employed including other bacteria, yeast cells, insect cells and mammalian cell systems known in the art.

High-level expression of the desired protein (as intact protein sequence, modified protein sequence, fragment of thereof), within the host cell may be achieved in several different ways (depending on the chosen expression vector) including expression as a fusion protein (e.g. with factor Xa or thrombin), expression as a His-tagged protein, dual vector systems, expression systems leading to incorporation of the recombinant protein inside inclusion bodies etc. The recombinant protein will then need to be isolated and purified from the cell membrane, interior cellular soluble fraction, inclusion body or (in the case of secreted proteins) the culture medium, by one of the many methods known in the art.

All of the above recombinant DNA and protein purification techniques are well known to all skilled artisans in the field, the details of said techniques being described in many standard works including "Molecular cloning: a laboratory manual" by Sambrook, J., Fritsch, E. F. & Maniatis, T., Cold Spring Harbor, N.Y., $2^{nd}$ ed., 1989, which is incorporated herein by reference in its entirety.

As disclosed and explained hereinabove, each of the abovementioned embodiments of the invention may be based on the use of one or more intact, full length, cell wall and/or cell membrane proteins or, in the alternative, or in addition thereto, fragments, derivatives and modifications of said full length proteins. Fragments may be obtained by means of recombinant expression of selected regions of the cell wall protein gene(s). Derivatives of the full length proteins or fragments thereof may be obtained by introducing non-native sequences within the DNA sequences encoding said proteins, followed by expression of said derivatized sequences. Derivatives may also be produced by conjugating non-native groups to the amino residue side chains of the cell wall proteins or protein fragments, using standard protein modification techniques. Modified cell wall proteins and protein fragments for use in the present invention may also be obtained by the use of site-directed mutagenesis techniques. Such techniques are well known in the art and are described, for example, in "Molecular cloning: a laboratory manual" by Sambrook, J., Fritsch, E. F. & Maniatis, T., Cold Spring Harbor, N.Y., $2^{nd}$ ed., 1989. Of particular interest is the use of one or more of the preceding techniques to create fragments or derivatives possessing the desired epitopic sites, but lacking other domains which are responsible for adverse effects such as suppression of cellular immune responses. It is to be emphasized that all of the immediately preceding discussion of fragments, derivatives and mutants of the cell wall proteins disclosed herein are to be considered as an integral part of the present invention.

S. pneumoniae infections are common in children under the five years of age mainly under two years of age. The infants' antibody production is known to be produced at 6 months of age. The present invention is based in part on a study performed with sera obtained longitudinally from children at 18, 30 and 42 months of age, attending day care centers, which are exposed to the bacteria. The children's sera were screened for change, with age, of the presence or amount of antibodies to specific cell wall/membrane proteins. Antibodies to specific proteins which were absent or low in sera of younger children and appear or increase with age identified proteins that now would be considered as candidate for vaccine development for protecting infants against S. pneumoniae. Without wishing to be bound to any theory it is suspected that the immune response of younger children to the proteins in the context of the bacterium is also not efficient. Since the increase in the response to these proteins is in reciprocal correlation with disease it was assumed that immunization with these proteins will elicit a protective immune response. Each of the proteins in the set disclosed for the first time in the present application as being associated with age-dependent immune response to the bacteria may elicit protective immune response against the bacteria at all ages to all subjects, including infants, elderly and immunocompromised subjects.

PPP enzymatic function occurs in the cytoplasm, however, it was found also to localize to the cell-wall and to the cytoplasmic membrane. FabD, an enzyme that is involved in lipid metabolism, could be found in the cytoplasm only but could not be found in the cell wall, further suggesting that under the experimental conditions used the cell-wall localization of PPP does not result from a non-specific leakage. Moreover, live unencapsulated bacteria could be stained with an anti-PPP monoclonal antibody, further suggesting that PPP is cell-wall localized. Membrane localization of PPP observed in immunoblots may result from its intracellular enzymatic activity in the PTS system, which occurs near to or at the inner leaflet of the cytoplasmic membrane.

The cell-wall residence, age-dependent immunogenicity, conservation among pneumococcal strains and adhesin activity support the vaccine potential of PPP. Immunization with rPPP reduced nasopharyngeal and lung colonization and reduced mortality upon challenge.

The observations that PPP resides in the cell-wall, demonstrates age-dependent antigenicity, and inhibits adhesion suggest that it could be a candidate vaccine antigen.

EXAMPLES

The following examples are provided for illustrative purposes and in order to more particularly explain and describe the present invention. The present invention, however, is not limited to the particular embodiments disclosed in the examples.

Example 1

Prevention of S. pneumoniae Infection in Mice by Inoculation with S. pneumoniae Cell Wall Protein Fractions Methods:

Bacterial Cells: The bacterial strain used in this study was an S. pneumoniae serotype 3 strain and R6. The bacteria were plated onto tryptic soy agar supplemented with 5% sheep erythrocytes and incubated for 17-18 hours at 37° C. under anaerobic conditions. The bacterial cells were then transferred to Todd-Hewitt broth supplemented with 0-5% yeast extract and grown to mid-late log phase. Bacteria were harvested and the pellets were stored at −70° C.

Purification of Cell Wall Proteins: Bacterial pellets were resuspended in phosphate buffered saline (PBS). The resulting pellets were then treated with mutanolysin to release cell wall components. Supernatants containing the CW proteins were then harvested. Subsequently, the bacteria were sonicated, centrifuged and the resulting pellet containing the bacteria membranes (m) were lysed with 0.5% TRITON™ X-100.

Fractionation of the Cell Wall Protein Mixture: Cell wall protein-containing supernatants were allowed to adhere to fetuin (a highly glycosylated pan-lectin binding protein) that was covalently bound to a sepharose column. Non-adherent molecules, obtained from the flow-through fraction were predominantly non-lectin molecules, while the column-adherent lectins were eluted with 50 mM ammonium acetate at pH 3.5.

Experimental: S. pneumoniae cell wall (CW) proteins were separated into lectin (CW-L) and non-lectin (NL) fractions by fetuin affinity chromatography, as described hereinabove. C57BL/6 and BALB/c mice were vaccinated with S. pneumoniae total CW (CW-T), CW-L and CW-NL protein preparations mixed with Freund's adjuvant, by means of the following procedure: each mouse was primed with 25 micrograms of CW-T, CW-NL and CW-L protein preparations intramuscularly, with complete Freund's adjuvant (CFA) and boosted with incomplete Freund's adjuvant (IFA), 4 and 7 weeks following priming. Western blots of the above-mentioned protein preparations were probed with sera obtained a week after the last immunization. Animals were then challenged intranasally (IN) or intraperitoneally (IP) with $10^8$ cfu of S. pneumoniae serotype 3, that caused 100% mortality in control mice immunized with CFA and boosted with IFA only within 96 hours post-inoculation. Vaccination with CW-L elicited partial protection against S. pneumoniae IN and IP challenge (50% and 45% respectively). Vaccination with CW-T and CW-NL proteins elicited 70% and 65% protection against IP challenge, respectively. Vaccination with CW-T and CW-NL proteins elicited 85% and 50% protection against IN inoculation, respectively.

Example 2

Determination of Agee Related Immunoreactivity to S. pneumoniae Surface Proteins The following study was carried out in order to investigate the age-related development of immunoreactivity to S. pneumoniae cell wall and cell membrane proteins. Operating as described hereinabove in Example 1, a fraction containing cell wall proteins was obtained from a clinical isolate of S. pneumoniae. In addition, cell membrane proteins were recovered by solubilizing the membrane pellet in 0.5% TRITON™ X-100. The cell wall and cell membrane proteins were separated by means of two-dimensional gel electrophoresis, wherein the proteins were separated using polyacrylamide gel isoelectric focusing in one dimension, and sodium dodecyl sulfate polyacrylamide gel electrophoresis (SDS-PAGE) in the other dimension. The separated proteins were either transferred to a nitrocellulose membrane or directly stained with COOMASSIE BRILLIANT BLUE™.

Sera were collected longitudinally from healthy children attending day-care centers at 18, 30 and 42 months of age. Starting at 12 months of age, nasopharyngeal swabs were taken from the children on a bimonthly schedule over the 2.5 years of the study. Pneumococcal isolates were characterized by inhibition with optochin and a positive slide agglutination test (Phadebact, Pharmacia Diagnostics). In addition, sera were collected from healthy adults. The ability of serum prepared from the above-mentioned blood samples to recognize the separated S. pneumoniae proteins was investigated by Western blot analysis according to the methods described by Rapola S. et al. (J. Infect. Dis., 2000, 182: 1146-52). Putative identification of the separated protein spots obtained following the 2D-electrophoresis was achieved by the use of the Matrix Assisted Laser Desorption/Ionization mass spectrometery (MALDI-MS). The results of the above analysis are summarized in the following table:

TABLE 1

Age-dependent immunoreactivity to S. pneumoniae surface proteins

| Spot no. | Proteins/ spot | Homology to | 1.5 | 2.5 | 3.5 | adult |
|---|---|---|---|---|---|---|
| 1 | 2 | DNA K/phosphoenolpyruvate protein Phosphoesterase | * | * | * | * |
| 3 | 1 | Trigger factor | * | * | * | * |
| 4 | 2 | 60 KDa chaperonin (GroEl protein) Eleongation factor G/tetracycline resistance protein teto (TET(O)) | ** | * | ** | *** |
| 7 | 2 | Glutamyl-tRNA amidotransferase subunit A/N utilization sybstance protein protein A | * | ** | | *** |
| 11 | 2 | Oligopeptide-binding protein amiA/aliA/aliB precursor Hypothetical zinc metalloproteinase in SCAA 5'region (ORF 6) | | | | |
| 12 | 1 | Pneumolysin (thiol-activated cytolysin | * | | * | ** |
| 13 | 1 | L-lactate dehydrogenase | * | ** | * | |
| 14 | 1 | Glyceraldehyde 3-phosphate dehydrogenase (GAPDH) | * | ** | *** | *** |
| 15 | 1 | Fructose-bisphosphate aldolase | ** | *** | *** | *** |
| 16 | 1 | UDP-glucose 4-epimerase | ** | * | | |
| 17 | 2 | Elongation factor G/tetracycline resistance protein teto (TET(O)) | * | ** | | |
| 18 | 1 | Pyruvat oxidase | *** | *** | *** | *** |
| 22 | 1 | Glutamyl-tRNA synthetase | | * | ** | |
| 23 | 1 | NADP-specific glutamate dehydrogenase | * | | * | * |
| 24 | 1 | Glyceraldehydes 3-phosphate dehydrogenase (GAPDH) | * | ** | *** | **** |
| 25 | 1 | Enolase (2-phosphoglycerate dehydratase) | * | ** | ** | ** |
| 27 | 1 | Phosphoglycerate kinase | * | ** | ** | ** |
| 29 | 1 | Glucose-6-phosphate isomerase | | * | * | ** |
| 30 | 2 | 40S ribosomal protein S1/6-phosphogluconate dehydrogenase | | | | |
| 31 | 1 | Aminopeptidase C | | | | |
| 33 | | Carbamoyl-phosphate synthase | | * | ** | *** |
| 57/65 | | Aspartate carbamoyltransferase | * | * | ** | ** |
| 58 | | 30S ribosomal protein S2 | ** | * | | |

The data presented in the preceding table indicate that there is an age-dependent development of immunoreactivity to several S. pneumoniae cell wall and cell surface proteins. Ling et al. (Clin. Exp. Immunol. 138:290-298, 2004) further describes identification of S. pneumoniae vaccine candidates. As shown in table 2, it was found that the antigenic proteins from the enriched cell wall extract fell into three groups. The first group comprised proteins with low immunogenicity. The second group consists of antigens for which the immunogenicity seemed to increase with age of children attending daycare centers, while the third group of proteins was highly antigenic with all sera tested. The existence of serum antibodies to a certain bacterial protein does not necessarily indicate their capacity to elicit protective immune response against the bacteria. However, the increase in the antibody response to bacterial proteins which coincides with the diminution in morbidity described in children encouraged to test these antigens for their ability to elicit protection against S. pneumoniae. It is concluded that the immunogenic enzymes with an age dependent increase in antigenicity of S. pneumoniae found in enriched cell wall and membrane extract may represent a novel class of vaccine candidates. As shown herein for the first time many of these identified proteins/enzymes elicit protective level immune responses in mice and afford significant protection against respiratory challenge with virulent S. pneumoniae.

TABLE 2

Identification of S. pneumoniae surface proteins with age-dependent immunogenicity

| | MALDI-TOF analysis | | | | | Immunoreactivity Age (months) | | | |
|---|---|---|---|---|---|---|---|---|---|
| Spot | Homology | Acc. number | Mascot | MW | pI | 1.5 | 2.5 | 3.5 | Adult |
| Proteins with low immunogenicity | | | | | | | | | |
| 1 | DNA K | NP_345035 | 173 | 64.8 | 4.6 | * | * | | |
| 23 | NADP-specific glutamate dehydrogenase | NP_345769 | 186 | 49 | 5.3 | * | * | | * |
| Proteins with increased immunogenicity | | | | | | | | | |
| 7 | Glutamyl-tRNA Amidotransferase subunit A | NP_344959 | 83 | 52 | 4.9 | * | ** | ** | *** |
| 13 | L-lactate dehydrogenase | NP_345686 | 134 | 35.9 | 5.2 | * | ** | * | ** |

TABLE 2-continued

Identification of S. pneumoniae surface proteins with age-dependent immunogenicity

| | MALDI-TOF analysis | | | | | Immunoreactivity Age (months) | | | |
|---|---|---|---|---|---|---|---|---|---|
| Spot | Homology | Acc. number | Mascot | MW | pI | 1.5 | 2.5 | 3.5 | Adult |
| 14 | Glyceraldehyde 3-phosphate dehydrogenase | NP_346439 | 350 | 37.1 | 5.7 | * | ** | *** | *** |
| 15 | Fructose-bisphosphate aldolase | NP_345117 | 106 | 31.5 | 5 | ** | *** | *** | *** |
| 16 | UDP-glucose 4-epimerase | NP_346051 | 116 | 37.5 | 4.8 | ** | * | * | ** |
| 22 | Glutamyl-tRNA synthetase | NP_346492 | 194 | 56 | 4.9 | | * | ** | ** |
| 27 | Phosphoglycerate kinase | NP_345017 | 109 | 41.9 | 4.9 | * | ** | ** | ** |
| 29 | Glucose-6-phosphate isomerase | NP_346493 | 96 | 51.3 | 5.2 | | * | * | ** |
| 30 | 6-phosphogluconate dehydrogenase | NP_344902 | 58 | 53.7 | 4.9 | | | ** | ** |
| 31 | Aminopeptidase C | NP_344819 | 120 | 33.7 | 4.8 | | | ** | ** |
| x | Hypothetical protein | NP_358083 | | 15 | 5.2 | | | * | ** |
| 33 | Carbamoyl-phosphate synthase | NP_345739 | 230 | 116.5 | 4.8 | | * | ** | *** |
| 65 | Aspartate carbamoyltransferase | NP_345741 | 44 | 34.7 | 5.1 | * | * | ** | ** |
| | Proteins with high immunogenicity | | | | | | | | |
| 18 | Pyruvate oxidase | NP_345231 | 168 | 65.3 | 5.1 | *** | *** | *** | *** |
| 25 | Enolase (2-phosphoglycerate dehydratase) | NP_345598 | 215 | 47.1 | 4.7 | ** | ** | ** | ** |

The extent of surface protein recognition by the sera was determined by the optical density as measured by the imager used in our study (α Innotech).
* Low;
** intermediate;
*** high Example 3

Prevention of S. Pneumoniae Infection in Mice with Recombinantly-Expressed S. Pneumoniae Cell Surface Proteins Glycolytic enzymes associated with the cell surface of Streptococcus pneumoniae are antigenic in humans and elicit protective immune responses in the mouse.

The glycolytic enzymes fructose-bisphosphate aldolase (FBA, NP_345117, SEQ ID NO: 13), and Glyceraldehide 3 phosphate dehydrogenase (GAPDH, NP 346439, SEQ ID NO:12), which are associated with the cell surface of S. pneumoniae, were used to immunize mice against S. pneumonia as described in Ling et al., Clin. Exp. Immunol. 138: 290-298. 2004. It was shown that both proteins, which are antigenic in humans, elicit cross-strain protective immunity in mice.

Cloning of Immunogenic S. pneumoniae Surface Proteins: S. pneumoniae fructose-bisphosphate aldolase (hereinafter referred to as "aldolase") and GAPDH proteins were cloned into the pHAT expression vector (BD Biosciences Clontech, Palo Alto, Calif., USA; HAT Vectors encode polyhistidine epitope tag in which the 6 histidine are not consecutive: Lys Asp His Leu Ile His Asn Val His Lys Glu His Ala His Ala His Asn Lys (SEQ ID NO: 36)), and expressed in E. coli BL21 cells (Promega Corp., USA) using standard laboratory procedures. Following lysis of the BL21 cells, recombinant proteins were purified by the use of immobilized metal affinity chromatography (IMAC) on Ni-NTA columns (Qiagen) and eluted with imidazole. In a separate set of experiments, S. pneumoniae aldolase cDNAs were cloned into the pVAC expression vector (Invivogen), a DNA vaccine vector specifically designed to stimulate a immune response by intramuscular injection. Antigenic proteins are targeted and anchored to the cell surface by cloning the gene of interest in frame between the IL2 signal sequence and the C-terminal transmembrane anchoring domain of human placental alkaline phosphatase. The antigenic peptide produced on the surface of muscle cells is taken up by antigen presenting cells (APCs) and processed to be presented to the T helper cells by the major histocompatibility complex (MHC) class II molecules.

Immunization: BALB/c and C57BL/6 mice (7 week old females) were intraperitonealy immunized with 25 micrograms of either recombinant aldolase or recombinant GAPDH proteins together with either Freund's complete adjuvant (CFA) or an alum adjuvant. In a separate set of experiments, mice of the aforementioned strains were intramuscularly immunized with 50 micrograms of the pVAC-aldolase or pVAC-GAPDH constructs that were described hereinabove.

Assessment of Immunogenicity: The immunogenicity of recombinant S. pneumoniae aldolase and GAPDH proteins was assessed by Western blot assay using serum of mice that had been immunized with either total cell wall proteins (CW-T) or with one of the recombinant proteins (as described hereinabove). The results obtained (FIG. 1) indicate that the sera of the immunized animals recognized both recombinant GAPDH and aldolase proteins, and the native GAPDH and aldolase proteins present in the CW-T mixture.

Figure 2:
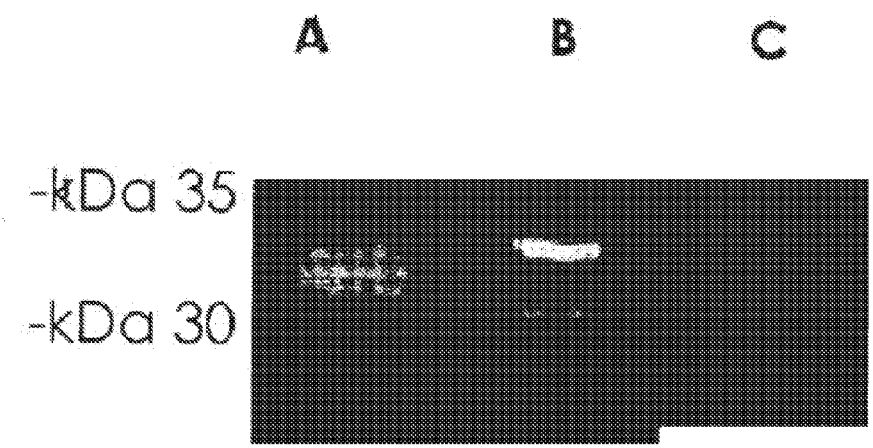
FIG. 2 is a photograph of a Western blot in which the sera of mice immunized with pVAC constructs containing the cDNA of *S. pneumoniae* fructose-bipshosphate aldolase (A) and GAPDH (B) are seen to recognize the corresponding native proteins from electrophoretically-separated total cell wall protein preparation. Sera obtained following immunization with the pVAC parental plasmid did not recognize either of the two proteins (C).

In a separate set of experiments the serum of mice that had been immunized with DNA vaccines of pVAC-aldolase or pVAC-GAPDH constructs, as described above, was used to detect native aldolase and GAPDH, respectively in Western blots obtained from SDS-PAGE separations of CW-T proteins. The results obtained (FIG. 2) indicate that inoculation with the DNA vaccines containing pVAC-based constructs is capable of eliciting an immune response. Sera of mice vaccinated with the parental pVAC plasmid (i.e. without insert) did not react with the CW-T proteins.

Figure 3:
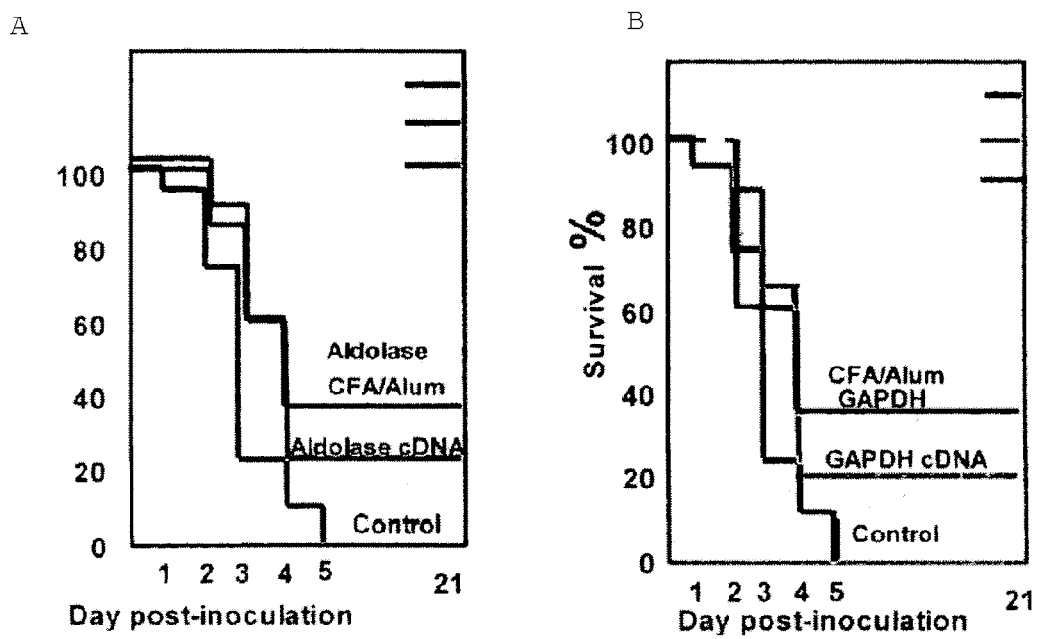
FIGS. 3A and 3B each shows a graph describing the ability of recombinant GAPDH (3B) and fructose-bisphosphate aldolase (3A) to elicit a protective immune response to intraperitoneal and intranasal challenge with a lethal dose of *S. pneumoniae* in the mouse model system.

Protective Vaccination: Following immunization with the recombinant proteins as described hereinabove, the mice were challenged intranasally with a lethal dose of $10^8$ CFU of S. pneumoniae serotype 3. Only 10% of the control animals (immunization with either CFA or alum only) survived the bacterial challenge. However, 40% of the animals immunized with the recombinant aldolase protein in CFA and 43% of the animals immunized with the same protein in alum survived the challenge. In contrast, immunization with the protein DNA K, having low immugenicity (table 2) did not elicit a protective immune response. Following immunization with the pVAC-aldolase construct, 33% of the animals survived. With regard to recombinant GAPDH, 36% of the animals immunized with this recombinant protein survived. Immunization with the pVAC-GAPDH construct, led to a survival rate of 40%, as shown in FIG. 3.

Example 4

S. pneumoniae Immunogenic Proteins

Operating essentially as in Example 2, the ability of serum prepared from blood samples of children aged 1.5, 2.5 and 3.5 years and adults to recognize the separated S. pneumoniae proteins was investigated by Western blot analysis according to the methods described by Rapola S. et al. (J. Infect. Dis., 2000, 182: 1146-52).

Identification of the separated protein spots obtained following the 2D-electrophoresis was achieved by the use of the Matrix Assisted Laser Desorption/Ionization mass spectrometry (MALDI-MS) technique, and comparison of the partial amino acid sequences obtained thereby with the sequences contained in the TIGR4 and/or R6 databases (maintained by The Institute for Genomic Research).

The cell surface proteins found to be immunogenic (classified according to their cellular location—cell membrane or cell wall) are summarized in the following table:

TABLE 3 list of immunogenic proteins

| Spot # | Protein name | Accession No. | SEQ ID NO |
|---|---|---|---|
| 1 | phosphoenolpyruvate protein phosphotransferase | NP_345645 | 4 |
| 2 | phosphoglucomutase/phosphomannomutase family protein | NP_346006 | 5 |
| 3 | trigger factor | NP_344923 | 6 |
| 4 | elongation factor G/tetracycline resistance protein (tetO) | NP_344811 | 7 |
| 6 | NADH oxidase | NP_345923 | 8 |
| 7 | Aspartyl/glutamyl-tRNA amidotransferase subunit C | NP_344960 | 9 |
| 8 | cell division protein FtsZ | NP_346105 | 10 |
| 13 | L-lactate dehydrogenase | NP_345686 | 11 |
| 14 | glyceraldehyde 3-phosphate dehydrogenase (GAPDH) | NP_346439 | 12 |
| 15 | fructose-bisphosphate aldolase | NP_345117 | 13 |
| 16 | UDP-glucose 4-epimerase | NP_346261 | 14 |
| | elongation factor Tu family protein | NP_358192 | 15 |
| 21 | Bifunctional GMP synthase/glutamine amidotransferase protein | NP_345899 | 16 |
| 22 | glutamyl-tRNA synthetase | NP_346492 | 17 |
| 23 | glutamate dehydrogenase | NP_345769 | 18 |
| 26 | Elongation factor TS | NP_346622 | 19 |

TABLE 3-continued list of immunogenic proteins

| Spot # | Protein name | Accession No. | SEQ ID NO |
|---|---|---|---|
| 27 | phosphoglycerate kinase (TIGR4) | AAK74657 | 20 |
| 30 | 30S ribosomal protein S1 | NP_345350 | 21 |
| | 6-phosphogluconate dehydrogenase | NP_357929 | 22 |
| 31 | aminopeptidase C | NP_344819 | 23 |
| 33 | carbamoyl-phosphate synthase (large subunit) | NP_345739 | 24 |
| 57 | PTS system, mannose-specific IIAB components | NP_344822 | 25 |
| 58 | 30S ribosomal protein S2 | NP_346623 | 26 |
| 62 | dihydroorotate dehydrogenase 1B | NP_358460 | 27 |
| 65 | aspartate carbamoyltransferase catalytic subunit | NP_345741 | 28 |
| 14 | elongation factor Tu | NP_345941 | 29 |
| 19 | Pneumococcal surface immunogenic protein A (PsipA) | NP_344634 | 30 |
| 22 | phosphoglycerate kinase (R6) | NP_358035 | 31 |
| 40 | ABC transporter substrate-binding protein | NP_344690 | 32 |
| 10 | endopeptidase O | NP_346087 | 33 |
| 14 | Pneumococcal surface immunogenic protein B (PsipB) | NP_358083 | 34 |
| | Pneumococcal surface immunogenic protein C (PsipC) | NP_345081 | 35 |

Example 5

Preparation of an S. pneumoniae Fructose Bisphosphate Aldolase Fragment

A peptide referred to as ALDO 1, corresponding to the first 294 nucleotides of the coding sequence of the fructose bisphosphate aldolase gene (SP0605 Streptococcus pneumoniae TIGR4) (SEQ ID NO:1), was amplified from S. pneumoniae strain R6 genomic DNA by means of PCR with the following primers:

```
3 Forward
                                      (SEQ ID NO: 2)
(5'-GGT ACC ATG GCA ATC GTT TCA GCA-3'), Reverse
                                      (SEQ ID NO: 3)
(5'-GAG CTC ACC AAC TTC GAT ACA CTC AAG-3').
```

Figure 4:
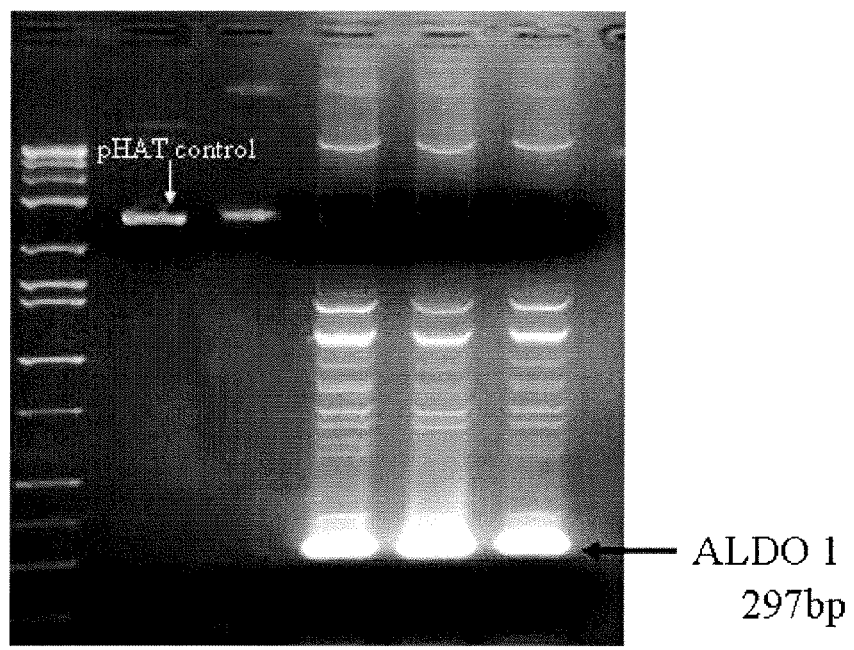
FIG. 4 is a photograph of a gel depicting the 297 base pair ALDO 1-containing fragment of *S. pneumoniae* fructose bisphosphate aldolase.

The amplified product obtained thereby is shown in FIG. 4.

Figure 5:
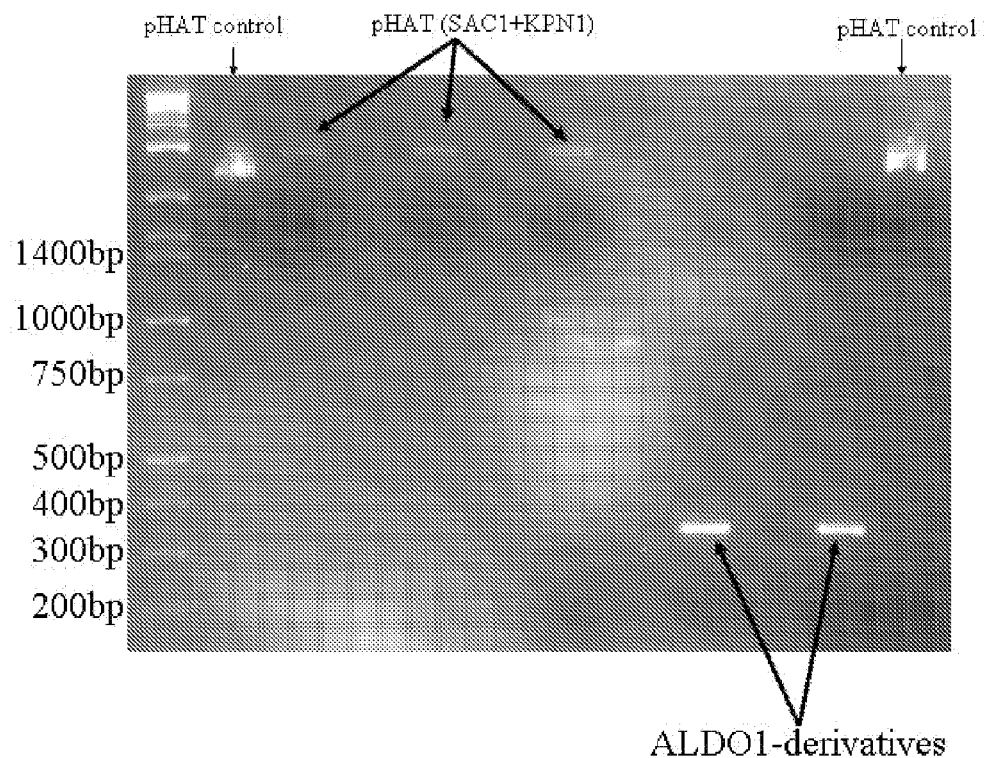
FIG. 5 depicts an agarose gel separation of ALDO 1 and the pHAT vector after restriction by Kpn1 and SacI enzymes.

The Forward and Reverse primers, constructed according to the TIGR4 sequence contain Kpn1 and SacI recognition sequences, respectively. The primers flank the entire open reading frames. The primers were used to amplify the gene from S. pneumoniae serotype 3 strain WU2. The amplified and Kpn1-SacI (Takara Bio Inc, Shiga, Japan) digested DNA-fragments were cloned into the pHAT expression vector (BD Biosciences Clontech, Palo Alto, Calif., USA; as described in Example 3), as illustrated in FIG. 5 and transformed in DH5a UltraMAX ultracompetent E. coli cells.

Figure 6:
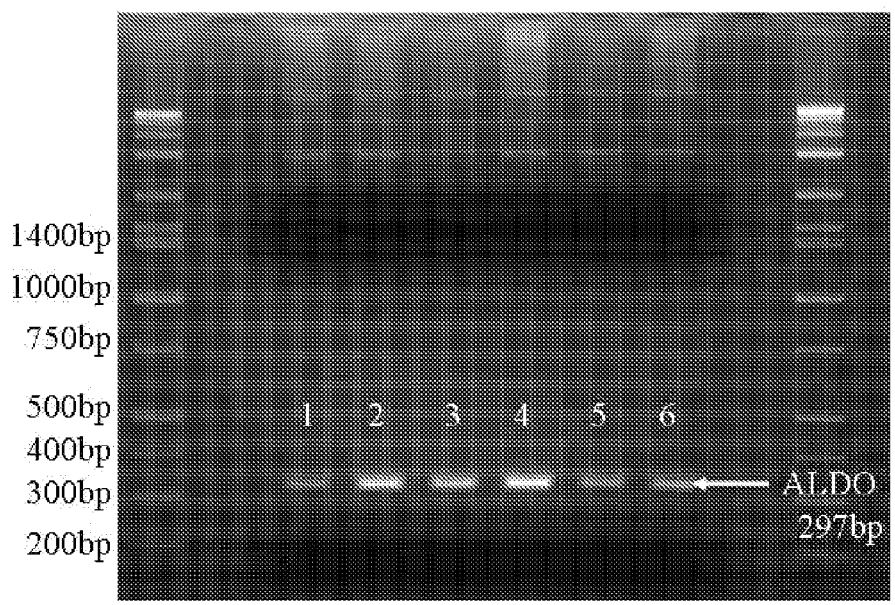
FIG. 6 is a photograph of an agarose gel showing the 297 bp PCR amplification product (comprising ALDO 1) obtained from colonies transformed with the pHAT/ALDO 1 construct.

Ampicillin-resistant transformants were cultured and plasmid DNA was analyzed by PCR. The pHAT-ALDO 1 vector was purified from DH5.alpha. UltraMAX cells using the Qiagen High Speed Plasmid Maxi Kit (Qiagen GMBH, Hilden, Germany) and transformed in E. coli host expression strain BL21(DE3)pLysS. PCR amplification of the ALDO 1 fragment from transformed positive colonies yielded the 297 bp fragment indicated in the gel shown in FIG. 6.

Example 6

Cloning, Expressing and Purification of Recombinant Phosphoenolpyruvate Protein Phosphotransferase (PPP) Proteins Two genetically unrelated encapsulated *S. pneumoniae* strains, serotype 2 strain D39 (Avery 1995, Mol Med 1: 344-365) and serotype 3 strain WU2 (Briles 1981, J Exp Med 153: 694-705) were used together with their unencapsulated derivatives, strain R6 (ATCC, Rockville Md.) and strain 3.8DW (Watson at al., 1990, Infect Immun 58: 3135-3138). Pneumococci were grown in THY or on blood agar plates as previously described (Mizrachi Nebenzahl, et al., 2004, FEMS Microbiol Lett 233: 147-152). Two *Escherichia coli* strains were used, DH5α UltraMAX (DH5α; Invitrogen Corp, Carlsbad, Calif., USA) and BL21(DE3)pLysS (BL21; Promega Corp, Madison, Wis., USA) and were grown in lysogeny broth (LB).

The nucleotide sequence of the NP_345645 PPP protein was amplified from pneumococcal serotype 3 strain WU2 genomic DNA according to the published sequence of serotype 4 strain TIGR4 by PCR with the following primers:
Forward: 5'-GGATCCATGACAGAAATGCTTAAAG-3' (SEQ ID NO:36) and Reverse 5'-GAGCTCTTAAT-CAAAATTAACGTATTC-3' (SEQ ID NO:37) (supplemented with restriction enzyme sequences of BamHI (Takara Biomedicals, Otsoshiga, Japan) on the 3' end and Sac1 on the 5' end (Takara Biomedicals, Otsoshiga, Japan). The amplified product was cloned into the pHAT expression vector (BD Biosciences Clontech, Palo Alto, Calif., USA), and protein expression and purification were performed as previously described (Mizrachi Nebenzahl, et al., 2007 ibid). Verification of sequence identity was performed by plasmid insert sequencing. The tagged-purified protein was resolved by SDS-polyacrylamide gel electrophoresis (PAGE). Pneumococcal cell-wall proteins were separated by SDS-PAGE under reducing conditions and transferred to nitrocellulose membranes (Bio-Rad, Carlsbad, Calif., USA) as previously described (Ausubel F, 1989). Separation showed that the 75 kDa HAT-PPP fusion protein was ~95% pure. The rPPP. The identity of PPP was further confirmed by immunoblot analysis using either rabbit anti-PPP antiserum or human sera. Immunoblotting with anti-HAT antibodies confirmed the identity of the protein sequence was verified by MALDI-TOF analysis as previously described using a Bruker Reflex-IV mass spectrometer (Bruker-Daltonik, Bremen, Germany) (Portnoi, et al., 2006, Vaccine 24: 1868-1873). MALDI-TOF analysis of this protein band identified rPPP in 99% accordance with the expected PPP protein (PI=4.6, Mascot score=92, Z score=2.43, extent of sequence coverage=39).

Immunization of Rabbits with rPPP

Three-month-old white albino rabbits (Harlan Laboratories, Israel) were initially immunized intramuscularly (IM) with 200 µg HAT-rPPP emulsified with complete Freund's adjuvant (CFA) (1:1) in the first immunization or with incomplete Freund's adjuvant (IFA) in booster immunizations. Two weeks after their final immunization rabbits were exsanguinated and sera prepared.

Figure 17:
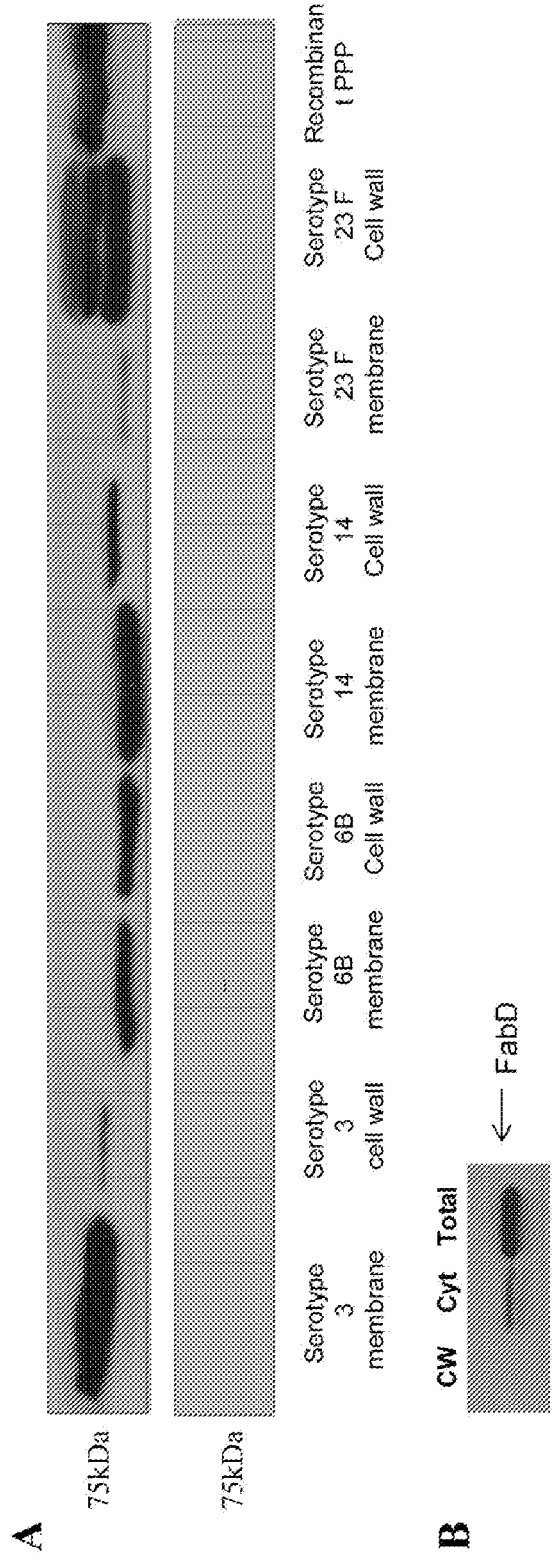
FIG. 17A-B demonstrates surface expression and conservation of PPP in different strains. 17A. Membrane and cell-wall (CW) protein fractions from four clinical isolates were immunoblotted with mouse anti-PtsA antibodies; rPtsA positive control (upper lane). The membrane was immunoblotted with pre-immune serum as negative control (lower lane). 17B. CW and cytoplasmic protein fractions immunoblotted with rabbit anti-FabD antibodies.

Surface Expression and Conservation of PPP in Different Pneumococcal Strains To analyze surface expression and conservation, immunoblot analysis of cell-wall and membrane protein fractions from several pneumococcal strains using anti-rPPP antisera was performed. PPP was found to reside both in the cell-wall and in the membranes of different strains (FIG. 17A). The differences found in the molecular weight of PPP may result from post-translation modifications. In contrast to PPP, no cell-wall residence could be found for the rFabD protein (FIG. 17B).

Alignment of the protein sequence from the R6 strain with the published pneumococcal strains sequences, performed using both the Mascot software package (Matrix Science Ltd., UK) and Profound program (Rockefeller Univ.), demonstrated homology with >99% identity and 100% positivity with no gaps.

Flow cytometry analysis performed as previously described (Mizrachi Nebenzahl, et al., 2007 ibid) with the R6 bacteria strain probed with anti-PPP mAbs demonstrated PPP surface expression. Strain R6 bacteria were incubated with anti-rPPP mAb or pre-immune mouse serum, washed, and stained with Alexa Fluor 647-conjugated goat-anti-mouse-IgG (Jackson ImmunoResearch, West Grove, Pa.). Flow cytometry was performed using a FACSCalibur flow cytometer (Becton Dickinson, Mountain View, Calif.), and data were acquired and analyzed using BD CellQuest™ 3.3 software.

Age-Dependent Immunogenicity of PPP

Figure 18:
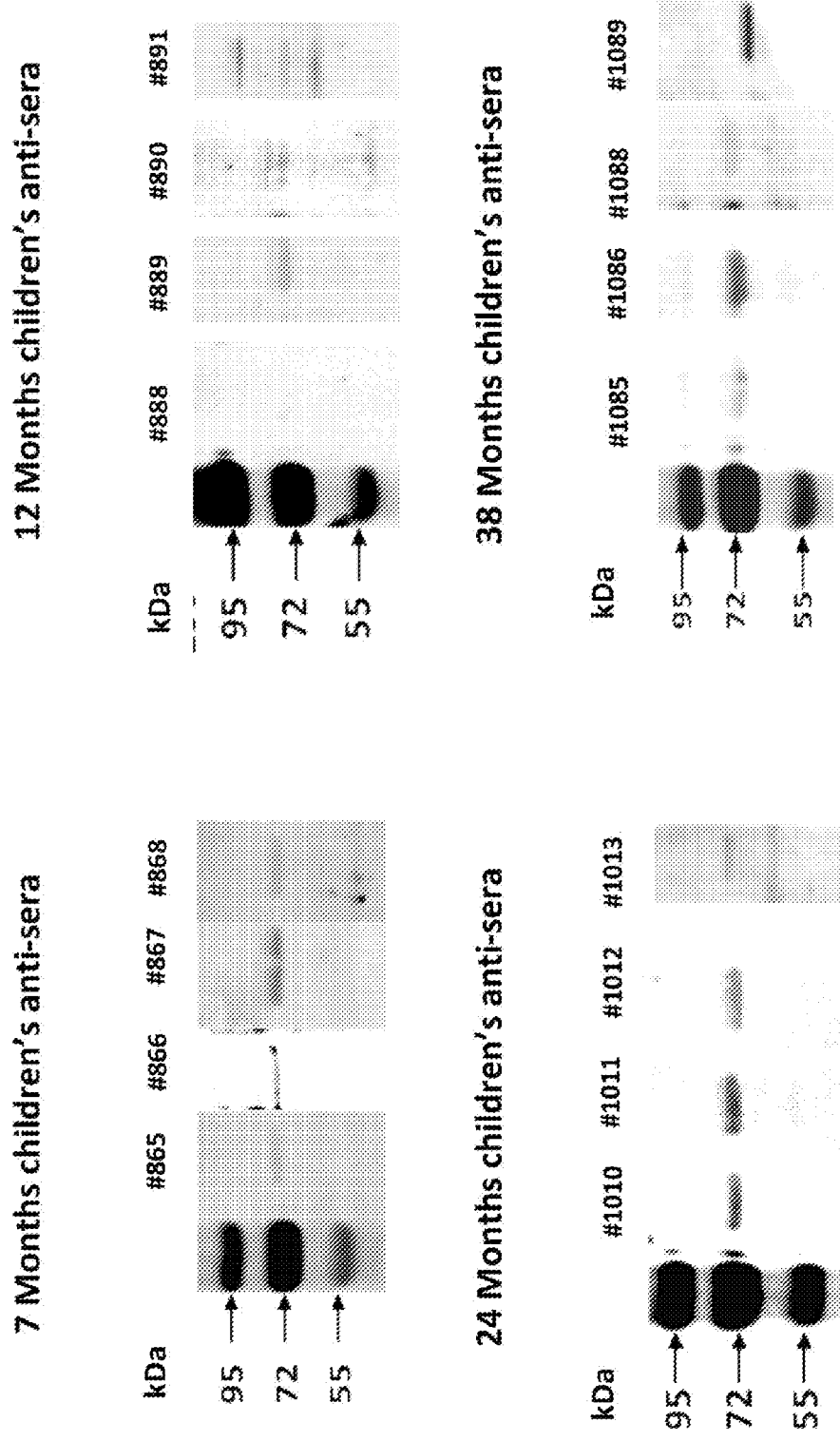
FIG. 18 reconfirms the age dependent immunogenicity of PPP. rPPP was immunoblotted with sera obtained from infants attending day care centers at (18A) 7, (18B) 12, (18C) 24, and (D) 38 months of age.

In previous studies, a group of cell-wall proteins demonstrated age-dependent antigenicity in children. To test whether PPP belongs to this group, rPPP was immunoblotted with pediatric sera. Sera were collected longitudinally at 18, 30 and 42 months of age from healthy children attending day-care centers. Nasopharyngeal swabs were taken from the children bimonthly starting at 12 months of age for the entire 3.5-year duration of the study, and episodes of carriage of different serotype strains were documented (Lifshitz, et al., 2002, Clin Exp Immunol 127: 344-353). Increased PPP antigenicity was observed at 24 months relative to 7 and 12 months with variable recognition at 38 months of age (FIG. 18).

Active Immunization with PPP Reduces Nasopharyngeal and Lung Colonization Upon Intranasal Challenge Seven-week-old BALB/cOlaHsd (BALB/c) female mice (Harlan Laboratories, Israel) or seven-week-old CBA/CaHN-Btk$^{xid}$J (CBA/Nxid; Jackson Laboratories, Bar Harbor, Me., USA) mice were housed in sterile conditions under 12-h light/dark cycles and fed Purina Chow and tap water ad libitum.

Figure 7:
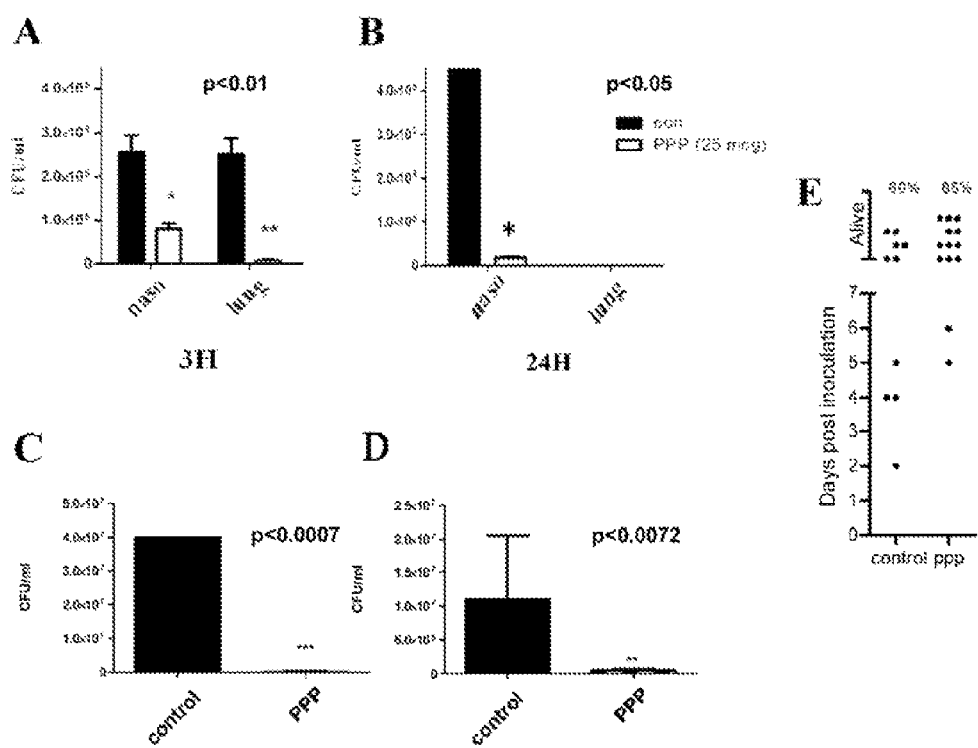
FIG. 7A-E describes the vaccine potential of PPP. BALB/c mice were immunized SC with rPPP formulated with CFA (day 0) and IFA (days 14 & 28), and followed for colonization (7A-7D) or mortality (7E) following IN inoculation. (7A) strain WU2, 3 h ($p<0.01$), (7B) strain WU2 48 h ($p<0.05$), (7C) Strain D39, NP, 48 h ($p<0.001$), (7D) Strain D39, lung, 48 h ($p<0.007$), (7E) Strain WU2, 7 days of observation for mortality ($p<0.05$).

BALB/c or CBA/Nxid mice were immunized subcutaneously (SC) with 5 or 25 µg rPPP or a 25-µg NL fraction as positive control (Portnoi, et al., 2006 ibid), emulsified with CFA and boosted (days 14 and 28) with IFA. One week after third immunization the mice were anesthetized with Terrel isoflurane (MINRAD, NY, USA) and inoculated intranasally (IN) on day 42 with a sublethal dose ($5 \times 10^7$) of *S. pneumoniae* Serotype 3 strain WU2. Mice were sacrificed by cervical dislocation 3 and 48 h later, and the nasopharynx (NP) and right lobe lung were excised, homogenized and samples were plated onto blood agar plates for bacterial enumeration. After a similar immunization regimen, BALB/c mice were challenged IN with a lethal dose ($10^8$ CFU) of strain WU2, and mortality was monitored daily. Mice immunized with rPPP demonstrated a significant reduction in colonization at 3 h (FIG. 7A) and 48 h (FIG. 7B) after inoculation with strain WU2 and at 48 h (FIGS. 7C and D) after inoculation with strain D39. Immunization with rPPP reduced mortality in BALB/c following an IN lethal challenge with WU2 strain ($p < 0.05$, FIG. 7E).

Adhesion is Mediated by PPP

To analyze whether PPP is involved in pneumococcal interaction with the host, the ability of rPPP to inhibit pneumococcal adhesion to cells was tested. A549 cells (type II epithelial lung carcinoma cells; ATCC, Rockville, Md., USA) or Detroit 562 cells (pharyngeal carcinoma derived cells; ATCC, Rockville, Md., USA) were cultured on fibronectin-coated 96-well plates (2.5×10$^4$ cells/well) in DMEM (without antibiotics). Experiments were conducted in triplicate with rPPP (0-600 nM) as previously described (Blau, et al., 2007, J Infect Dis 195: 1828-1837). Inhibition of adhesion to A549 cells by anti-rPPP antibodies was also performed. In a dose-dependent manner, rPPP significantly inhibited the adhesion of strain WU2 and its unencapsulated derivative strain 3.8DW and of D39 and its unencapsulated derivative strain R6. Rabbit anti-rPPP antisera significantly inhibited the adhesion of strains WU2 and 3.8DW. Mouse anti-rPPP antisera significantly inhibited the adhesion of strains D39 and R6 in a dose-dependent manner.

Example 7

Active Immunization with Glutamyl tRNA Synthetase

Active immunization with Glutamyl tRNA synthetase (GtS, NP_346492, SEQ ID NO: 17) using alum as adjuvant is described in Mizrachi et al., J Infect Dis. 196,945-53, 2007. The cloning of the gene was by amplification of the gene using primers constructed according to the TIGR4 sequence and the gene was amplified from *S. pneumoniae* serotype 3 strain WU2. The amplified gene was inserted into the pHAT vector as described in Example 3.

Figure 8:
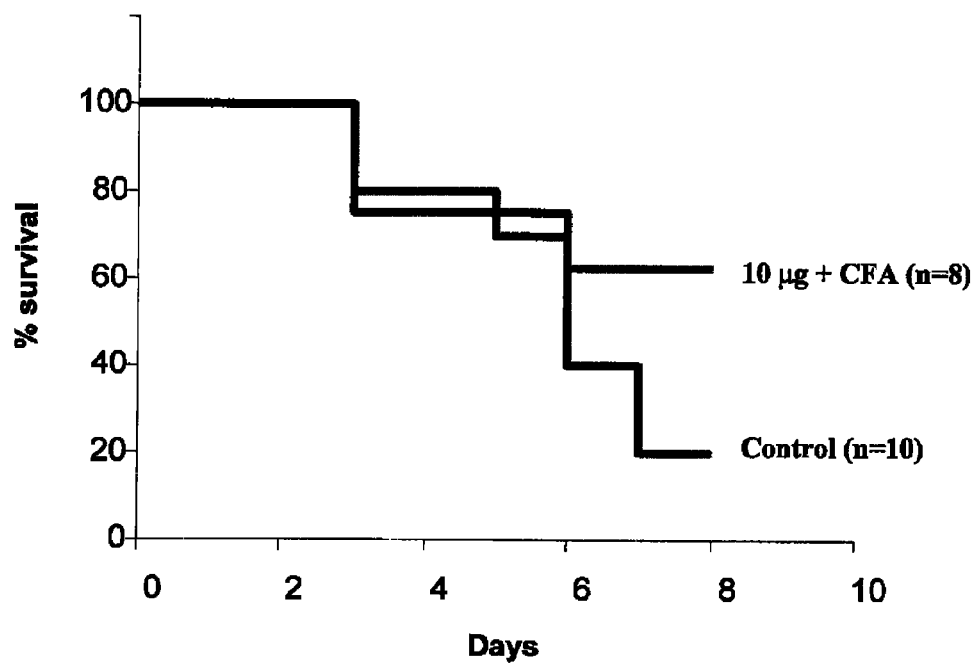
FIG. 8 depicts the increased survival of mice following a lethal intranasal inoculation of mice following immunization with recombinant Glutamyl tRNA synthetase (rGtS)

Thirty-nine percent of rGtS-immunized mice survived a lethal bacterial challenge, whereas no control mice survived. The results suggested that GtS, an age-dependent *S. pneumoniae* antigen, is capable of inducing a partially protective immune response against *S. pneumoniae* in mice. Active immunization with rGtS using CFA as adjuvant: BALB/c mice were immunized three times IM with 10 μg of rGtS in CFA/IFA/IFA in 3 weeks intervals. Mice were subsequently challenged with *S. pneumoniae* serotype 3 strain WU2. Survival was monitored up to 8 days after challenge. As depicted in FIG. 8, sixty percent of immunized mice survived the intranasal lethal challenge as opposed to 20% of adjuvant immunized (control) mice.

Example 8

Active Immunization with NADH Oxidase (NOX)

The cloning of the gene was by amplification of the gene using primers constructed according to the R6 sequence and the gene was amplified from *S. pneumoniae* R6. The amplified gene was inserted into the pHAT vector as described in Example 3.

Figure 9:
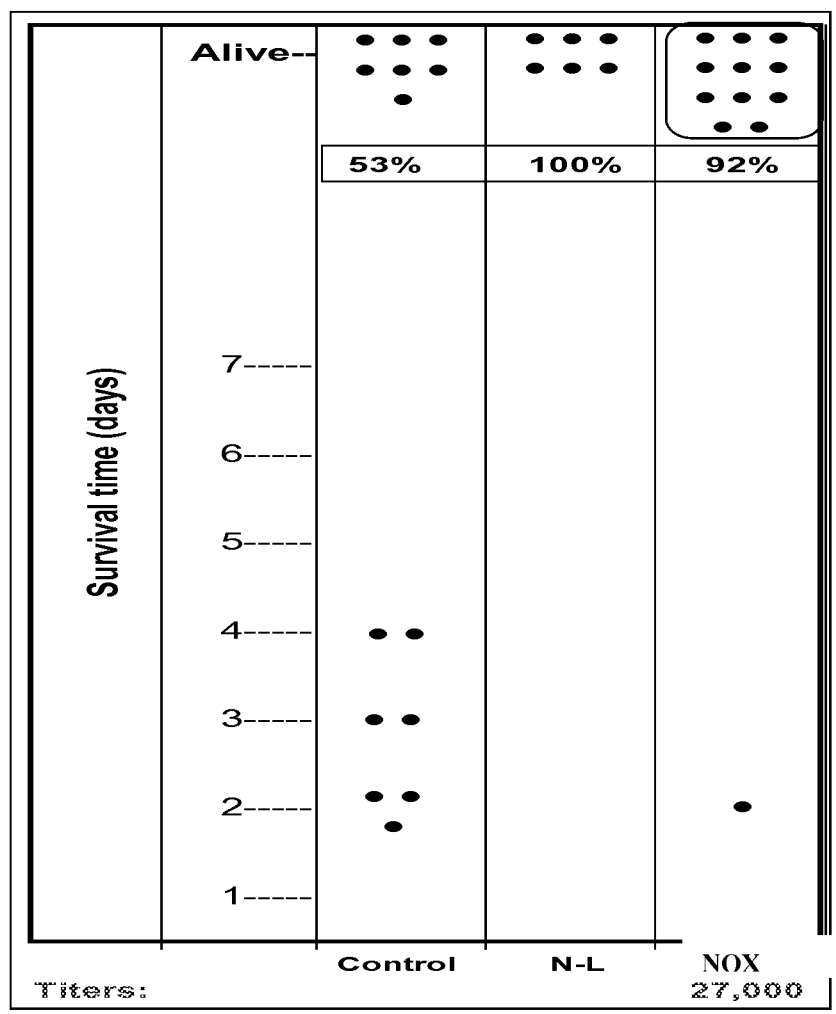
FIG. 9 describes survival of mice following active immunization with recombinant NADH oxidase (rNOX).

BALB/c mice were IP immunized with 25 μg of rNOX protein (NP 345923, SEQ ID NO: 8), 10 μg of a mixture of non-lectin (NL) proteins as a positive control and adjuvant only as a negative control. The immunizations were performed in the presence of CFA in the first immunization and IFA in the following 2 booster immunizations given in two weeks intervals. Mice were subsequently challenged with a lethal dose of *S. pneumoniae* serotype 3 strain (WU2). Survival was monitored daily for 7 days. While only 50% of control mice survived the bacterial challenge 100% of NL immunized and 92% of rNOX immunized mice survived the challenge as shown in FIG. 9.

Example 9

Passive immunization with Pneumococcal surface immunogenic protein B (PsipB; NP_358083, SEQ ID NO:34). The cloning of the gene was by amplification of the gene using primers constructed according to the TIGR4 sequence and the gene was amplified from *S. pneumoniae* serotype 3 strain WU2. The amplified gene was inserted into the pHAT vector as described in Example 3.

Figure 10:
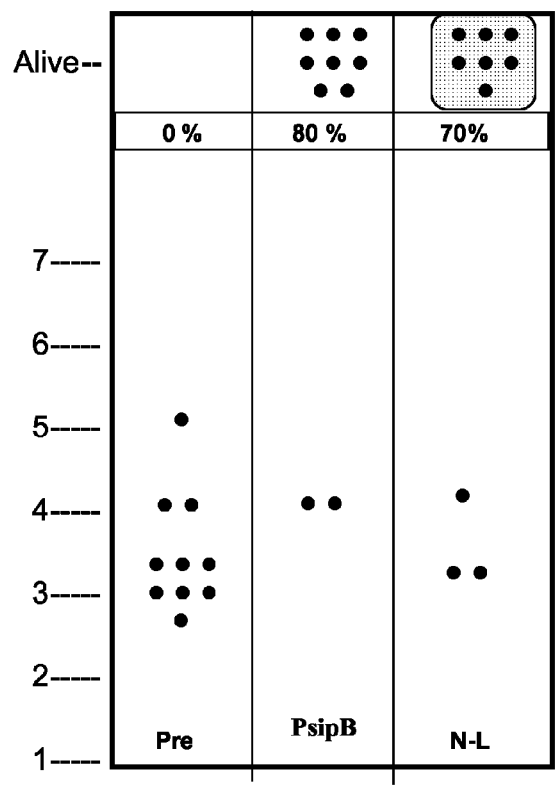
FIG. 10 survival of mice after passive IP immunization with: anti-rPsipB antiserum, control preimmune serum, or anti-non-lectin protein mixture (NL) serum. The mice were inoculated intraperitonealy with the antiserum 24 and 3 hours prior to bacterial challenge.

BALB/c mice were IP passively immunized two times with 100 μl of anti-PsipB antiserum 24 and 3 hours prior to bacterial challenge. Mice were IP challenged with *S. pneumoniae* strain 3 (WU2). Survival was monitored up to 7 days. Administration of either anti PsipB antiserum or the anti NL antisera protected the mice (80 and 70% respectively, FIG. 10) from a lethal challenge, while the control (preimmune) serum did not protect the mice from such challenge.

Example 10

Active Immunization with Trigger Factor (TF, NP 344923, SEQ ID NO:6)

The cloning of the gene was by amplification of the gene using primers constructed according to the TIGR4 sequence and the gene was amplified from *S. pneumoniae* strain R6. The amplified gene was inserted into the pET32a+ vector lacking the thioredoxin sequence. The vector contain a 5.7 kDs tag protein which contains 6 consecutive histidines.

Figure 11:
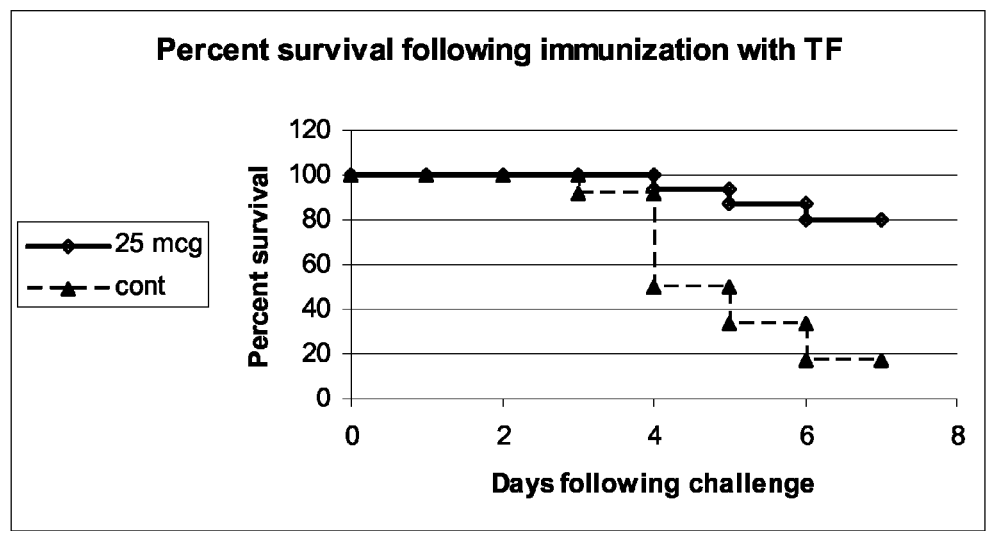
FIG. 11 active immunization of mice with Trigger factor (TF) using CFA/IFA/IFA immunization protocol in comparison to control (adjuvant) immunized animals FIG. 12 survival of mice following IP challenge with *S. pneumoniae* after 1 hour neutralization with anti-FtsZ cell division protein (FtsZ) antiserum, preimmune serum or anti NL serum.

BALB/c mice were IP immunized (three times; CFA/IFA/IFA) with 25 μg of TF. Mice were subsequently challenged IN with *S. pneumoniae* serotype 3 strain WU2. Survival was monitored for 21 days. 25 μg TF elicited a protective immune response against a lethal challenge (80%) while mice immunized with adjuvant only were not protected (19% and 23 survival, respectively, FIG. 11)

Example 11

FtsZ Cell Division Protein (NP_346105, SEQ ID NO:10)

The cloning of the gene was by amplification of the gene using primers constructed according to the TIGR4 sequence and the gene was amplified from *S. pneumoniae* strain R6. The amplified gene was inserted into the pET32a+ vector lacking the thioredoxin sequence The vector contain a 5.7 kDs tag protein which contains 6 consecutive histidines.

Figure 12:
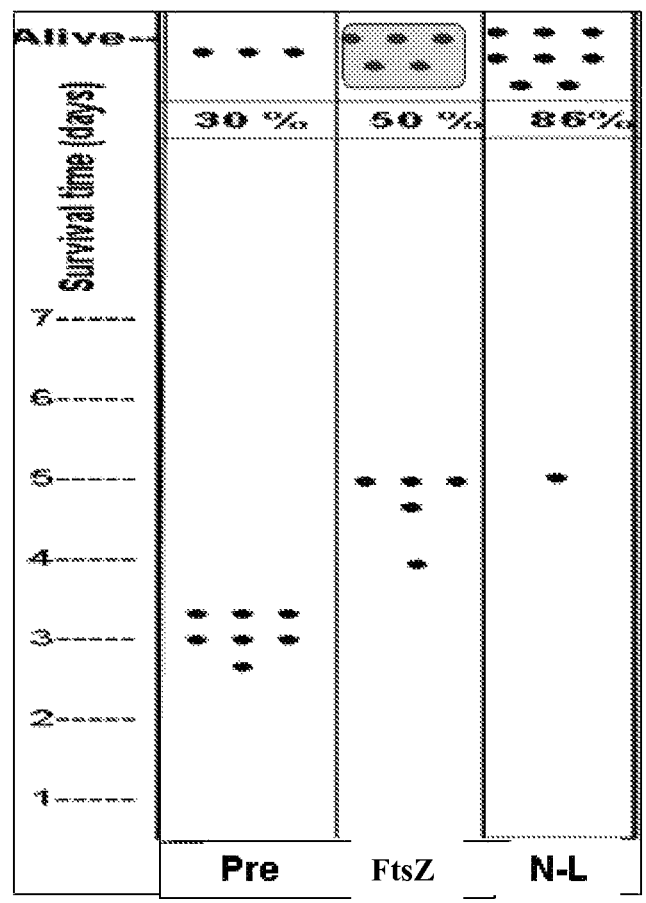

BALB/c mice were IP challenged with *S. pneumoniae* serotype 3 strain WU2 after 1 hour neutralization with rabbit anti-FtsZ antiserum, preimmune serum or anti NL serum. Survival was followed up to 7 days. Both the anti FtsZ and the anti NL antisera protected the mice from a lethal challenge (50% and 86%, respectively), while the preimmune serum protected 30% of the challenged mice (FIG. 12).

Example 12

PTS System, Mannose-Specific IIAB Components NP_344822, SEQ ID NO:25)

The cloning of the gene was by amplification of the gene using primers constructed according to the TIGR4 sequence and the gene was amplified from *S. pneumoniae* strain R6. The amplified gene was inserted into the pET32a+ vector lacking the thioredoxin sequence. The vector contain a 5.7 kDs tag protein which contains 6 consecutive histidines.

Figure 13:
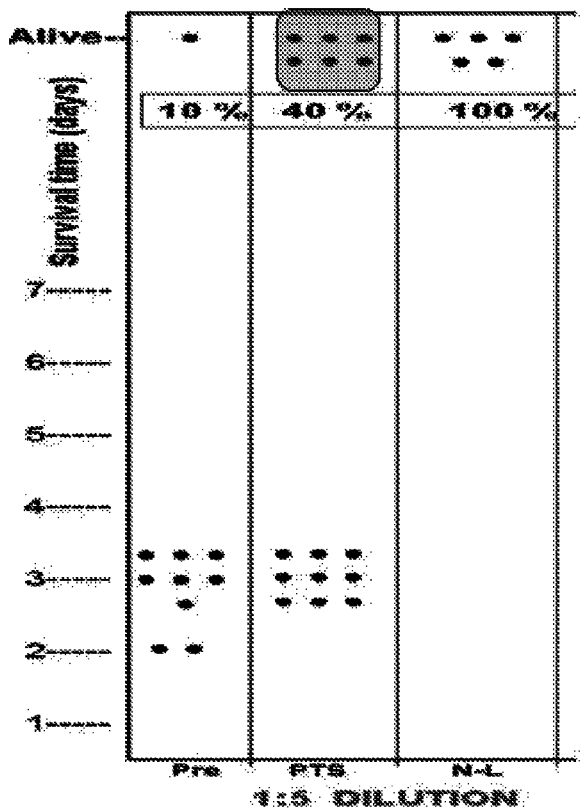
FIG. 13 survival of mice following IP challenge with *S. pneumoniae* neutralized with anti-PTS system, mannose-specific IIAB components (PTS) antiserum, preimmune serum or NL serum.

BALB/c mice were IP challenged with *S. pneumoniae* strain 3(WU2) after 1 hour neutralization with rabbit anti-PTS antiserum. Survival was followed up to 7 days. Both the anti PTS and the anti NL antisera protected the mice from a lethal challenge (40 and 100%, respectively), while only 10% of mice survived following challenge with bacteria pretreated with preimmune serum (FIG. 13).

Example 13

Vaccination with 6-Phosphogluconate Dehydrogenase (6PGD, NP357929, SEQ ID NO:22)

Use of 6PGD for inducing protective immune response in mice was described in Daniely et al., 144:254-63. 2006. Immunization of mice with r6PGD protected 60% of mice for 5 days and 40% of the mice for 21 days following intranasal lethal challenge, while none of the control mice survived the same challenge after four days.

Example 14

Active Immunization with Elongation Factor G (EFG, NP344811, SEQ ID NO:7)

The cloning of the gene was by amplification of the gene using primers constructed according to the R6 sequence and the gene was amplified from S. pneumoniae strain S. pneumoniae serotype 3 strain WU2. The amplified gene was inserted into the pHAT vector lacking the thioredoxin sequence. The vector contains a 5.7 kDs tag protein which contains 6 consecutive histidines.

Figure 14:
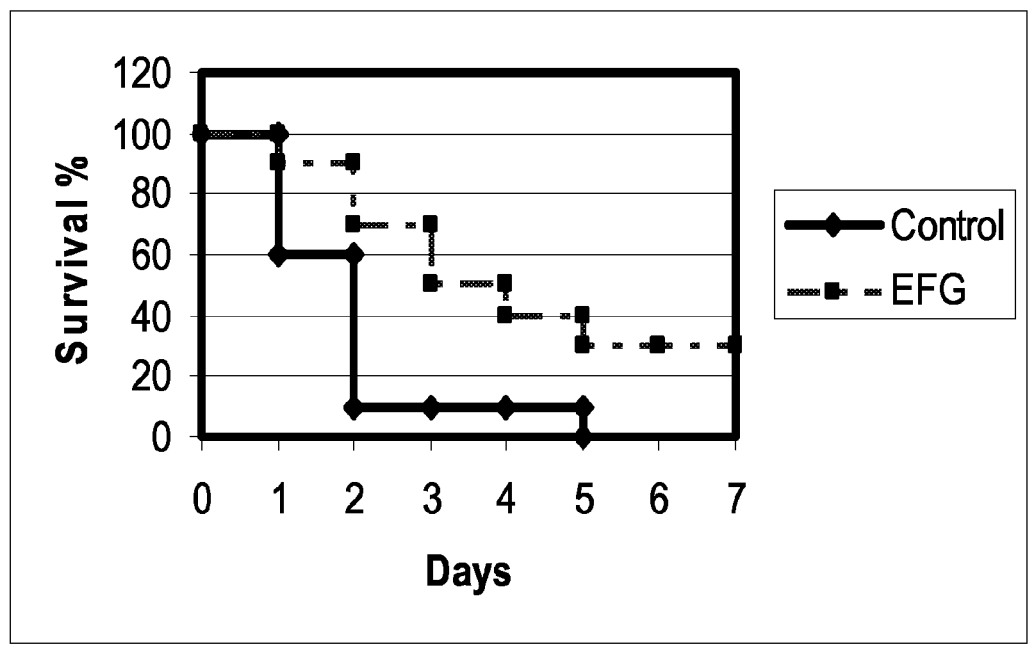
FIG. 14 mice survival after active immunization with Elongation factor G (EFG) with Alum adjuvant in comparison to mice injected with adjuvant only as control.

BALB/c mice were immunized IP with 25 μg of EFG in the presence of Alum. Mice were subsequently challenged IN with S. pneumoniae serotype 3 strain WU2. Survival was monitored for 21 days. As shown in FIG. 14, EFG elicited a protective immune response against a lethal challenge in 30% of the mice, while all control mice, immunized with adjuvant only, succumbed 5 days following the bacterial challenge.

Example 15

Clinical Studies

The first Phase 1 study is performed in 20-25 adults, testing the candidate vaccine for safety and immunogenicity. The second Phase 1 study evaluates 2 or 3 dosage levels of the vaccine in groups of 20-25 infants each for safety and immunogenicity.

The first Phase 2 study is performed in 100-150 infants at a developed world site using the dosage level chosen in Phase 1, and evaluates safety and immunogenicity as well as obtain more information about a potential surrogate assay. The second Phase 2 study at a developed world site is performed in 300-500 in infants in multiple sites, and evaluates interactions with other concomitant vaccines for extended safety and immunogenicity. The third Phase 2 study is performed in parallel 200 infants at the developing world location at which the Phase 3 efficacy study performed, to confirm immunogenicity and safety before Phase 3.

The Phase 3 efficacy study would be performed in a developing world site in 50,000 infants as a placebo-controlled double-blind study with a clinical endpoint.

The Phase 3 immunogenicity study would be performed in parallel in a developed world site using 3 different lots of final manufacturing-scale vaccine in 4 groups of 200 infants each. The Phase 3 safety study would be performed in parallel in 10,000 infants in developed world sites.

Example 16

Verification of Immunogenicity and Age-Dependency of Nox and GtS

Figure 15:
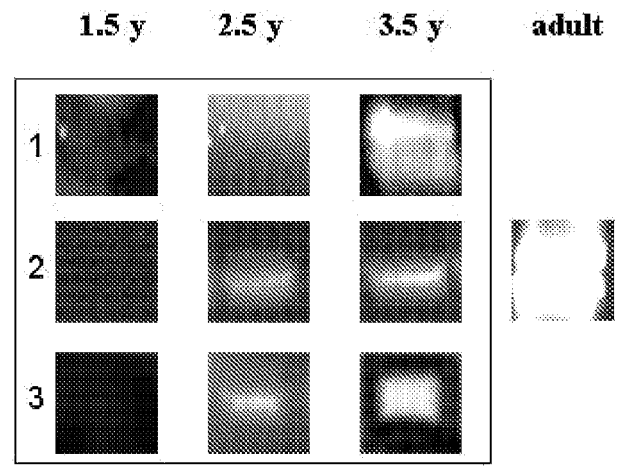
FIG. 15 reconfirms the age dependent recognition of GtS by sera obtained longitudinally from children attending day care centers and a serum obtained from an adult subject.

To verify that GtS induces an age-dependent immune response, sera from 3 healthy children attending day care centers (with documented episodes of carriage of different S. pneumoniae serotypes) were obtained longitudinally between 18-42 months of age. A representative series revealing quantitative and qualitative enhancement of antibody responses to rGtS protein over time is shown in FIG. 15. The rGtS protein was undetected by the infants' sera at 18 and slightly detected at 30 months of age. Maximal detection of rGtS with the children's sera was observed at 42 months of age. Sera obtained from a healthy adult detected rGtS to the highest extent.

Figure 16:
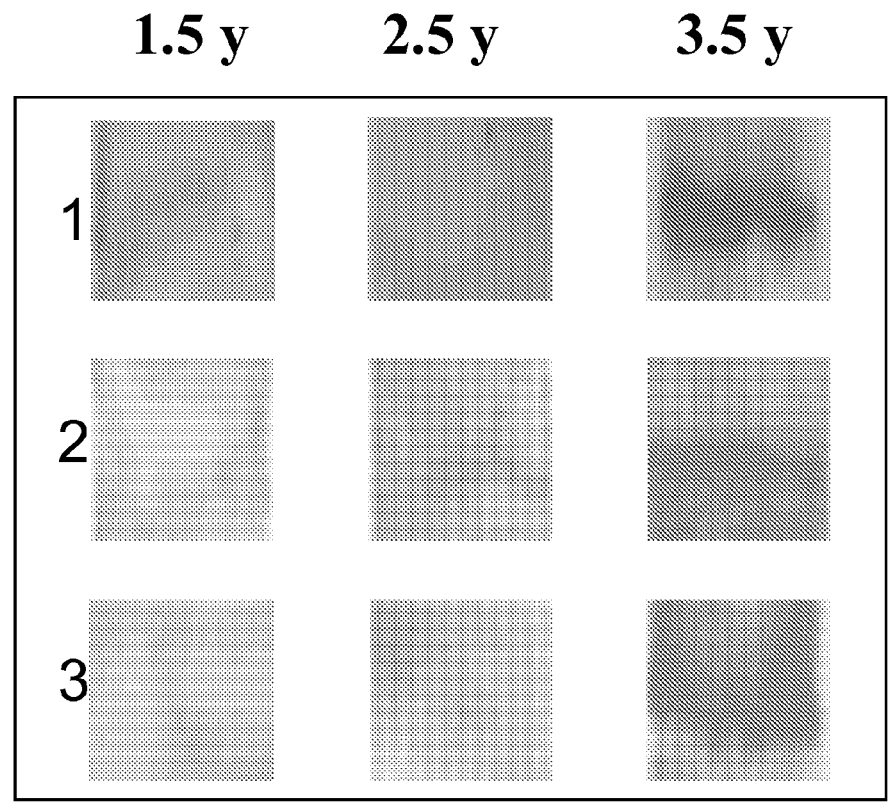
FIG. 16 reconfirms the age dependent recognition of NOX, using rNOX, by sera obtained longitudinally from children attending day care centers.

Immunoblot analysis of rNOX with sera obtained longitudinally from children attending day-care centers demonstrated age-dependent enhancement in protein recognition in all 3 children (FIG. 16).

While specific embodiments of the invention have been described for the purpose of illustration, it will be understood that the invention may be carried out in practice by skilled persons with many modifications, variations and adaptations, without departing from its spirit or exceeding the bounds of the present invention.

What is claimed is:

1. A method of inducing a protective immune response in a mammalian subject against *Streptococcus pneumoniae* comprising administering to said subject an amount of a vaccine composition comprising a purified cell wall protein preparation of *Streptococcus pneumoniae* containing the phosphophenolpyruvate protein transferase having the accession number NP_345645 and comprising the amino acid sequence of SEQ ID NO: 4, wherein the amount is effective to induce said protective immune response in said subject against *Streptococcus pneumoniae*.

2. The method of claim 1, wherein the vaccine composition comprises a diluent.

3. The method of claim 1, wherein the vaccine composition comprises one or more pharmaceutically acceptable adjuvants.

4. The method of claim 1, wherein the vaccine composition is administered parenterally.

* * * * *